United States Patent
Halioua-Haubold et al.

(10) Patent No.: US 12,161,636 B2
(45) Date of Patent: Dec. 10, 2024

(54) METHOD OF INCREASING LIFESPAN IN MAMMALS

(71) Applicant: Cellular Longevity, Inc., San Francisco, CA (US)

(72) Inventors: Celine-Lea Halioua-Haubold, San Francisco, CA (US); Michael Lacroix-Fralish, San Francisco, CA (US); Matt Peloquin, San Francisco, CA (US); Dina Juarez-Salinas, San Francisco, CA (US); Karen Greenwood, San Francisco, CA (US)

(73) Assignee: Cellular Longevity, Inc., San Francisco, CA (US)

( * ) Notice: Subject to any disclaimer, the term of this patent is extended or adjusted under 35 U.S.C. 154(b) by 0 days.

(21) Appl. No.: 18/621,541

(22) Filed: Mar. 29, 2024

(65) Prior Publication Data

US 2024/0325365 A1   Oct. 3, 2024

Related U.S. Application Data

(63) Continuation of application No. PCT/US2024/021756, filed on Mar. 27, 2024.

(60) Provisional application No. 63/454,874, filed on Mar. 27, 2023.

(51) Int. Cl.
    *A61K 31/4439* (2006.01)
    *A61P 3/00* (2006.01)
    *A61P 3/10* (2006.01)
    *A61P 43/00* (2006.01)

(52) U.S. Cl.
    CPC .......... *A61K 31/4439* (2013.01); *A61P 3/00* (2018.01); *A61P 3/10* (2018.01); *A61P 43/00* (2018.01)

(58) Field of Classification Search
    CPC ................................. A61K 31/4439
    See application file for complete search history.

(56) References Cited

FOREIGN PATENT DOCUMENTS

WO    WO 2019/104065    * 5/2019

OTHER PUBLICATIONS

Bajaj, et al. Effects of pioglitazone on intramyocellular fat metabolism in patients with type 2 diabetes mellitus. The Journal of Clinical Endocrinology and Metabolism 95(4):1916-1923 (2010).
Bril, et al. Response to Pioglitazone in Patients With Nonalcoholic Steatohepatitis With vs Without Type 2 Diabetes. Clinical Gastroenterology and Hepatology 16(4):558-566.e2 (2018).
Chen, et al. Evaluating instruments for assessing healthspan: a multi-center cross-sectional study on health-related quality of life (HRQL) and frailty in the companion dog. Geroscience 45(4):2089-2108 (2023).
Coate et al., Chronic consumption of a high-fat/high-fructose diet renders the liver incapable of net hepatic glucose uptake. Am J Physiol Endocrinol Metab 299:E887-E898 (2010).
Davies et al., Optimising outputs from a validated online instrument to measure health-related quality of life (HRQL) in dogs. PLOS One 14(9):e0221869 (2019).
De Souza , et al. Effects of pioglitazone on adipose tissue remodeling within the setting of obesity and insulin resistance. Diabetes 50(8):1863-1871 (2001).
Hallakou, et al. Pioglitazone induces in vivo adipocyte differentiation in the obese Zucker fa/fa rat. Diabetes 46(9):1393-1399 (1997).
Ikeda, et al. Effects of pioglitazone on glucose and lipid metabolism in normal and insulin resistant animals. Arzneimittelforschung 40(2 Pt 1):156-62 (1990).
Ikeda, et al. Pioglitazone rapidly increases serum adiponectin levels in men with normal glucose tolerance. Diabetes Care 30(6):p. e48 (2007).
International Conference on Harmonization of Technical Requirements for Registration of Pharmaceuticals for Human Use (ICH). Impurities: Guidelines for Residual Solvents Q3C(R6) pp. 1-24 (2005).
Koenen, et al. Pioglitazone treatment enlarges subcutaneous adipocytes in insulin-resistant patients. The Journal of Clinical Endocrinology and Metabolism 94(11):4453-4457 (2009).
Matsuhisa, et al. The effect of pioglitazone on hepatic glucose uptake measured with indirect and direct methods in alloxan-induced diabetic dogs. Diabetes 46(2):224-231 (1997).
Miyazaki, et al. Effect of pioglitazone on abdominal fat distribution and insulin sensitivity in type 2 diabetic patients. The Journal of Clinical Endocrinology and Metabolism 87(6):2784-2791 (2002).
Park et al., Effects of MHY908, a New Synthetic PPARα/γ Dual Agonist, on Inflammatory Responses and Insulin Resistance in Aged Rats. The Journals of Gerontology: Series A, 71(3):300-309 (2016).
PCT/US2024/021756 International Invitation to Pay Additional Fees dated Jun. 10, 2024.
Phillips, et al. Adiponectin secretion and response to pioglitazone is depot dependent in cultured human adipose tissue. American Journal of Physiology-Endocrinology and Metabolism 295(4):E842-E850 (2008).
Rasouli, et al. Pioglitazone improves insulin sensitivity through reduction in muscle lipid and redistribution of lipid into adipose tissue. American Journal of Physiology-Endocrinology and Metabolism 288(5):E930-E934 (2005).
Sanrame, et al. Prodrugs of pioglitazone for extended-release (XR) injectable formulations. Molecular Pharmaceutics 11(10):3617-3623 (2014).

(Continued)

*Primary Examiner* — Rei Tsang Shiao
(74) *Attorney, Agent, or Firm* — WILSON SONSINI GOODRICH & ROSATI

(57) ABSTRACT

Provided herein are methods of mitigating or reversing an aging-induced insulin resistance and/or elevation of fatty acids comprising a composition comprising a PPARγ agonist, or a pharmaceutically acceptable salt or prodrug thereof. Provided herein are methods of increasing lifespan comprising a composition comprising a PPARγ agonist, or a pharmaceutically acceptable salt or prodrug thereof, and uses thereof in animal health.

25 Claims, 25 Drawing Sheets

(56) References Cited

OTHER PUBLICATIONS

Figure 1:
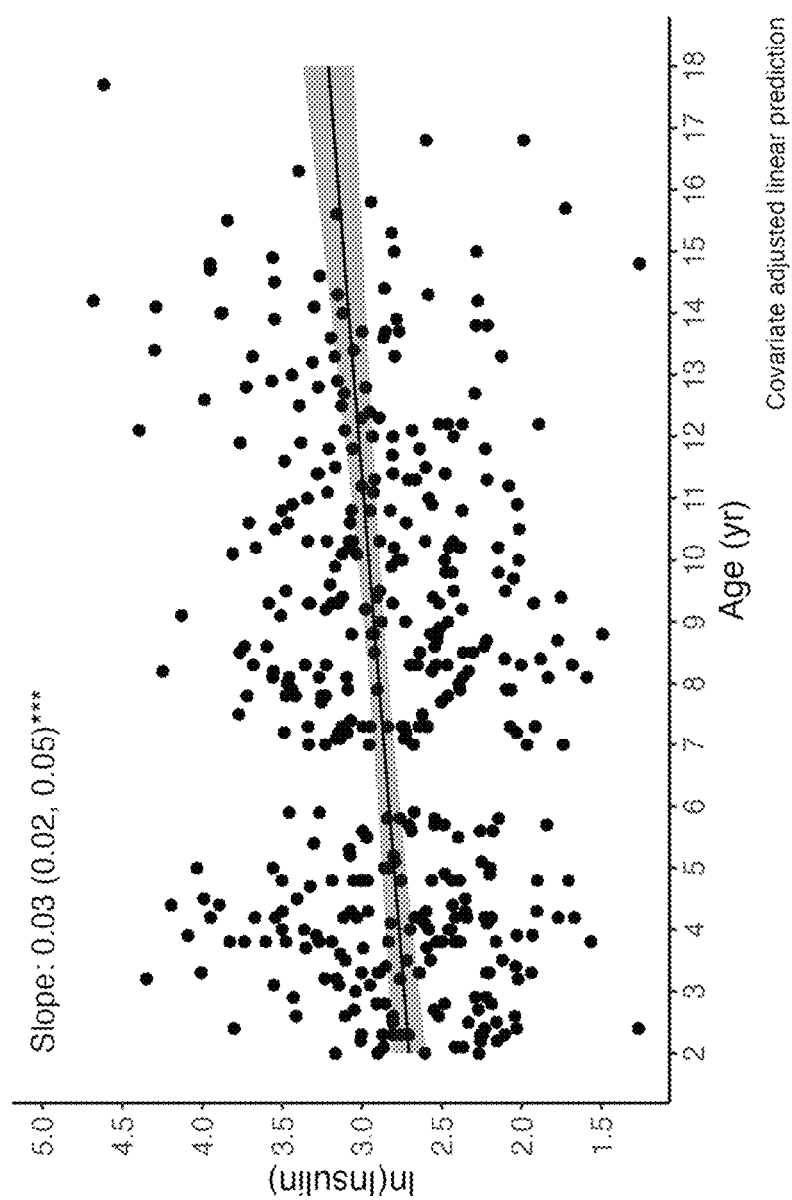

Shimizu, et al. Pioglitazone increases circulating adiponectin levels and subsequently reduces TNF-alpha levels in Type 2 diabetic patients: a randomized study. Diabetic Medicine 23(3):253-257 (2006).
Smith, et al. Effect of pioglitazone on body composition and energy expenditure: a randomized controlled trial. Metabolism 54(1):24-32 (2005).
Zhang, et al. Pioglitazone inhibits the expression of inflammatory cytokines from both monocytes and lymphocytes in patients with impaired glucose tolerance. Arteriosclerosis, Thrombosis, and Vascular Biology 28(12):2312-2318 (2008).
Clark et al., Effects of pioglitazone on insulin sensitivity and serum lipids in obese cats. Journal of Veterinary Internal Medicine 28:166-174 (2014).
Ikeda et al., Insulin resistance-reducing effect of a new thiazolidinedione derivative, pioglitazone. Nihon Yakurigaku Zasshi (Folia Pharmacol. Jpn.) 117(5):335-342 (2001) (English abstract).
Legere et al., Pharmacodynamic effects of pioglitazone on high molecular weight adiponectin concentrations and insulin response after oral sugar in equids. Journal of Equine Veterinary Science 82:1-9 (2019).
Wearn et al., Pharmacokinetics of pioglitazone after multiple oral dose administration in horses. Journal of Veterinary Pharmacology and Therapeutics 34:252-258 (2010).

\* cited by examiner

METHOD OF INCREASING LIFESPAN IN MAMMALS

CROSS REFERENCE TO RELATED APPLICATIONS

This application is a continuation of International Application No. PCT/US24/21756, filed Mar. 27, 2024, which claims the benefit of U.S. Provisional Application No. 63/454,874, filed Mar. 27, 2023, each of which is entirely incorporated herein by reference.

BACKGROUND

Chronological age is well understood to be the single greatest risk factor for nearly every major cause of mortality and morbidity in living organisms, including humans and companion dogs. Even before the development of observable disease, the physiology of organ systems and tissues progressively declines throughout life. Throughout history, products and methods that promote longevity and extend lifespan have been eagerly sought. Generally, these products and methods have proven to be ineffective and/or unsafe. Accordingly, there remains an unmet need for safe and effective products and methods that promote longevity and extend lifespan.

SUMMARY

In some embodiments, provided herein is a method for mitigating or reversing an aging-induced insulin resistance in a mammal in need thereof, comprising administering to the mammal a therapeutically effective amount of a formulation comprising a PPARγ agonist, or a pharmaceutically acceptable salt or prodrug thereof.

In some embodiments, provided herein is a method for mitigating or reversing insulin resistance in a mammal in need thereof, comprising administering to the mammal a therapeutically effective amount of a formulation comprising a PPARγ agonist, or a pharmaceutically acceptable salt or prodrug thereof.

In some embodiments, provided herein is a method for mitigating or reversing an aging-induced elevation of fatty acids and other lipids in a mammal in need thereof, comprising administering to the mammal a therapeutically effective amount of a formulation comprising a PPARγ agonist, or a pharmaceutically acceptable salt or prodrug thereof.

In some embodiments, provided herein is a method of maintaining healthy functioning of adipose tissue in a mammal in need thereof, comprising administering to the mammal a therapeutically effective amount of a formulation comprising a PPARγ agonist, or a pharmaceutically acceptable salt or prodrug thereof.

In some embodiments, the method does not decrease glucose levels in the mammal. In some embodiments, the method does not increase glucose levels in the mammal. In some embodiments, the method comprises decreasing insulin levels in the mammals. In some embodiments, the decreasing insulin levels is decreased by at least 5%. In some embodiments, the decreasing insulin levels is decreased by at least 10%, at least 15%, or at least 20%.

In some embodiments, the method improves insulin sensitivity. In some embodiments, the insulin sensitivity is measured by an oral glucose tolerance testing assay. In some embodiments, the insulin sensitivity is measured by using fasting insulin blood levels. In some embodiments, the insulin sensitivity is measured by a hyperinsulinemic euglycemic clamp testing assay.

In some embodiments, the lipid is aggregated free fatty acids, saturated fatty acids, palmitic acid, linoleic acid, or oleic acid or any combination thereof. In some embodiments, the fatty acid is saturated fatty acids, palmitic acid, linoleic acid, or oleic acid. In some embodiments, the fatty acid is saturated fatty acids. In some embodiments the fatty acid is palmitic acid. In some embodiments, the method decreases triglyceride levels in the mammal. In some embodiments the method decreases cholesterol levels in the mammal. In some embodiments, the method increases adiponectin levels in the mammal.

In some embodiments, the mammal is a dog, cat, horse, cow, pig, rabbit, rodent, sheep, non-human primate, or human. In some embodiments, the mammal is a dog or cat. In some embodiments, the mammal is a dog. In some embodiments, the mammal is a cat. In some embodiments, the rodent is a mouse or a rat. In some embodiments, the mammal is a human.

In some embodiments, the mammal is at least 7 years old. In some embodiments, the mammal is at least 10 years old.

In some embodiments, the formulation comprises about 3% to about 35% of the PPARγ agonist. In some embodiments, the formulation comprises about 10% to about 20% of the PPARγ agonist. In some embodiments, wherein the formulation comprises about 1 mg to about 100 mg of the PPARγ agonist. In some embodiments, the formulation comprises about 4 mg to about 85 mg of the PPARγ agonist. In some embodiments, the PPARγ agonist is administered at 3 mg/kg/day. In some embodiments, the PPARγ agonist is administered at 5 mg/kg/day. In some embodiments, the PPARγ agonist is administered at 10 mg/kg/day. In some embodiments, the formulation is administered for at least about 4 weeks. In some embodiments, the formulation is administered for at least about 12 weeks. In some embodiments, the formulation is administered for at least about 6 months. the formulation is administered for at least about 1 year. In some embodiments, the formulation is administered daily.

In some embodiments, the PPARγ agonist is pioglitazone. In some embodiments, the pioglitazone is administered at 1 mg/kg/day. In some embodiments, the pioglitazone is administered at 2 to 3 mg/kg/day. In some embodiments, the PPARγ agonist is rosiglitazone.

In some embodiments, the formulation is a pharmaceutical formulation. In some embodiments, the formulation is a nutraceutical formulation.

In some embodiments, the formulation is in the form of a tablet. In some embodiments, the tablet comprises hydrolyzed chicken product. In some embodiments, the tablet comprises 18 mg, 54 mg, or 81 mg of the PPARγ agonist. In some embodiments, the tablet further comprises at least one filler. In some embodiments, the filler is lactose monohydrate. In some embodiments, the lactose monohydrate is in an amount of about 10% to about 40% w/w. In some embodiments, the lactose monohydrate is in an amount of about 22% w/w. In some embodiments, the tablet further comprises carboxymethyl cellulose Na. In some embodiments, the carboxymethyl cellulose Na is in an amount of about 2% to about 10% w/w. In some embodiments, the carboxymethyl cellulose Na is in an amount of about 4% w/w. In some embodiments, the tablet further comprises FlavorPAL X1212. In some embodiments, the FlavorPAL X1212 is in an amount of about 10% to about 40% w/w. In some embodiments, the FlavorPAL X1212 is in an amount of about 20% w/w. In some embodiments, the tablet further comprises magnesium stearate. In some embodiments, the magnesium stearate is in an amount of about 0.25% to about 3% w/w. In some embodiments, the magnesium stearate is in an amount of about 1% w/w.

In some embodiments, provided herein is a method for reducing or delaying mortality due to age-associated diseases in a mammal in need thereof, comprising administering to the mammal a therapeutically effective amount of a PPARg agonist, or a pharmaceutically acceptable salt or prodrug thereof. In some embodiments, provided herein is a method for treating the age-related decline in quality of life, comprising administering to the mammal a therapeutically effective amount of a PPARγ agonist, or a pharmaceutically acceptable salt or prodrug thereof.

In some embodiments, provided herein is a method for treating an age-related decline in quality of life, comprising administering to the mammal a therapeutically effective amount of a PPARγ agonist, or a pharmaceutically acceptable salt or prodrug thereof.

In some embodiments, provided herein is a method for treating the age-related increase in frailty, comprising administering to the mammal a therapeutically effective amount of a formulation comprising a PPARγ agonist, or a pharmaceutically acceptable salt or prodrug thereof.

In some embodiments, the method further comprises increasing life span, wherein the increasing lifespan comprises an at least 5% increase in lifespan relative to the expected or median lifespan of a mammal of similar species, strain, or breed. In some embodiments, increasing lifespan comprises an at least 10%, at least 15%, at least 20%, or at least 25% increase in lifespan.

In some embodiments, the method comprises mitigating or reversing insulin resistance in the mammal. In some embodiments, the insulin resistance occurs from an aging process. In some embodiments, the method comprises mitigating or reversing an elevation of free fatty acids (FFAs). In some embodiments, the elevation of free fatty acids is associated with an age-related disease state. In some embodiments, wherein the age-related disease state is obesity, type II diabetes, cardiovascular disease, or sarcopenia. In some embodiments the elevation of free fatty acids is due to advanced chronological age. In some embodiments the elevation of free fatty acids with age is associated with an elevation in fasting insulin.

In some embodiments, the mammal has reached maturity. In some embodiments, the mammal has reached old age. In some embodiments, the mammal is at least 7 years old. In some embodiments, the mammal is at least 10 years old. In some embodiments, the mammal is at least 14 pounds.

In some embodiments, the mammal is a dog, cat, horse, cow, pig, rabbit, rodent, sheep, non-human primate, or human. In some embodiments, the mammal is a dog or cat. In some embodiments, the mammal is a dog. In some embodiments, the mammal is a cat. In some embodiments, the rodent is a mouse or a rat. In some embodiments, the mammal is a human. In some embodiments, the method comprises about 3% to about 35% of the PPARγ agonist. In some embodiments, the method comprises about 10% to about 20% of the PPARγ agonist. In some embodiments, wherein the method comprises about 1 mg to about 100 mg of the PPARγ agonist. In some embodiments, the method comprises about 4 mg to about 85 mg of the PPARγ agonist. In some embodiments, the PPARγ agonist is administered at 3 mg/kg/day. In some embodiments, the PPARγ agonist is administered at 5 mg/kg/day. In some embodiments, the PPARγ agonist is administered at 10 mg/kg/day. In some embodiments, the PPARγ agonist is administered for at least about 4 weeks. In some embodiments, the PPARγ agonist is administered for at least about 12 weeks. In some embodiments, the PPARγ agonist is administered for at least about 6 months. In some embodiments, the PPARγ agonist is administered for at least about 1 year. In some embodiments, the PPARγ agonist is administered daily.

In some embodiments, the PPARγ agonist is pioglitazone. In some embodiments, the pioglitazone is administered at 1 mg/kg/day. In some embodiments, the pioglitazone is administered at 2 to 3 mg/kg/day. In some embodiments, the PPARγ agonist is rosiglitazone. In some embodiments, the formulation is a pharmaceutical formulation. In some embodiments, the formulation is a nutraceutical formulation.

In some embodiments, the formulation is in the form of a tablet. In some embodiments, the tablet comprises hydrolyzed chicken product. In some embodiments, the tablet comprises 18 mg, 54 mg, or 81 mg of the PPARγ agonist. In some embodiments, the tablet further comprises at least one filler. In some embodiments, the filler is lactose monohydrate. In some embodiments, the lactose monohydrate is in an amount of about 10% to about 40% w/w. In some embodiments, the lactose monohydrate is in an amount of about 22% w/w. In some embodiments, the tablet further comprises carboxymethyl cellulose Na. In some embodiments, the carboxymethyl cellulose Na is in an amount of about 2% to about 10% w/w. In some embodiments, the carboxymethyl cellulose Na is in an amount of about 4% w/w. In some embodiments, the tablet further comprises FlavorPAL X1212. In some embodiments, the FlavorPAL X1212 is in an amount of about 10% to about 40% w/w. In some embodiments, the FlavorPAL X1212 is in an amount of about 20% w/w. In some embodiments, the tablet further comprises magnesium stearate. In some embodiments, the magnesium stearate is in an amount of about 0.25% to about 3% w/w. In some embodiments, the magnesium stearate is in an amount of about 1% w/w.

In some embodiments, provided herein is a formulation comprising pioglitazone or a pharmaceutically acceptable salt thereof, for use in reducing or delaying mortality due to age-associated diseases in a companion animal, wherein the formulation is administered for at least 2 weeks.

In some embodiments, the pioglitazone or a pharmaceutically acceptable salt thereof is pioglitazone hydrochloride. In some embodiments, the pioglitazone or the pharmaceutically acceptable salt thereof is administered at about 2 to 3 mg/kg/day. In some embodiments, the pioglitazone or the pharmaceutically acceptable salt thereof is administered at about 1 to 5 mg/kg/day. In some embodiments, the pioglitazone or the pharmaceutically acceptable salt thereof is administered at an amount of up to 10 mg/kg/day. In some embodiments, the formulation is administered once daily. In some embodiments, the formulation is administered for at least about 4 weeks. In some embodiments, the formulation is administered for at least about 12 weeks. In some embodiments, the formulation is administered for at least about 1 year. In some embodiments, the method comprises decreasing an insulin level in the companion animal. In some embodiments, the insulin level is decreased by at least 5%. In some embodiments, the formulation improves insulin sensitivity. In some embodiments, the insulin sensitivity is measured by an oral glucose tolerance testing assay or by a hyperinsulinemic euglycemic clamp testing assay. In some embodiments, the insulin sensitivity is measured by a shortened or modified oral glucose tolerance testing assay. In some embodiments, the insulin sensitivity is measured by using fasting insulin blood levels. In some embodiments, the formulation decreases a triglyceride level in the companion animal. In some embodiments, the formulation decreases a cholesterol level in the companion animal. In some embodiments, the use further comprises mitigating an age-induced elevation of fatty acid, wherein the fatty acid is aggregated free fatty acids, saturated fatty acids, palmitic acid, linoleic acid, or oleic acid, or any combination thereof. In some embodiments, the companion animal is a dog. In some embodiments, the companion animal is at least 7 years old. In some embodiments, the companion animal is at least 10 years old. In some embodiments, the companion animal is at least 14 pounds. In some embodiments, the formulation comprises about 5% to about 15% of the pioglitazone or the pharmaceutically acceptable salt thereof. In some embodiments, the formulation comprises about 4 mg to about 85 mg of the pioglitazone or the pharmaceutically acceptable salt thereof. In some embodiments, the formulation is in a form of a tablet. In some embodiments, the tablet comprises 18 mg, 54 mg, or 81 mg of the pioglitazone or the pharmaceutically acceptable salt thereof.

In some embodiments, provided herein is a method for reducing or delaying mortality due to age-associated diseases in a companion animal in need thereof, comprising orally administering to the companion animal a therapeutically effective amount of a formulation comprising pioglitazone or a pharmaceutically acceptable salt thereof, wherein the formulation is administered for at least 2 weeks.

In some embodiments, In some embodiments, the pioglitazone or a pharmaceutically acceptable salt thereof is pioglitazone hydrochloride. In some embodiments, the pioglitazone or the pharmaceutically acceptable salt thereof is administered at about 2 to 3 mg/kg/day. In some embodiments, the pioglitazone or the pharmaceutically acceptable salt thereof is administered at about 1 to 5 mg/kg/day. In some embodiments, the pioglitazone or the pharmaceutically acceptable salt thereof is administered at an amount of up to 10 mg/kg/day. In some embodiments, the formulation is administered once daily. In some embodiments, the formulation is administered for at least about 4 weeks. In some embodiments, the formulation is administered for at least about 12 weeks. In some embodiments, the formulation is administered for at least about 1 year. In some embodiments, the method comprises decreasing an insulin level in the companion animal. In some embodiments, the insulin level is decreased by at least 5%. In some embodiments, the method improves insulin sensitivity. In some embodiments, the insulin sensitivity is measured by an oral glucose tolerance testing assay or by a hyperinsulinemic euglycemic clamp testing assay. In some embodiments, the insulin sensitivity is measured by a shortened or modified oral glucose tolerance testing assay. In some embodiments, the insulin sensitivity is measured by using fasting insulin blood levels. In some embodiments, the method decreases a triglyceride level in the companion animal. In some embodiments, the method decreases a cholesterol level in the companion animal. In some embodiments, the use further comprises mitigating an age-induced elevation of fatty acid, wherein the fatty acid is aggregated free fatty acids, saturated fatty acids, palmitic acid, linoleic acid, or oleic acid, or any combination thereof. In some embodiments, the companion animal is a dog. In some embodiments, the companion animal is at least 7 years old. In some embodiments, the companion animal is at least 10 years old. In some embodiments, the companion animal is at least 14 pounds. In some embodiments, the formulation comprises about 5% to about 15% of the pioglitazone or the pharmaceutically acceptable salt thereof. In some embodiments, the formulation comprises about 4 mg to about 85 mg of the pioglitazone or the pharmaceutically acceptable salt thereof. In some embodiments, the formulation is in a form of a tablet. In some embodiments, the tablet comprises 18 mg, 54 mg, or 81 mg of the pioglitazone or the pharmaceutically acceptable salt thereof.

BRIEF DESCRIPTION

FIG. 1 illustrates blood insulin levels, calculated as the standardized natural-log(insulin), in relation to age in years. Points are colored based on weight groups: below 50 lbs, 50 lbs to 100 lbs, 100 lbs to 150 lbs, and above 150 lbs.

Figure 2A:
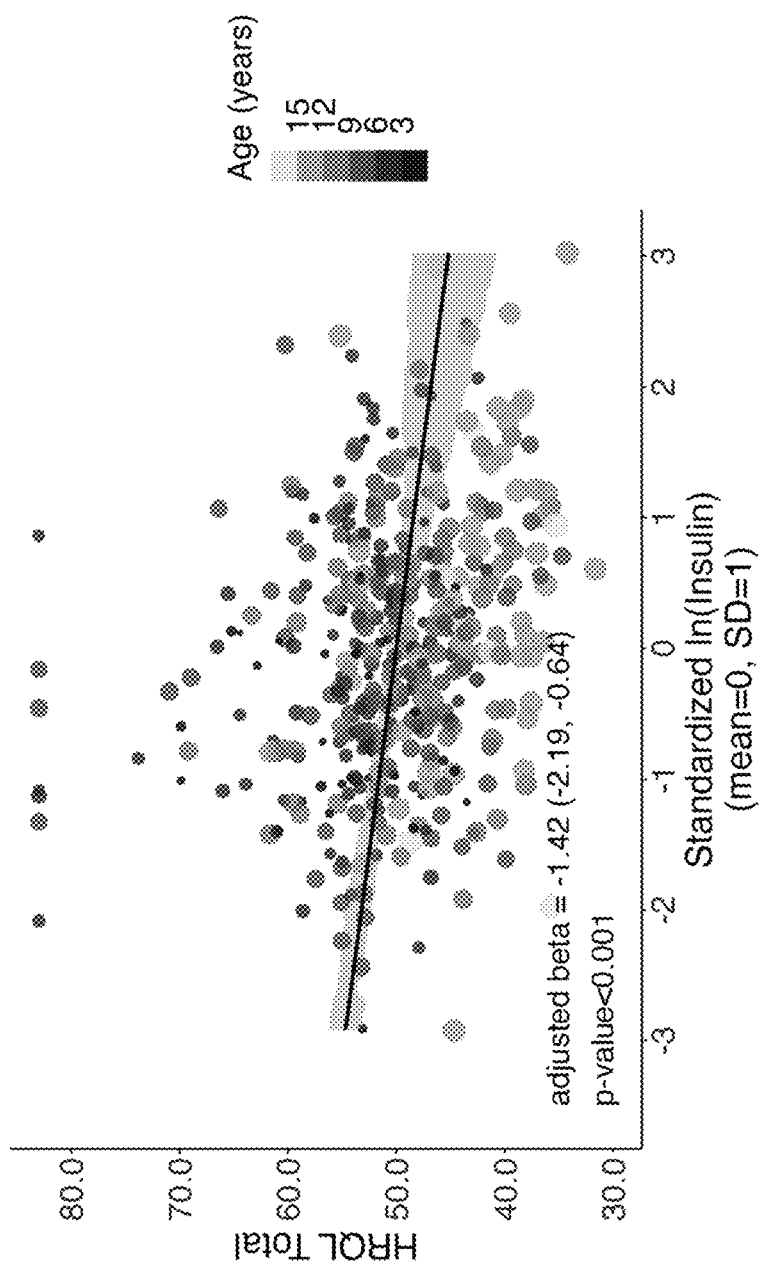
Figure 2B:
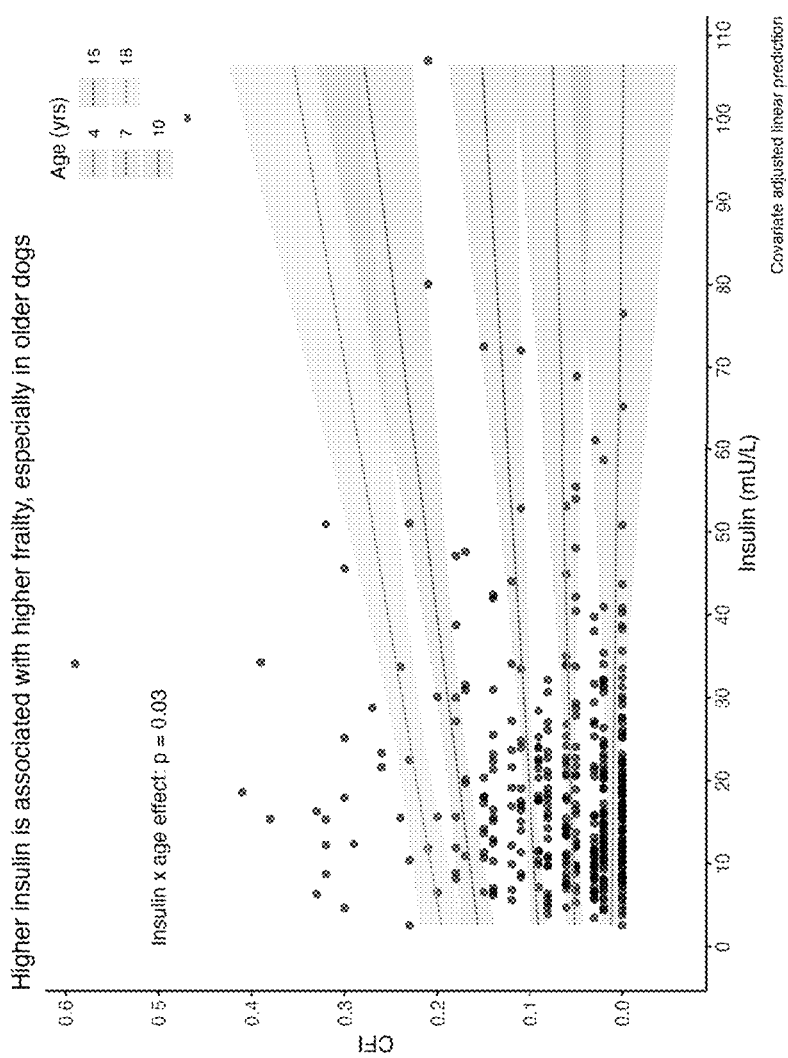

FIG. 2A-2B illustrates the HRQL total and Canine Frailty Score Index in relation to blood insulin levels. FIG. 2A illustrates HRQL total scores in relation to insulin levels, calculated as standardized natural-log(insulin). Points are colored based on age groups: below 3 yrs of age, 3 yrs to 6 yrs of age, 6 yrs to 9 yrs of age, 9 yrs to 12 yrs of age, 12 yrs to 15 yrs of age, and above 15 yrs of age. FIG. 2B illustrates Canine Frailty Score in relation to insulin, on its natural scale (mIU/L), for each age in years: 4, 7, 10, 15, 18 with 4 being the lower band line and progressing up to 18 being the higher band line.

Figure 3A:
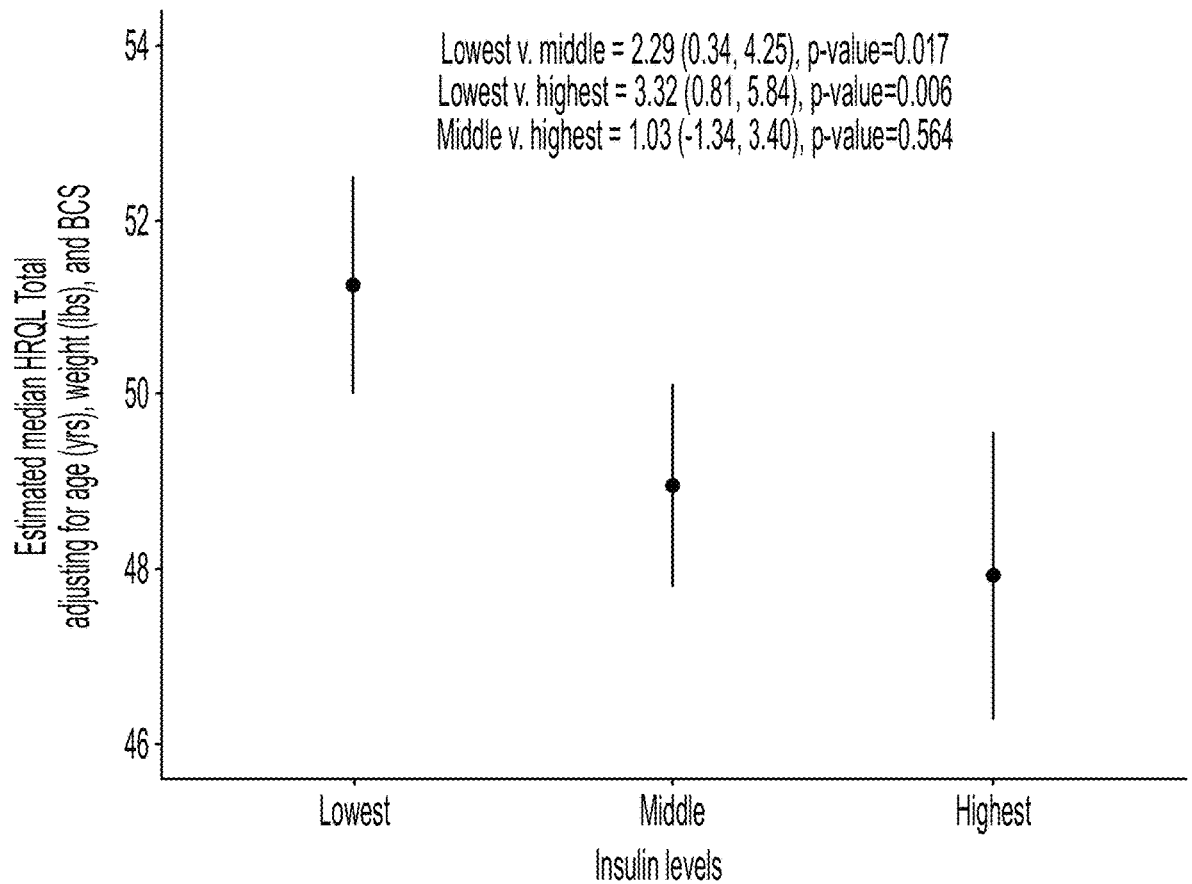
Figure 3B:
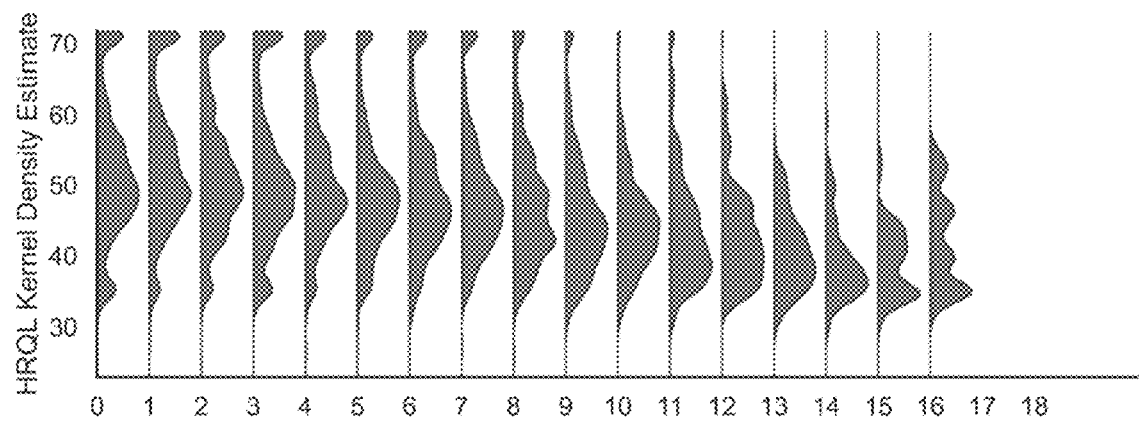
Figure 3C:
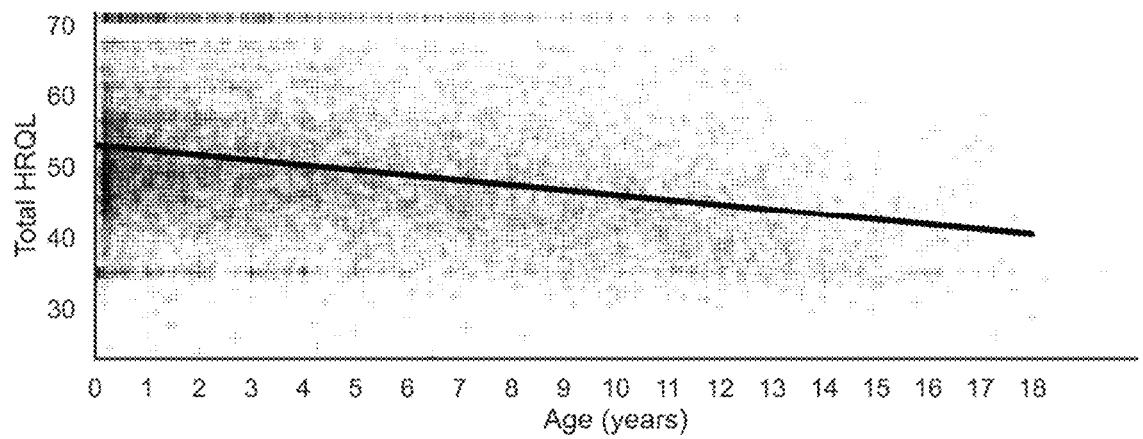

FIG. 3A-3C illustrate HRQL scores over time and for various groups. FIG. 3A illustrates the estimated medial HRQL score total adjusting for age in yrs, weight in lbs, and BCS for different groups of insulin levels. The Lowest group was categorized as insulin levels of 2.53 mU/L to 12 mU/L, the Middle group was categorized as insulin levels of 12 mU/L to 20.9 mU/L, and Highest group was categorized as insulin levels of 20.9 mU/L to 107 mU/L. FIG. 3B illustrates the HRQL Kernel Density Estimate on the Davies scale as a function of age in yrs. FIG. 3C illustrates total HRQL scores and age in yrs.

Figure 4A:
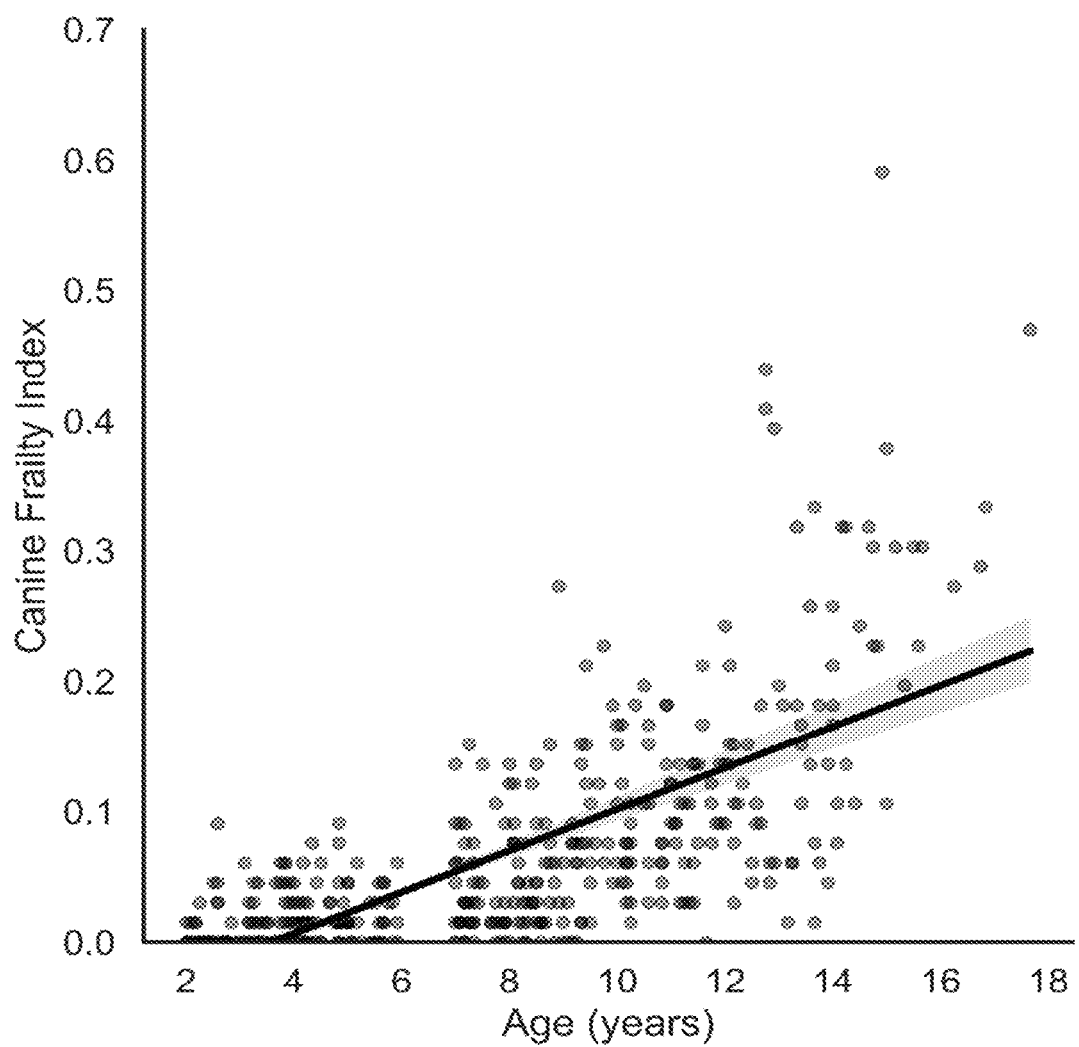
Figure 4B:
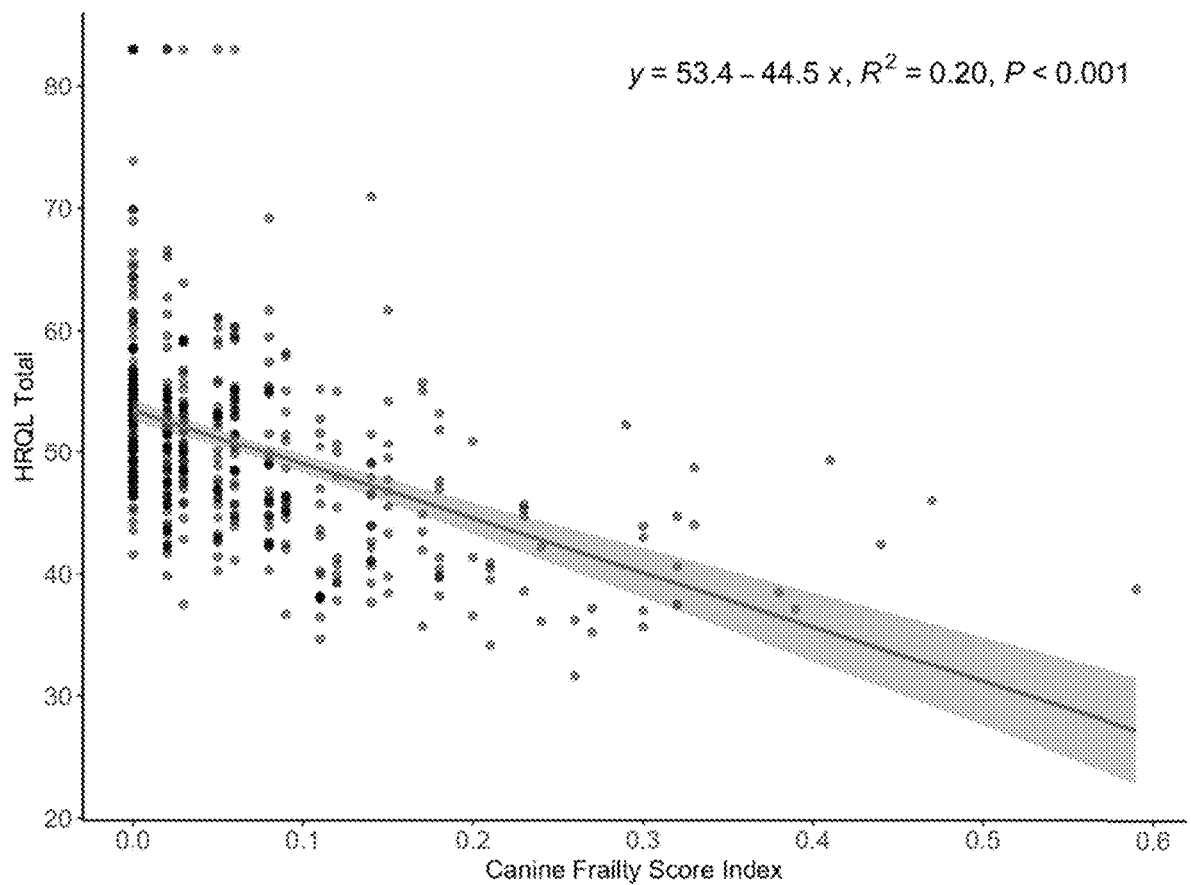
Figure 4C:
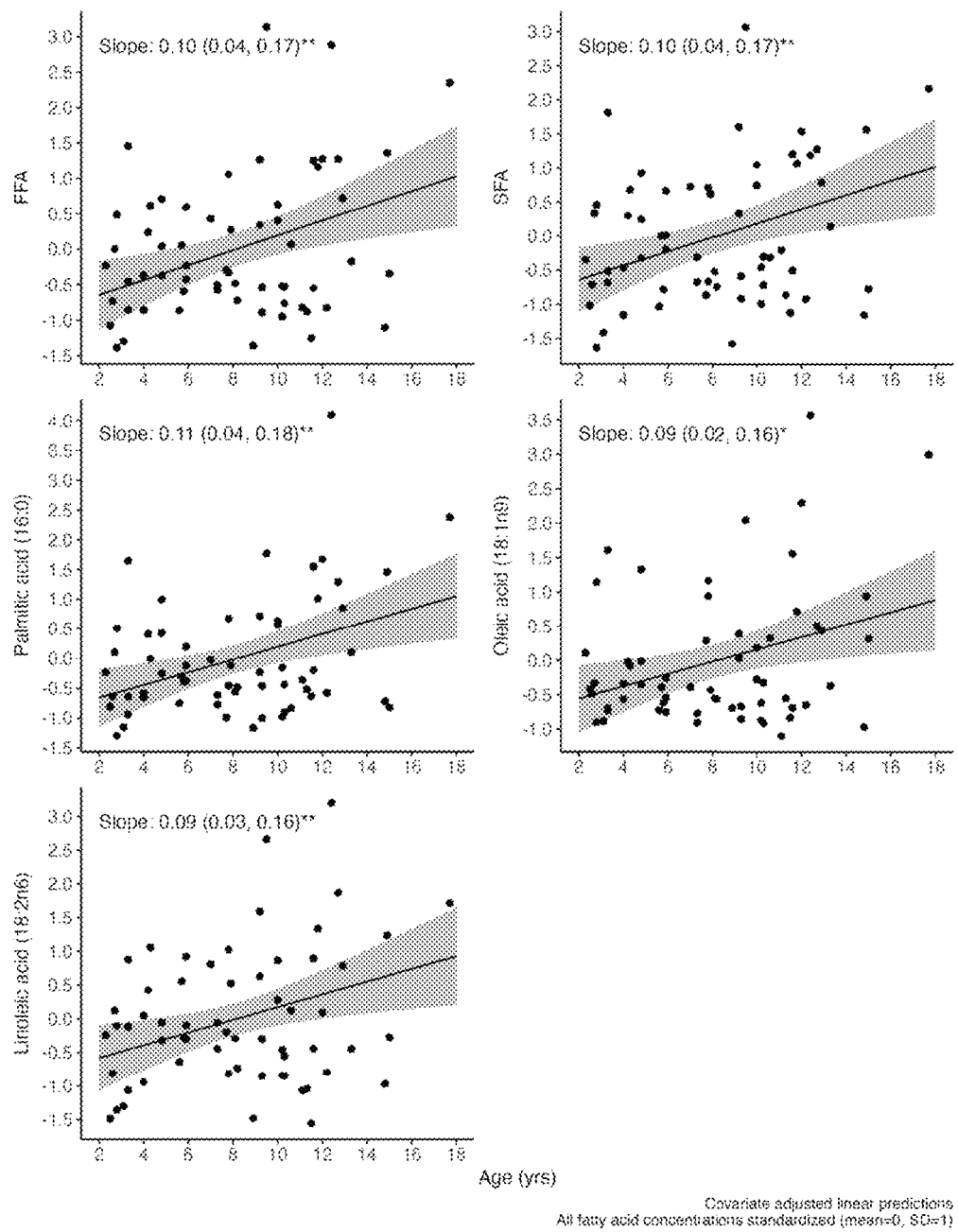
Figure 4D:
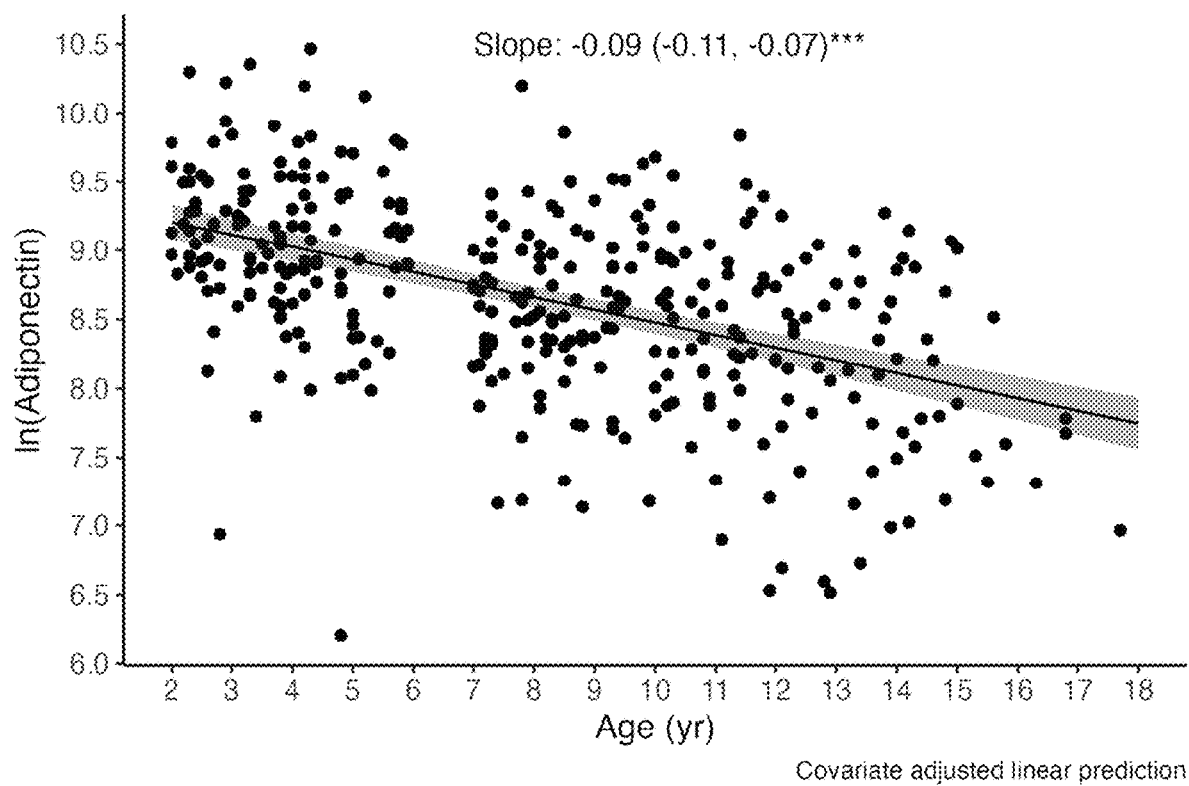
Figure 4E:
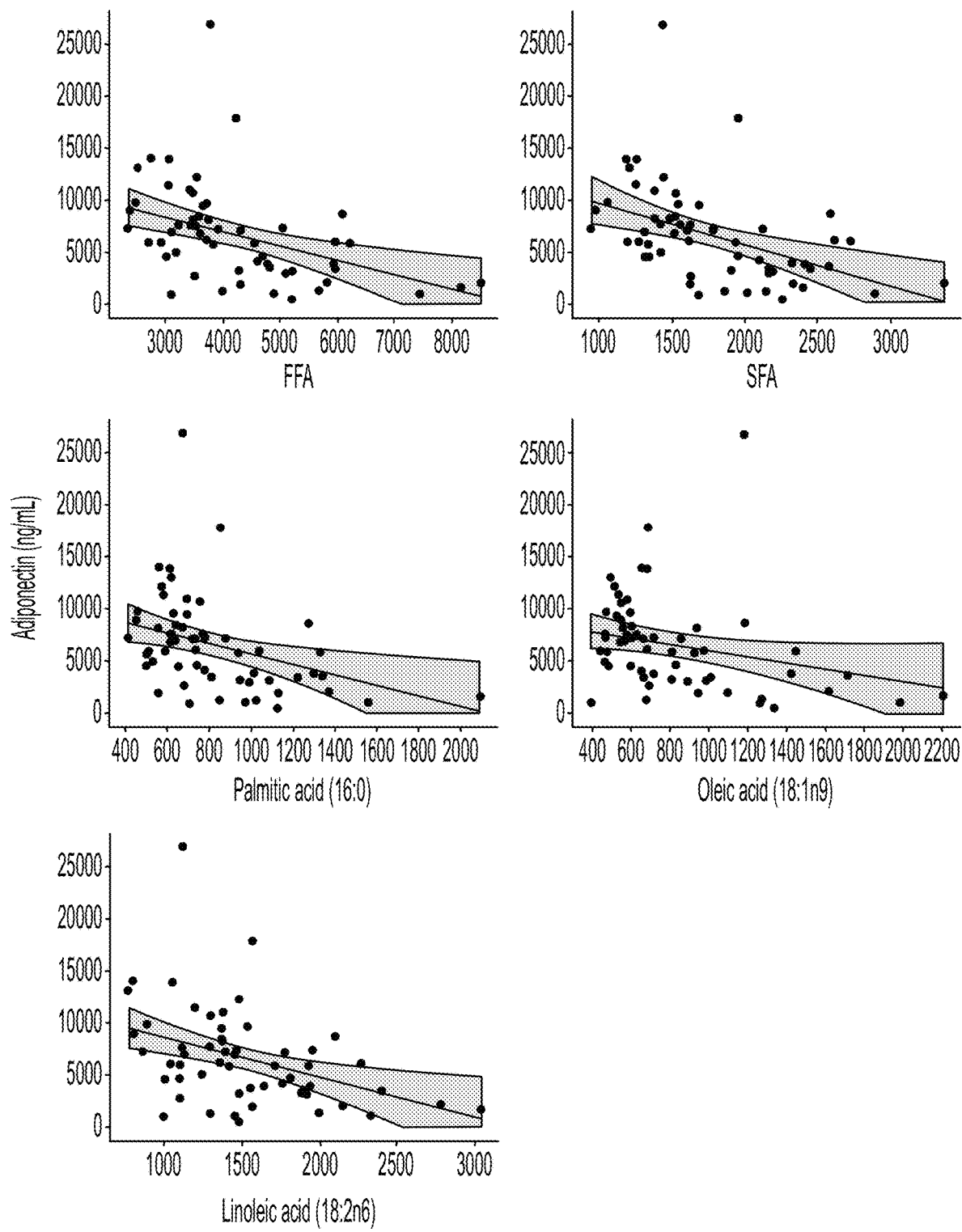
Figure 4F:
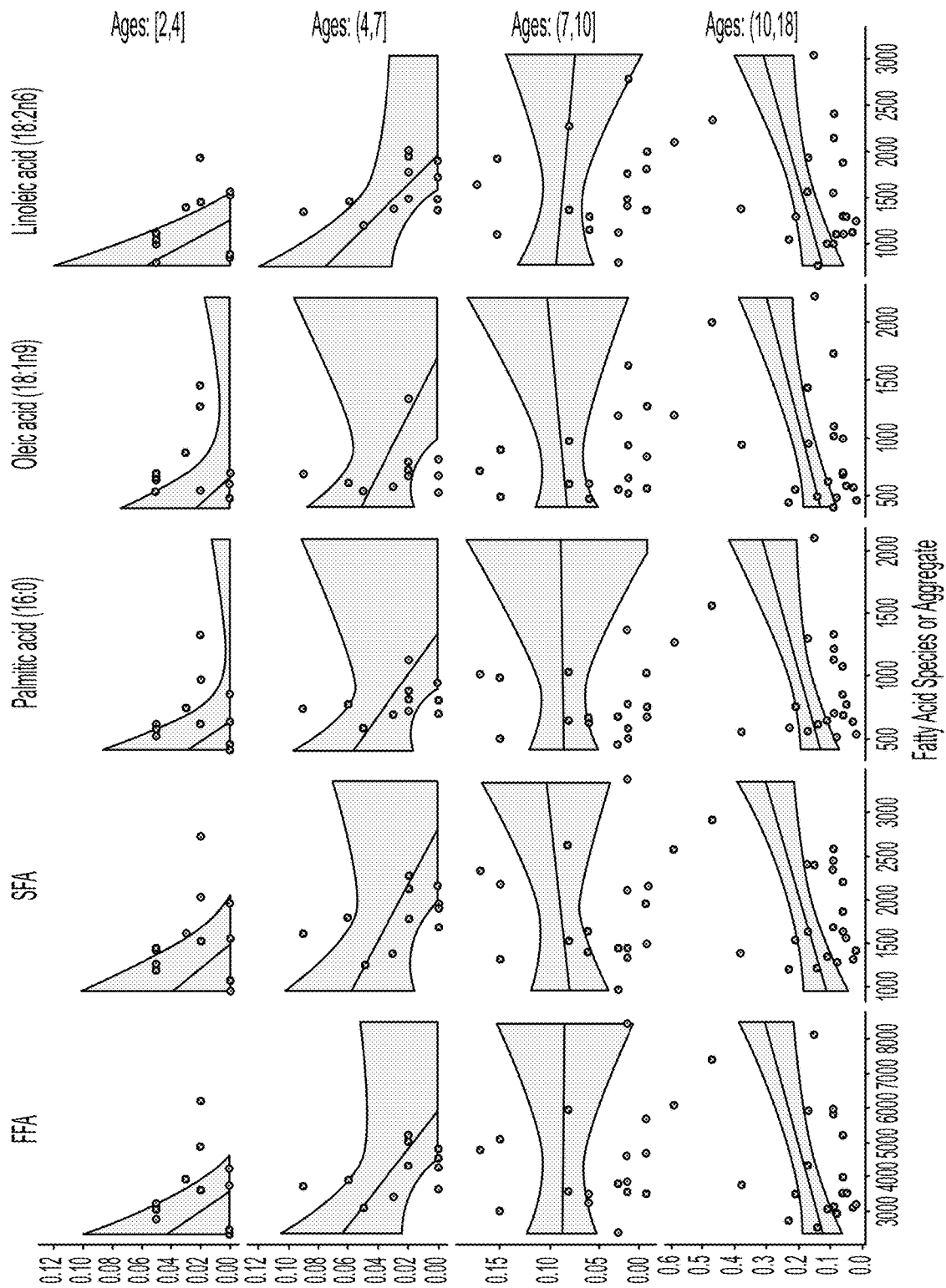
Figure 4G:
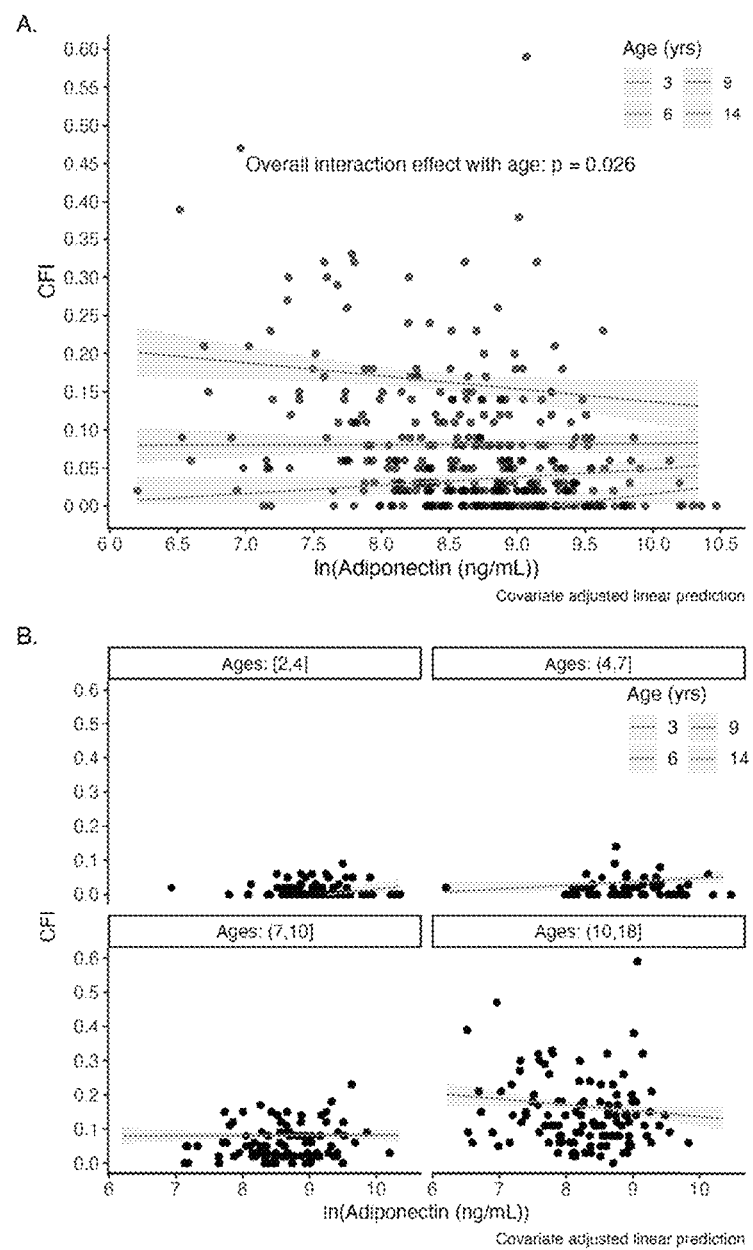

FIG. 4A-4G illustrate CFI and HRQL scores. FIG. 4A illustrates relationship between CFI score and age in yrs with linear regression analysis. FIG. 4B illustrates relationship between HRQL score and CFI score with linear regression analysis. FIG. 4C illustrates fatty acid species and aggregates in relation to age, using linear regression analysis. FIG. 4D. Illustrates relationship between natural-log (adiponectin) and age with linear regression analysis. FIG. 4E illustrates fatty acid species and aggregates in relation to adiponectin with linear regression analysis. FIG. 4F illustrates fatty acid species and aggregates in relation to CFI score within age groups with linear regression analysis. FIG. 4G illustrates relationship between natural-log(adiponectin) and CFI within age groups with linear regression analysis.

Figure 5A:
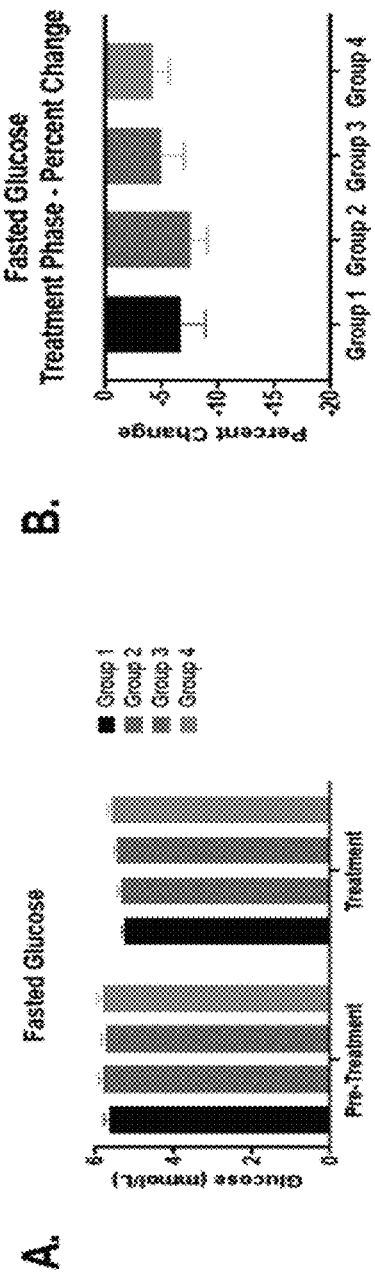
Figure 5B:
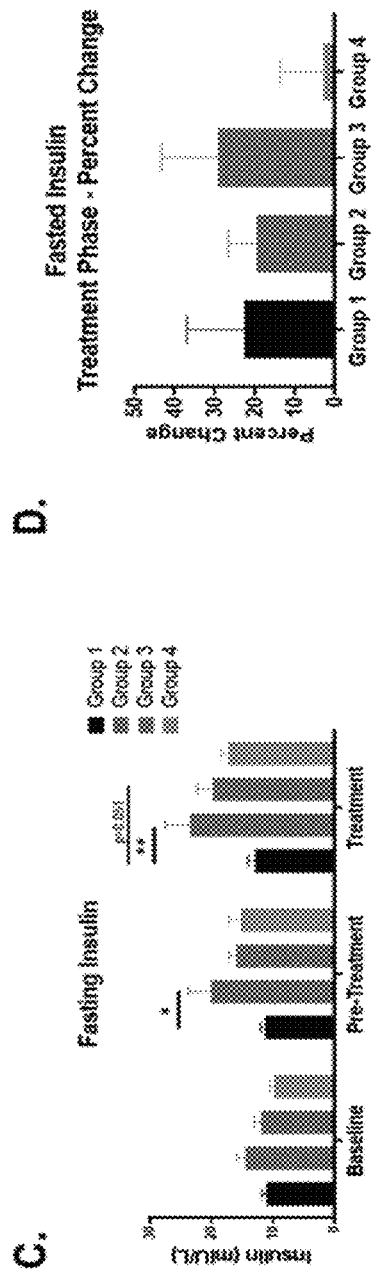
Figure 5C:
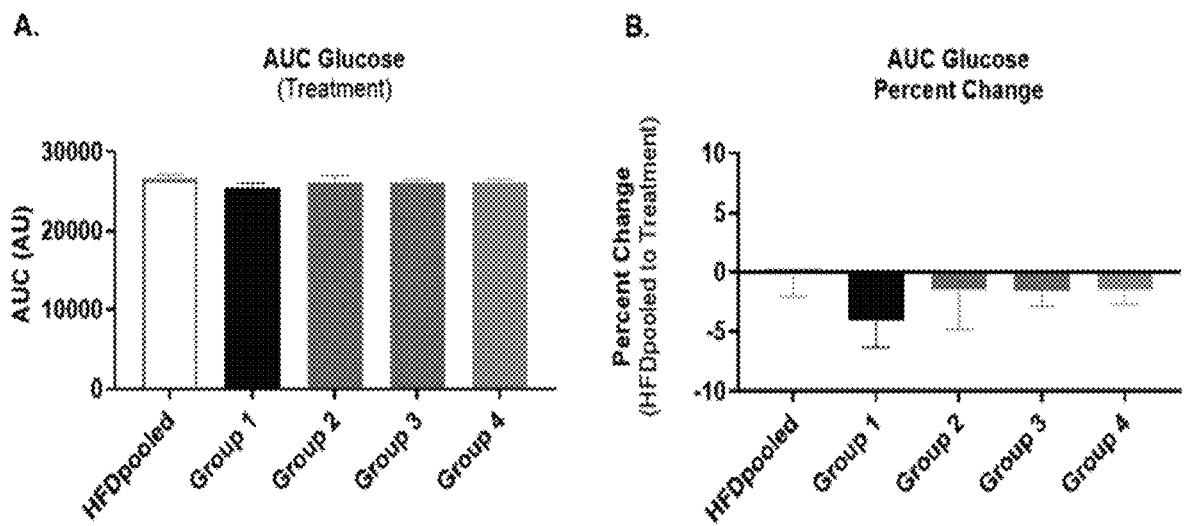
Figure 5D:
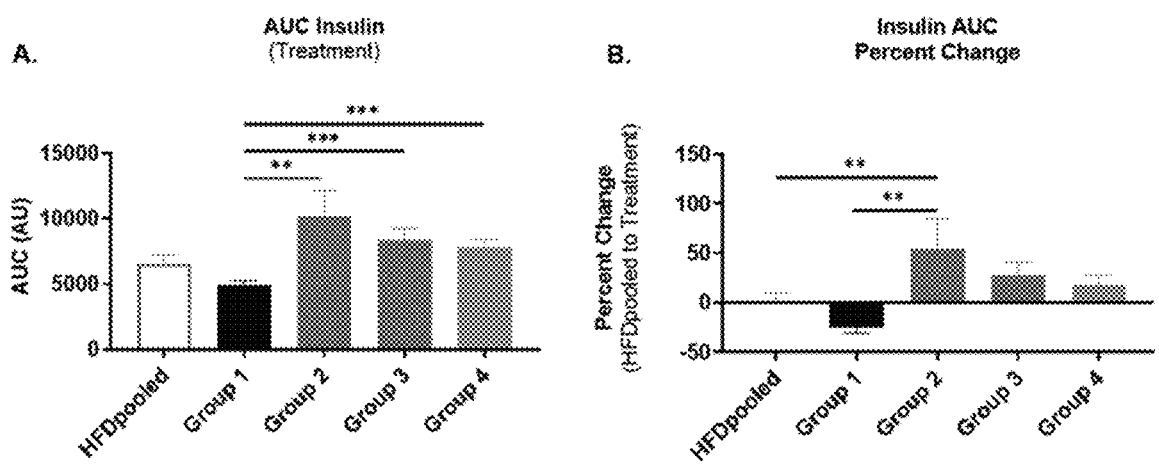

FIG. 5A-5D illustrate the glucose and insulin levels. Group 1 refers to normal diet+placebo, Group 2 refers to high-fat diet+placebo, Group 3 refers to high-fat diet+1 mg/kg of pioglitazone, and Group 4 refers to high-fat diet+2 mg/kg of pioglitazone. FIG. 5A illustrates the fasted glucose amount at pre-treatment and then treatment in graph A and also the percentage change in graph B. FIG. 5B illustrates the fasting insulin amount in graph C, and also the percentage change in graph D. FIG. 5C illustrates the AUC of glucose in graph A, and the percentage change in graph B. FIG. 5D illustrates the AUC of insulin in graph A, and the percentage change in graph B.

Figure 6A:
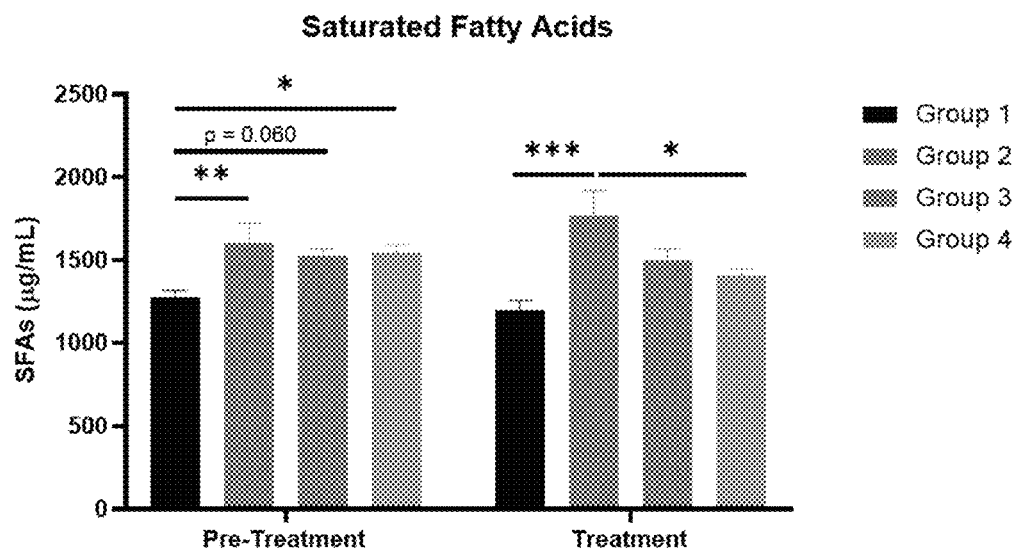
Figure 6B:
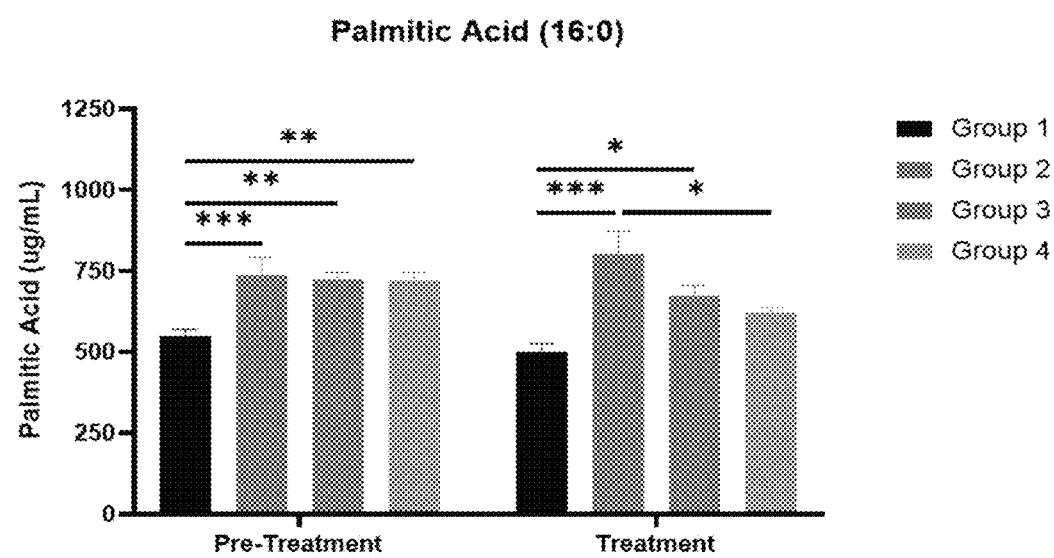
Figure 6C:
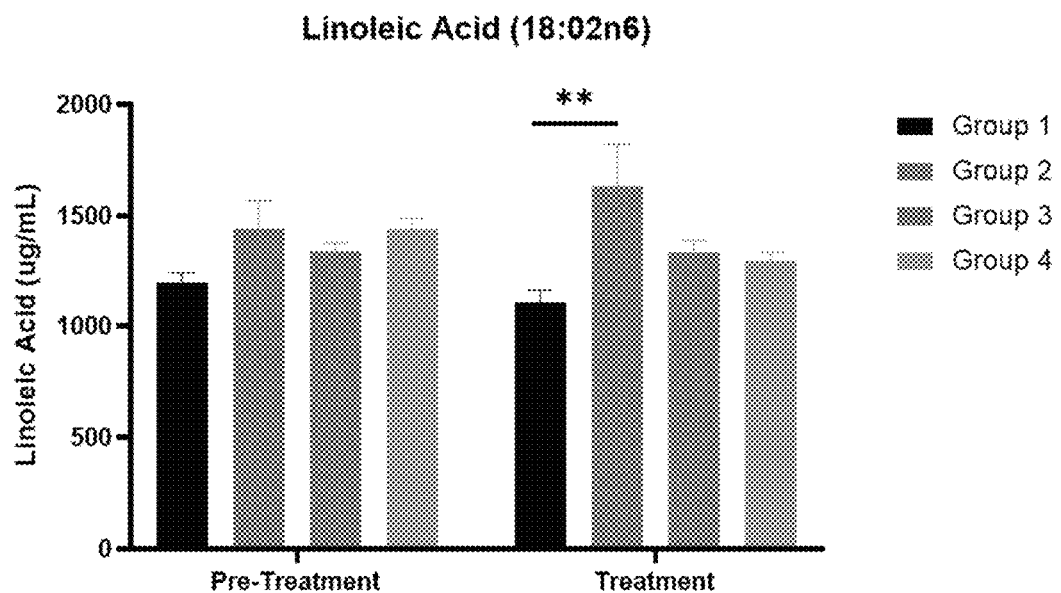
Figure 6D:
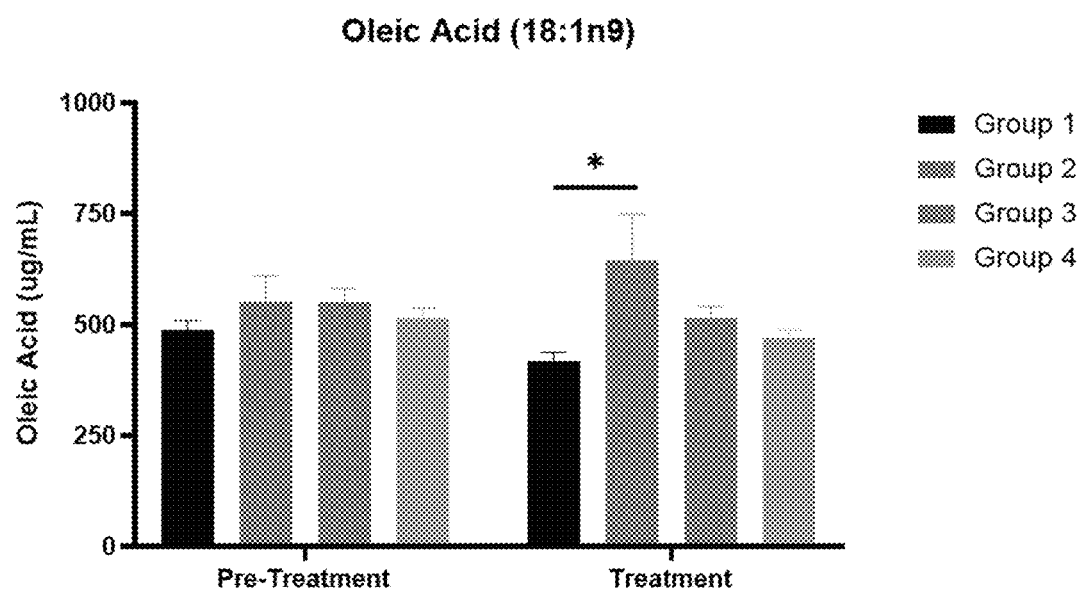
Figure 6E:
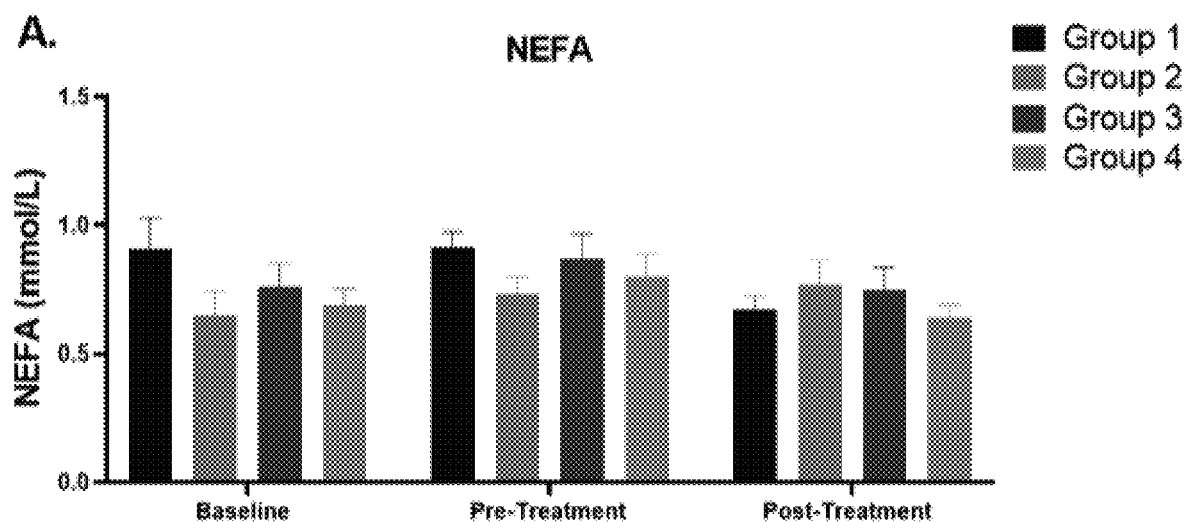
Figure 6F:
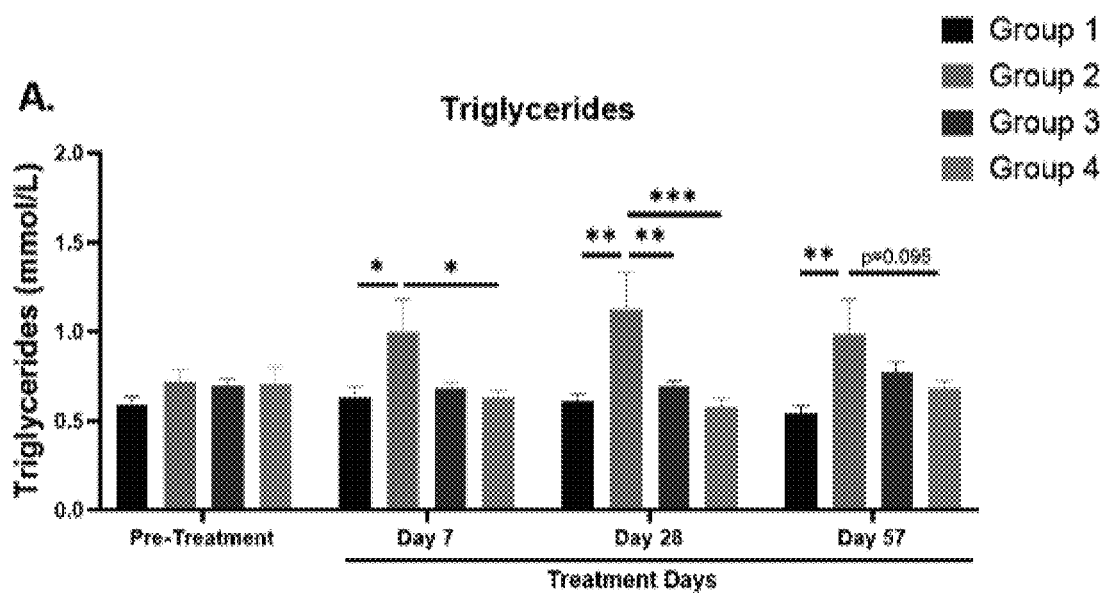
Figure 6G:
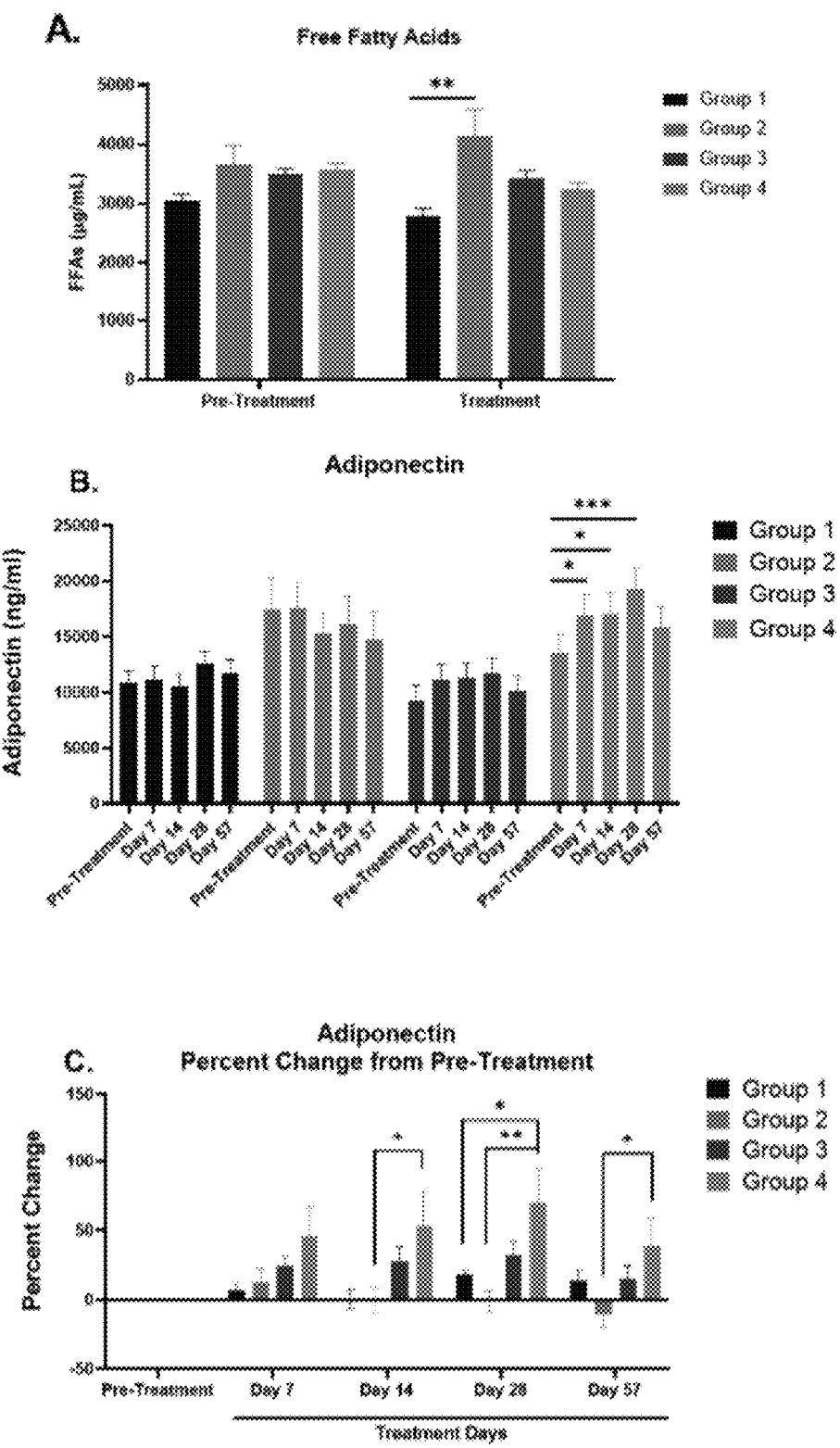

FIG. 6A-6E illustrate the quantify the fatty acids with different group treatments. Group 1 refers to normal diet+ placebo, Group 2 refers to high-fat diet+placebo, Group 3 refers to high-fat diet+1 mg/kg of pioglitazone, and Group 4 refers to high-fat diet+2 mg/kg of pioglitazone. FIG. 6A illustrates the fatty acid levels for saturated fatty acids. FIG. 6B illustrates the fatty acids levels for palmitic acid. FIG. 6C illustrates the fatty acid levels for linoleic acid. FIG. 6D illustrates the fatty acid levels for oleic acid. FIG. 6E illustrates clinical diagnostic assay NEFA are not sensitive enough to detect changes that are physiologically relevant. FIG. 6F. Illustrates the clinically measured triglyceride levels. FIG. 6G illustrates the free fatty acids and adiponectin levels of different cohorts, with the Group 1, 2, 3, and 4 bars going from left to right.

Figure 7:
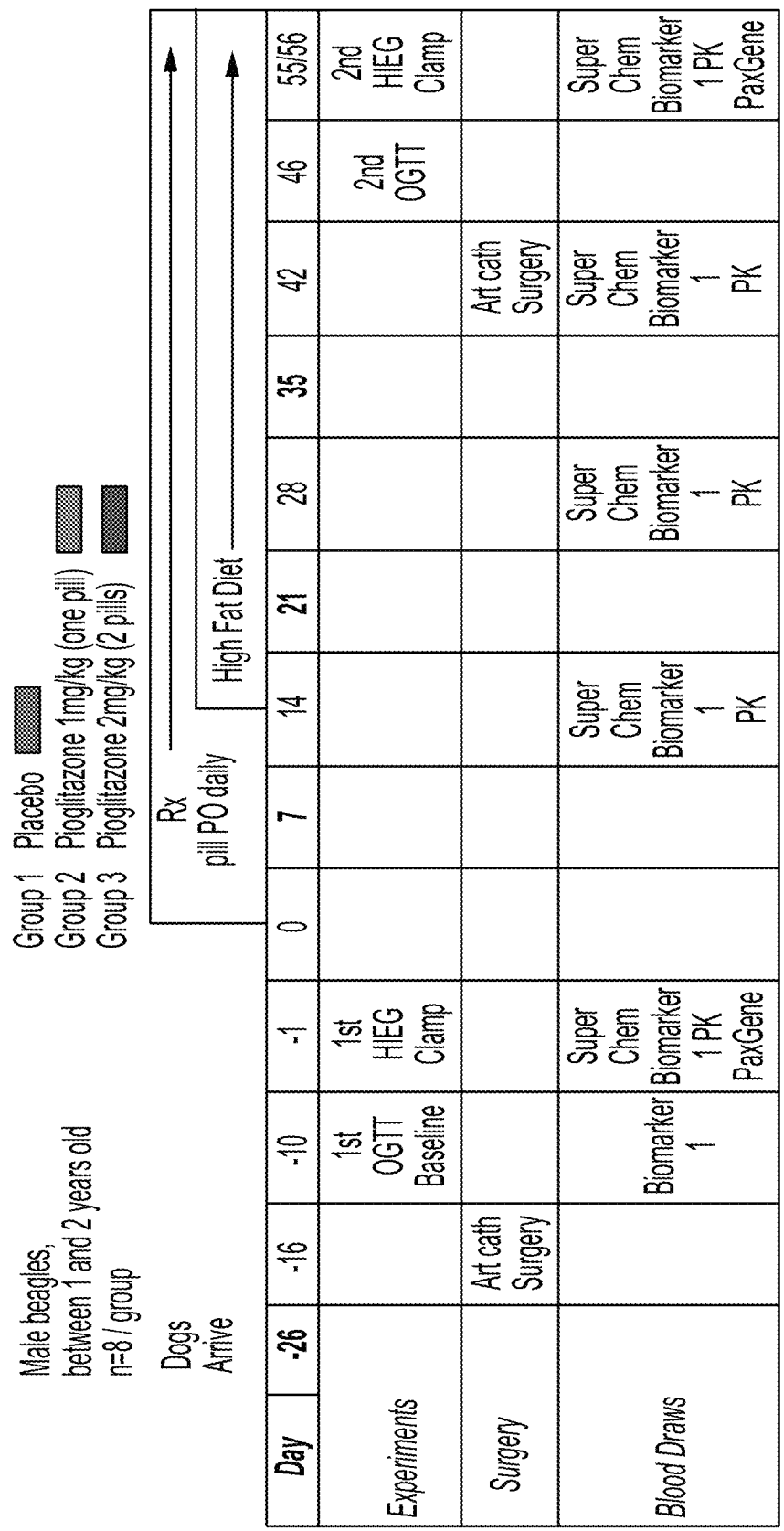

FIG. 7: Illustrates the study design for FIG. 8-10.

Figure 8A:
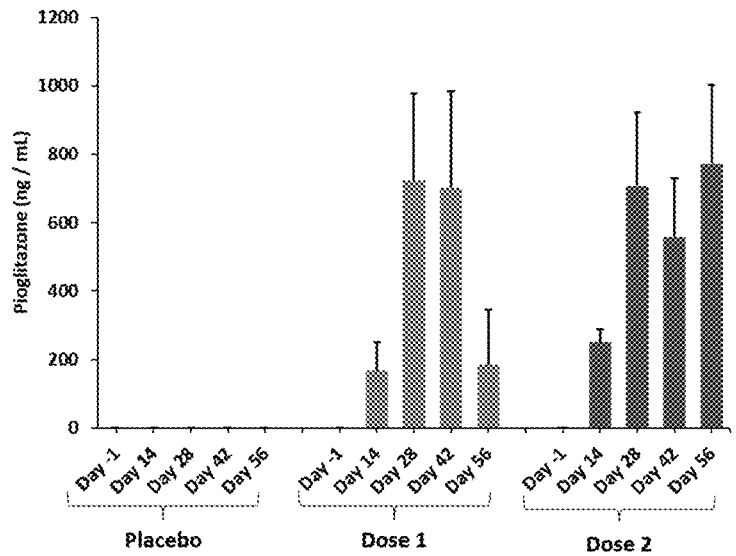
Figure 8B:
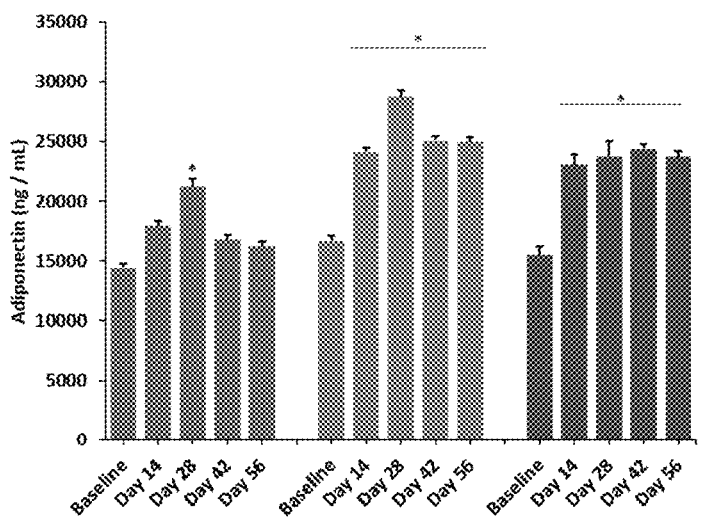

FIG. 8A-8B: Illustrates pioglitazone (A) and adiponectin (B) levels in placebo, pioglitazone 1 mg/kg and pioglitazone 2 mg/kg in dogs over the 56 days of the experimental protocol when dosed 2 weeks prior to high fat diet. All data presented as mean±SEM.

Figure 9A:
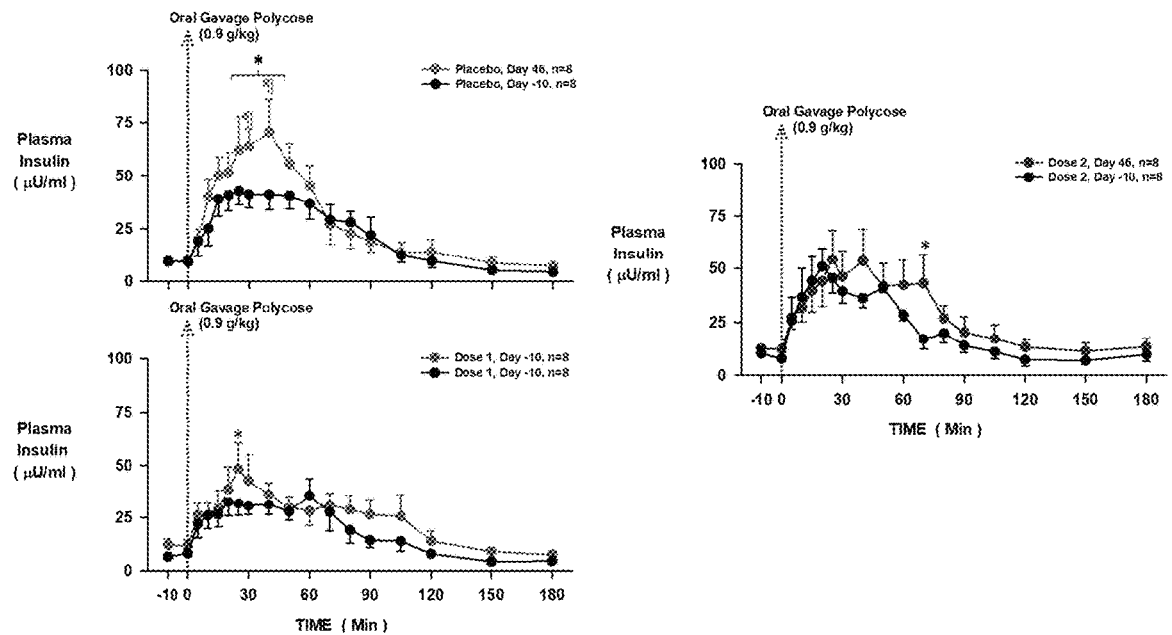
Figure 9B:
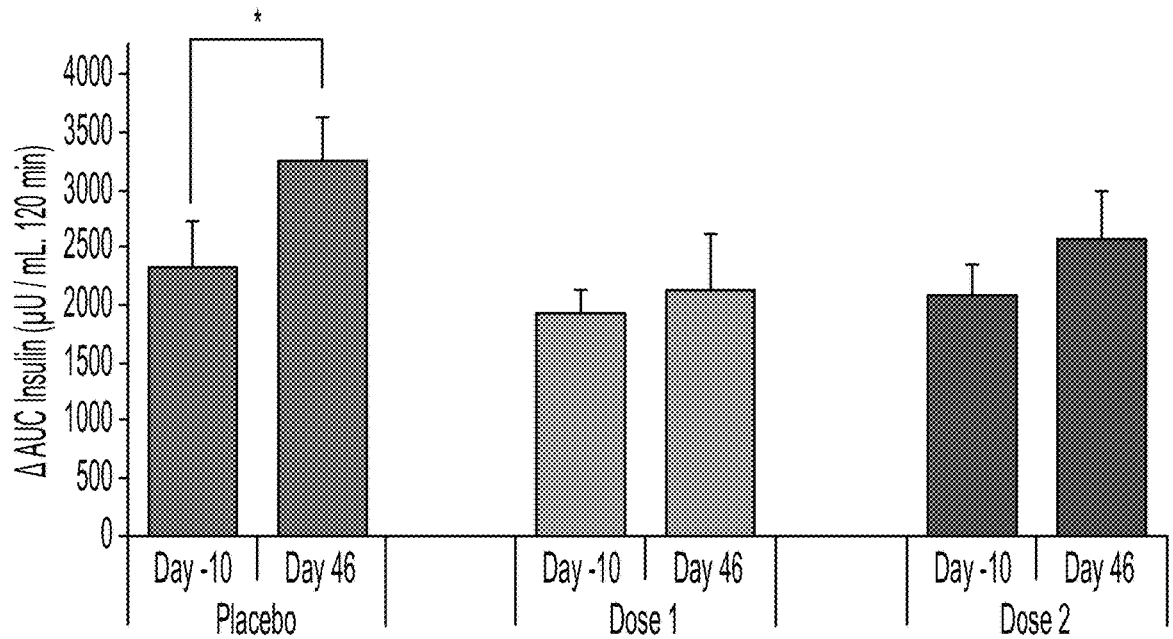

FIG. 9A-9B: Illustrates the OGTT insulin curves (FIG. 9A) and total 120 minute insulin AUC (FIG. 9B) at baseline and Day 46. All data presented as mean±SEM.

Figure 10A:
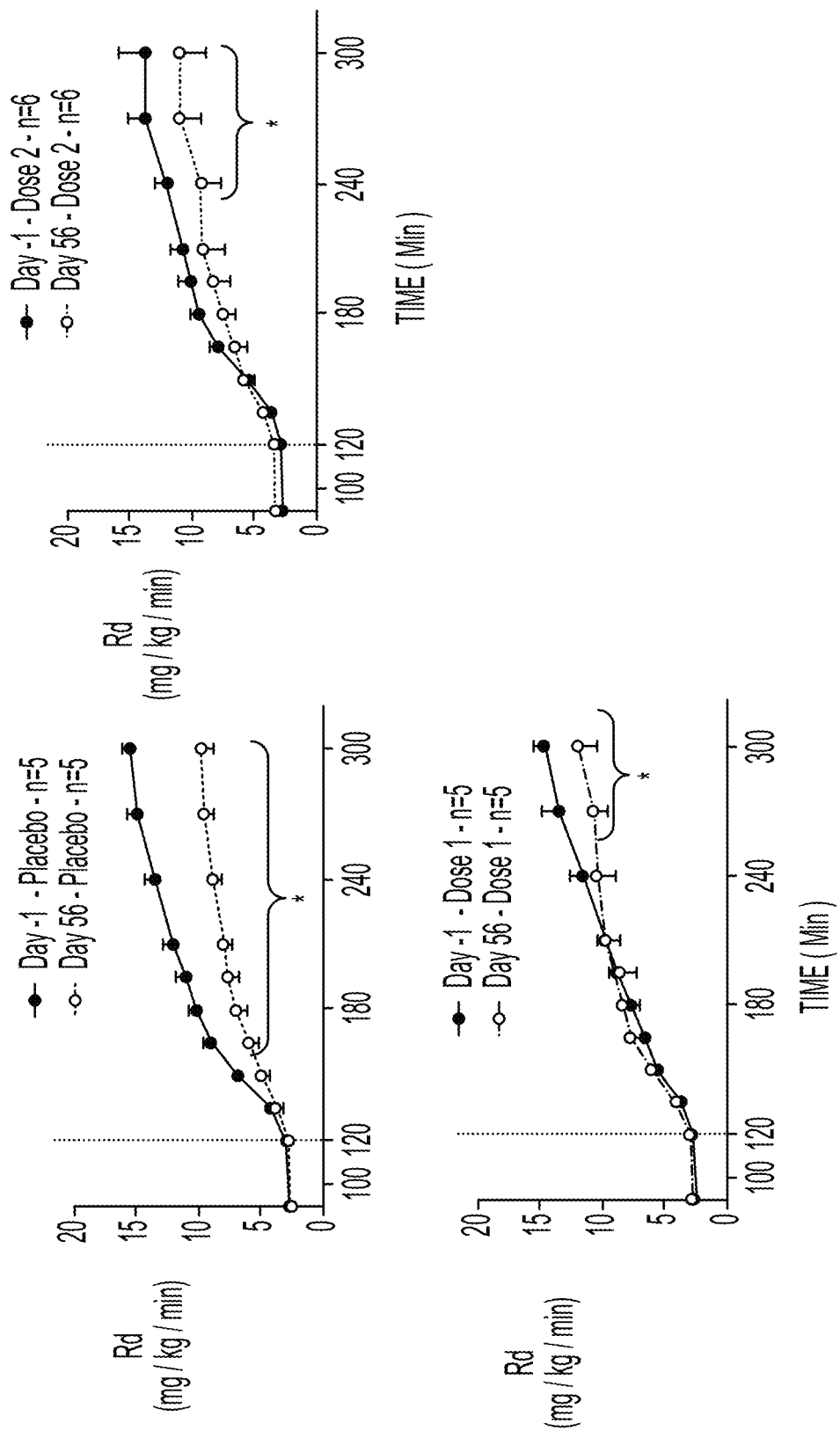
Figure 10B:
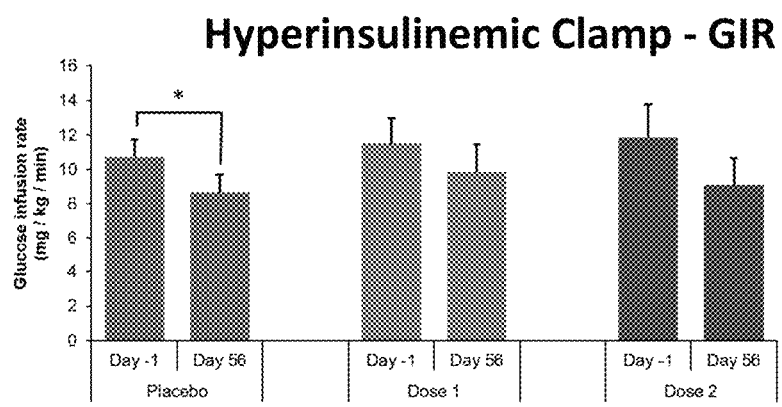
Figure 10C:
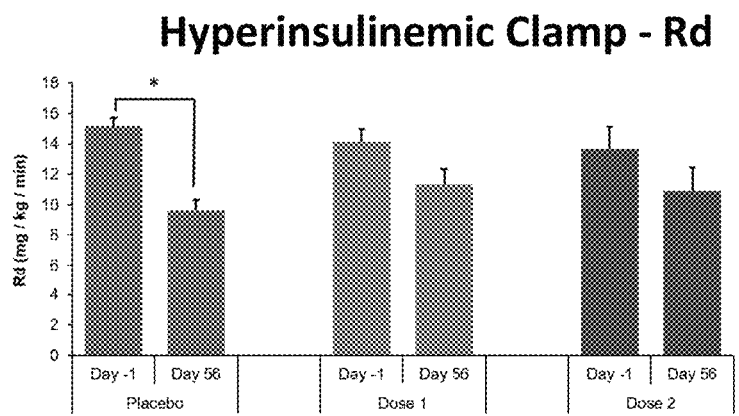

FIG. 10A-10C: Illustrates HIEG rate of glucose disappearance curves (Rd, FIG. 10A), HIEG rate of glucose disappearance AUC (FIG. 10B) and HIEG glucose infusion rate (GIR, FIG. 10C) in placebo, pioglitazone 1 mg/kg and pioglitazone 2 mg/kg in dogs over the 56 days of the experimental protocol. All data presented as mean±SEM.

Figure 11A:
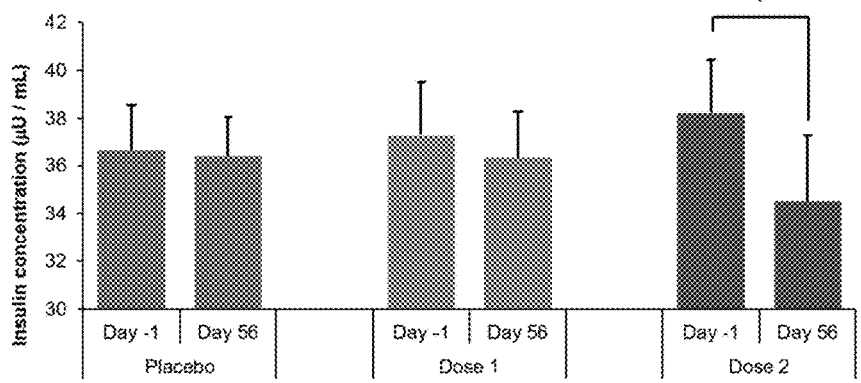
Figure 11B:
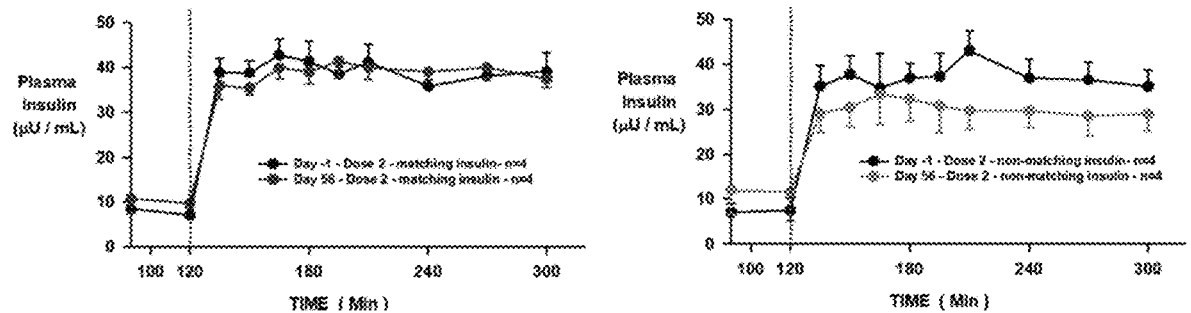
Figure 11C:
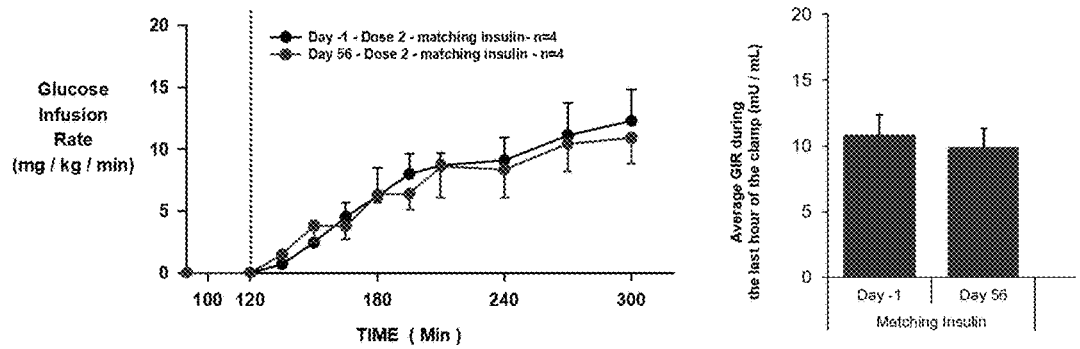

FIG. 11A-11C: (A) Illustrates the infused insulin levels during the HIEG clamp at baseline and Day 56. FIG. 11B illustrates that infused insulin rates between dogs in the pioglitazone 2 mg/kg group. FIG. 11C illustrates the GIR in animals with matched infused insulin in the HIEG clamp. All data presented as mean±SEM.

Figure 12A:
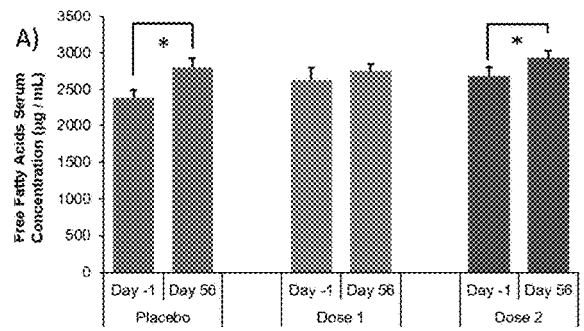
Figure 12B:
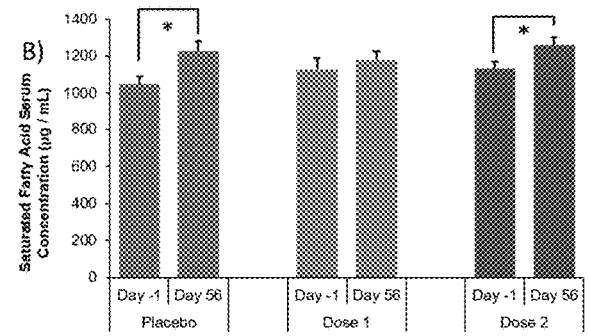
Figure 12C:
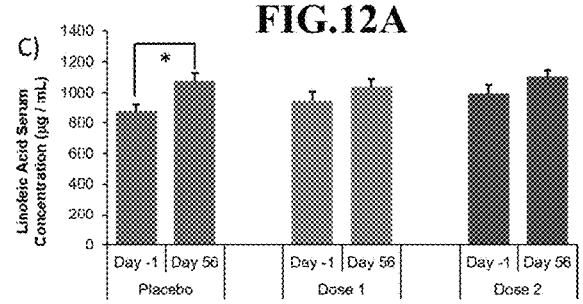
Figure 12D:
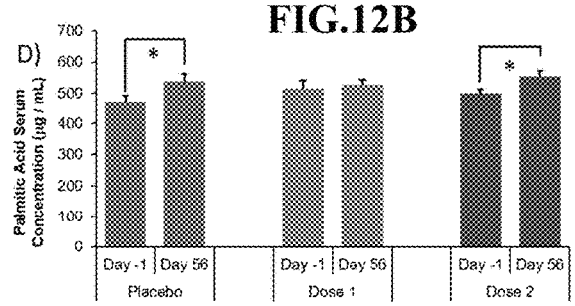
Figure 12E:
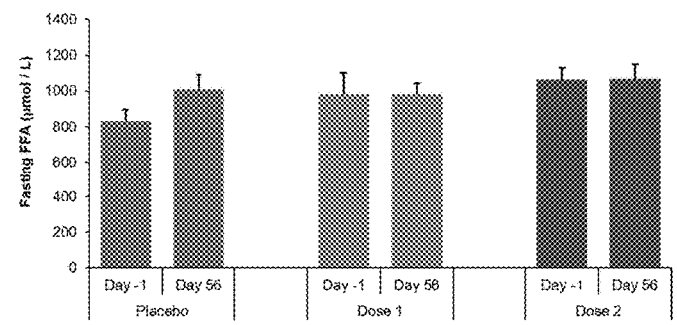

FIG. 12A-12E: FIG. 12A Illustrates the free fatty acid concentrations quantified by GC-MS at baseline and Day 56 FIG. 12B Illustrates the saturated fatty acid concentrations quantified by GC-MS at baseline and Day 56 FIG. 12C Illustrates the linoleic fatty acid concentrations quantified by GC-MS at baseline and Day 56. FIG. 12D Illustrates the palmitic fatty acid concentrations quantified by GC-MS at baseline and Day 56. FIG. 12E Illustrates the free fatty acid concentrations quantified by clinically utilized NEFA assay at baseline and Day 56 All data presented as mean±SEM.

DETAILED DESCRIPTION

Age-related changes in adipose tissue function impact many of the known mechanisms of biological aging. Increases in visceral adipose tissue with age, and decline in subcutaneous adipose, is a common observation in dogs, rodents, and humans. Insulin resistance increases concomitantly with age in all three species. The net result of this age-dependent metabolic dysfunction is reduced flexibility in utilizing nutrient fuel sources, organ dysfunction, and an increase in physical frailty. Increased frailty also directly leads to a decrease in quality of life. As a master regulator of adipose tissue, PPARγ is uniquely positioned to impact age-dependent metabolic dysfunction. Agonists of PPARγ, like pioglitazone, have been demonstrated to improve lipid handling, improve insulin sensitivity, and restore adipose function in the context of obesity and T2DM. Given the profound benefits that have been observed with pioglitazone in treating and preventing metabolic diseases, such benefits should also apply to age-related metabolic dysfunction. Delaying or preventing age-related metabolic dysfunction through PPAR γ agonism reduces frailty and prolongs healthy lifespan and life expectancy.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The term "about" when referring to a number or a numerical range means that the number or numerical range referred to is an approximation within experimental variability (or within statistical experimental error), and thus the number or numerical range varies no more than 15% of the stated number or numerical range. The terms "treat", "treating" and "treatment" refers to any indicia of success in the treatment or amelioration of an injury, pathology, condition, or symptom (e.g., pain), including any objective or subjective parameter such as abatement; remission; mitigating, reversing, or diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter including, e.g., the result of a physical examination. The terms "formulation" and "composition," as used herein, are used interchangeably and refer to a mixture of two or more compounds, elements, or molecules. In some aspects the terms "formulation" and "composition" may be used to refer to a mixture of one or more active agents with a carrier or other excipients.

The term "fat" or "fats" as used herein, refers to dietary fats. This refers to fatty acids, esters of fatty acids, and mixtures of both fatty acids and esters of fatty acids. It can also refer to glycerides such as but not limited to diglycerides and triglycerides, lipids, such as but not limited to phospholipids, as well as sterols, such as but not limited to cholesterol. Fats can also refer to free fatty acids and fatty acid conjugates.

The term "administering" as used herein, refers to oral administration, administration as a suppository, topical contact, parenteral, intravenous, intraperitoneal, intramuscular, intralesional, intranasal or subcutaneous administration, intrathecal administration, intra-lymphatic, inhalation of microdroplets, or the implantation of a slow-release device e.g., a mini-osmotic pump, to the subject.

The terms "effective amount" or "therapeutically effective amount" as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The term "pharmaceutically acceptable salt" in reference to PPARγ agonist, which does not cause significant irritation to a mammal to which it is administered and does not substantially abrogate the biological activity and properties of the compound. A wide variety of pharmaceutically acceptable salts may be formed and include:

acid addition salts formed by reacting the PPARγ agonist with an organic acid, which includes aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, benzenesulfonic acid, p-toluenesulfonic acid, salicylic acid, and the like;

acid addition salts formed by reacting the PPARγ agonist with an inorganic acid, which includes hydrochloric acid, hydrobromic acid, sulfuric acid, nitric acid, phosphoric acid, hydroiodic acid, hydrofluoric acid, phosphorous acid, and the like.

The term "metabolic dysfunction" can refer to a state of imbalance in and/or decrease in metabolic function. In some embodiments, the metabolic dysfunction is caused by natural aging. In some embodiments, the metabolic dysfunction is caused by high fat diet feeding. In some embodiments, the metabolic dysfunction is caused by natural aging. In some embodiments, the metabolic dysfunction is caused by high fat diet feeding.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In some embodiments, the mammal is a human. In some embodiments, the mammal is a dog. In some embodiments, the mammal is a rodent. In some embodiments, the mammal is a companion animal.

The term "mitigating" refers to the reduction or elimination of one or more symptoms of or risk factors associated with a disease or condition, and/or a reduction in the rate or delay of onset or severity of one or more symptoms of the disease or condition. In some embodiments, the term "mitigating" can also refer to the prevention of that disease or condition. In some embodiments, the disease or condition is a metabolic dysfunction. Examples include the prophalactic effects on metabolic-dysfunction-induced increases in fasting insulin, free fatty acids and frailty.

The term "reversing" refers to the return of a particular biomarker or outcome back to clinically healthy levels. Examples include reversing the effects of metabolic-dysfunction-induced increases in fasting insulin, free fatty acids and frailty. In some embodiments, the metabolic dysfunction is caused by natural aging. In some embodiments, the metabolic dysfunction is caused by high fat diet feeding.

The section headings used herein are for organizational purposes only and are not to be construed as limiting the subject matter described.

Compounds

The compounds described herein can be PPARγ agonists, PPARα agonists, or PPARα/PPARγ agonists. The compounds described herein are PPARγ agonists. In some embodiments, the PPARγ agonist is a thiazolidinedione derivative. In some embodiments, the PPARγ agonist is lobeglitazone, troglitazone, ciglitazone, rivoglitazone, englitazone, balaglitazone, netoglitazone, pioglitazone, or rosiglitazone. In some embodiments, the PPARγ agonist is lobeglitazone, troglitazone, pioglitazone, or rosiglitazone. In some embodiments, the PPARγ agonist is pioglitazone. In some embodiments, the PPARγ agonist is pioglitazone or a salt thereof. In some embodiments, the pioglitazone is in a free base form.

In some embodiments, the PPARγ agonist is pioglitazone hydrochloride. In some embodiments, the PPARγ agonist is pioglitazone. Pioglitazone is a PPARγ agonist having the structure, shown as pioglitazone HCl:

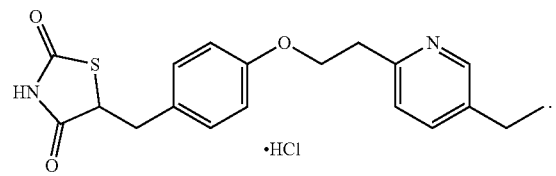 [SMILES: CCc1ccc(CCOc2ccc(CC3SC(=O)NC3=O)cc2)nc1 ; Cl]

In some embodiments, the PPARγ agonist is rosiglitazone. Rosiglitazone is a PPARγ agonist having the structure, shown as rosiglitazone maleate:

The compounds described herein are PPARα agonists. In some embodiments, the PPARα agonist is fenofibrate, clofibrate, pirinixic acid, WY1, GW735, GW409544, BMS631707, KRP101, AVE8134, or pioglitazone. In some embodiments, the compound can be a dual PPARα/PPARγ agonist.

In some embodiments, the pioglitazone or a salt thereof is administered in an amount of 1 mg/kg to 20 mg/kg. In some embodiments, the pioglitazone or a salt thereof is administered in an amount of 1 mg/kg to 10 mg/kg. In some embodiments, the pioglitazone or a salt thereof is administered in an amount of 1 mg/kg to 5 mg/kg. In some embodiments, the pioglitazone or a salt thereof is administered in an amount of 1 mg/kg. In some embodiments, the pioglitazone or a salt thereof is administered in an amount of 2 mg/kg. In some embodiments, the pioglitazone or a salt thereof is administered in an amount of about 0.1 to 5 mg/kg. In some embodiments, the pioglitazone or a salt thereof is administered in an amount of about 2 to 3 mg/kg. In some embodiments, the pioglitazone or a salt thereof is administered in an amount of about 1 to 3 mg/kg. In some embodiments, the pioglitazone or a salt thereof is administered in an amount of about 2 to 5 mg/kg. In some embodiments, the pioglitazone or a salt thereof is administered in an amount of about 5 to 10 mg/kg. In some embodiments, the pioglitazone or a salt thereof is administered in an amount of at least about 0.1 mg/kg, at least about 1 mg/kg, at least about 2 mg/kg, at least about 4 mg/kg, at least about 6 mg/kg, at least about 7 mg/kg, at least about 9 mg/kg, or at least about 10 mg/kg. In some embodiments, the pioglitazone or a salt thereof is administered in an amount of at most about 20 mg/kg, at most about 10 mg/kg, at most about 9 mg/kg, at most about 8 mg/kg, at most about 7 mg/kg, at most about 6 mg/kg, at most about 5 mg/kg, at most about 4 mg/kg, at most about 3 mg/kg, at most about 2 mg/kg, or at most about 1 mg/kg. In some embodiments, the pioglitazone or a salt thereof is administered enterally. In some embodiments, the pioglitazone or a salt thereof is administered orally. In some embodiments, the pioglitazone or a salt thereof is administered parenterally. In some embodiments, the pioglitazone or a salt thereof is administered multiple times a day, twice a day, daily, every other day, once a week, or once every two weeks. In some embodiments, the pioglitazone or a salt thereof is administered daily, every other day, once a week, or once every two weeks In some embodiments, the pioglitazone or a salt thereof is administered daily. In some embodiments, the pioglitazone or a salt thereof is administered at 1 mg/kg/day to 20 mg/kg/day. In some embodiments, the pioglitazone or a salt thereof is administered at 1 mg/kg/day to 10 mg/kg/day. In some embodiments, the pioglitazone or a salt thereof is administered at 1 mg/kg/day to 5 mg/kg/day. In some embodiments, the pioglitazone or a salt thereof is administered at 1 mg/kg/day. In some embodiments, the pioglitazone or a salt thereof is administered at 2 mg/kg/day.

Methods

In some embodiments, described herein is a method for mitigating or reversing insulin resistance in a mammal in need thereof, with or without evidence of metabolic dysfunction, comprising administering to the mammal a therapeutically effective amount of a formulation comprising a PPARγ agonist, or a pharmaceutically acceptable salt or prodrug thereof. In some embodiments, described herein is a method for mitigating or reversing insulin resistance in a mammal in need thereof, comprising administering to the mammal a therapeutically effective amount of a formulation comprising a PPARγ agonist, or a free base or a pharmaceutically acceptable salt or prodrug thereof.

In some embodiments described herein is a method for delaying development in aging-associated insulin resistance in a mammal in need thereof, comprising administering to the mammal a therapeutically effective amount of a formulation comprising a PPARγ agonist, or a pharmaceutically acceptable salt or prodrug thereof.

In some embodiments, described herein is a method of method of maintaining healthy functioning of adipose tissue in a mammal in need thereof, comprising administering to the mammal a therapeutically effective amount of a formulation comprising a PPARγ agonist, or a pharmaceutically acceptable salt or prodrug thereof.

In some embodiments, described herein is a method for treating an aging-induced hyperinsulinemia in a mammal in need thereof, comprising administering to the mammal a therapeutically effective amount of a formulation comprising a PPARγ agonist, or a pharmaceutically acceptable salt or prodrug thereof.

In some embodiments, described herein is a method for treating an aging-induced insulin resistance in a mammal in need thereof, comprising administering to the mammal a therapeutically effective amount of a formulation comprising a PPARγ agonist, or a pharmaceutically acceptable salt or prodrug thereof.

In some embodiments, described herein is a method for treating an aging-induced elevation of fatty acids in a mammal in need thereof, comprising administering to the mammal a therapeutically effective amount of a formulation comprising a PPARγ agonist, or a pharmaceutically acceptable salt or prodrug thereof.

In some embodiments, described herein is a method for mitigating or reversing an aging-induced insulin resistance in a companion animal in need thereof, regardless of the state of metabolic dysfunction with or without evidence of metabolic dysfunction, comprising administering to the companion animal a therapeutically effective amount of a formulation comprising a PPARγ agonist, or a pharmaceutically acceptable salt or prodrug thereof, wherein the companion animal is at least 4 years old. In some embodiments, described herein is method for mitigating or reversing insulin resistance in a companion animal in need thereof, comprising administering to the companion animal a therapeutically effective amount of a formulation comprising a PPARγ agonist, or a pharmaceutically acceptable salt or prodrug thereof, wherein the companion animal is at least 4 years old.

In some embodiments, described herein is a method for mitigating or reversing an aging-induced elevation of lipids, including fatty acids, triglycerides and cholesterol, in a companion animal in need thereof, with or without evidence of metabolic dysfunction, comprising administering to the companion animal a therapeutically effective amount of a formulation comprising a PPARγ agonist, or a pharmaceutically acceptable salt or prodrug thereof, wherein the companion animal is at least 4 years old. In some embodiments, described herein is a method for mitigating or reversing an aging-induced elevation of lipids, including fatty acids, triglycerides and cholesterol, in a companion animal in need thereof, comprising administering to the companion animal a therapeutically effective amount of a formulation comprising a PPARγ agonist, or a pharmaceutically acor a free base or a pharmaceutically acceptable salt or prodrug thereof, wherein the companion animal is at least 4 years old. In some embodiments, described herein is a method of maintaining or restoring healthy functioning of adipose tissue in a companion animal in need thereof, comprising administering to the companion animal a therapeutically effective amount of a formulation comprising a PPARγ agonist, or a pharmaceutically acceptable salt or prodrug thereof, wherein the companion animal is at least 4 years old.

In some embodiments, the method of treatment mitigates or reverses the High Fat Diet-induced insulin resistance in mammals. In some embodiments, the method of treatment mitigates or reverses the High Fat Diet-induced hyperinsulinemia in mammals. In some embodiments, the method of treatment mitigates or reverses the High Fat Diet-induced elevation of free fatty acids. Mitigation or reversing of the insulin resistance includes reducing insulin resistance compared to the levels without treatment. The mammal subject may have regained insulin sensitivity. Mitigation or reversing of the hyperinsulinemia includes reducing insulin resistance compared to the levels without treatment. The mammal subject may have lowered circulating insulin concentrations. Mitigation or reversing elevated levels of free fatty acids induced by the high fat diet includes but is not limited to reduction of the free fatty acid levels in the subject compared to the free fatty acid levels without treatment. Biomarkers to assess treatment efficacy may include, but are not limited to measuring glucose and free fatty acid levels in the subject.

In some embodiments, described herein is a method for mitigating or reversing a High Fat Diet (HFD)-induced insulin resistance in a mammal in need thereof, comprising administering to the mammal a therapeutically effective amount of a formulation comprising a PPARγ agonist, or a pharmaceutically acceptable salt or prodrug thereof.

In some embodiments, described herein is a method for mitigating or reversing insulin resistance in a mammal in need thereof, with or without evidence of metabolic dysfunction, comprising administering to the mammal a therapeutically effective amount of a formulation comprising a PPARγ agonist, or a pharmaceutically acceptable salt or prodrug thereof. In some embodiments, described herein is a method for mitigating or reversing insulin resistance in a mammal in need thereof, administering to the mammal a therapeutically effective amount of a formulation comprising a PPARγ agonist, or a pharmaceutically acceptable salt or prodrug thereof. In some embodiments, described herein is a method for mitigating or reversing insulin resistance in a mammal in need thereof, comprising administering to the mammal a therapeutically effective amount of a formulation comprising a PPARγ agonist, or a free base. In some embodiments, the reversing insulin resistance also reverses fasting insulin levels back to normal levels.

In some embodiments, the method does not directly impact glucose levels. In some embodiments, the method does not decrease glucose levels in the mammal. In some embodiments, the method does not increase the glucose levels in the mammals. In some embodiments, the method comprises administering a PPARγ agonist, or a pharmaceutically acceptable salt or prodrug thereof to a mammal that is susceptible to a change of glucose level. In some embodiments, the method comprises administering a PPARγ agonist, or a pharmaceutically acceptable salt or prodrug thereof to a mammal that is susceptible to an elevation of glucose level. In some embodiments, the method comprises administering a PPARγ agonist, or a pharmaceutically acceptable salt or prodrug thereof to a mammal that can benefit from a stable glucose level.

In some embodiments, the method increases adiponectin levels in the mammal at least 5%, at least 10%, at least 15%, at least 20%, at least 25%, at least 50% or at least 100%.

In some embodiments, the method decreases insulin levels in the mammals. In some embodiments, the insulin level is decreased by at least 5%, at least 10%, at least 15%, at least 20%, or at least 25%. In some embodiments, the insulin level is decreased by at least 5%, at least 10%, at least 15%, or at least 20%. In some embodiments, the insulin level is decreased by at least 5%. In some embodiments, the insulin level is decreased by at least 10%. In some embodiments, the insulin level is decreased by at least 15%. In some embodiments, the insulin level is decreased by at least 20%. In some embodiments, the insulin level is decreased by at least 25%.

In some embodiments, the method improves insulin sensitivity. Improving insulin sensitivity decreases insulin resistance such that the metabolism for insulin is mitigated or reverses towards pre-high fat diet levels. Pre-high fat diets and/or pre-aging related increases in insulin resistance may occur from decrease in insulin sensitivity. Any useful insulin sensitivity assay known by one of skill in the art can be used. In some embodiments, the insulin sensitivity is measured by an glucose clamp method, intravenous glucose tolerance test, oral glucose tolerance testing assay, or measured using fasting insulin blood levels. In some embodiments, the insulin sensitivity is measured by an oral glucose tolerance testing assay. In some embodiments, the insulin sensitivity is measured by using fasting insulin blood levels. Free fatty acids (FFAs) are fatty acids which are circulating in the plasma of the mammal. Generally, free fatty esters are not in their ester form, and are typically bound to a transport protein such as, but not limited to albumin. Free fatty acids can form from glycerides such as, but not limited to triglycerides. In some embodiments, the fatty acids can form lipids such as shingolipids, glycerolipids, and phospholipids.

In some embodiments, the fatty acid is saturated fatty acids, palmitic acid, linoleic acid, oleic acid, or a combination thereof. In some embodiments, the fatty acid is saturated fatty acids, palmitic acid, linoleic acid, or oleic acid. In some embodiments, the fatty acid is saturated fatty acids. In some embodiments, the fatty is palmitic acid. In some embodiments, the fatty is linoleic acid. In some embodiments, the fatty is oleic acid.

Triglycerides are fats that circulate in blood cells, which can be made by mammals via dietary intake or de novo lipogenesis. Triglyceride levels typically increase with age and in metabolic diseases. Administration of a PPARγ agonist such as pioglitazone can drop the levels of triglycerides in mammals.

Triglycerides can be a useful biomarker for determining insulin resistance and insulin sensitivity.

In some embodiments, the method decreases triglyceride levels in the mammal. In some embodiments, the method decreases triglyceride levels by at least 5%, at least 10%, at least 20%, at least 30%, at least 40%, or at least 50%. In some embodiments, the method decreases triglyceride levels by at least 5%. In some embodiments, the method decreases triglyceride levels by at least 10%. In some embodiments, the method decreases triglyceride levels by at least 15%. In some embodiments, the method decreases triglyceride levels by at least 20%. In some embodiments, the method decreases triglyceride levels by at least 25%.

Adiponectin is an insulin sensitizing adipokine protein, and can regulate glucose levels, lipid metabolism, and insulin sensitivity. Adiponectin can be upregulated by activating PPARγ/pioglitazone treatment. The adiponectin can be dose dependently upregulated by the degree of PPARγ activation/pioglitazone treatment. Adiponectin may also be linked to longevity in humans and other mammals. Adiponectins can be a useful biomarker for determining insulin resistance and insulin sensitivity.

In some embodiments, the method increases adiponectin levels in the mammal. In some embodiments, the method increases adiponectin levels by at least 5%, at least 10%, at least 20%, at least 30%, at least 40%, or at least 50%. In some embodiments, the method increases adiponectin levels by at least 5%. In some embodiments, the method increases adiponectin levels by at least 10%. In some embodiments, the method increases adiponectin levels by at least 20%. In some embodiments, the method increases adiponectin levels by at least 30%. In some embodiments, the method increases adiponectin levels by at least 40%. In some embodiments, the method increases adiponectin levels by at least 50%.

The subjects herein are mammals. In some embodiments, the mammal is a dog, cat, horse, cow, pig, rabbit, rodent, sheep, non-human primate, or human. In some embodiments, the mammal is a dog. In some embodiments, the mammal is a cat. In some embodiments, the mammal is a rodent. In some embodiments, the rodent is a mouse or a rat. In some embodiments, the mammal is a human.

The methods described herein describe a mammal as the subject. The mammal can be a companion animal. In some embodiments, the mammal is a companion animal. In some embodiments, the companion animal is a dog or cat. In some embodiments, the companion animal is a dog. In some embodiments, the companion animal is a cat.

In some embodiments, the companion animal is at least 2 years old. In some embodiments, the companion animal is at least 3 years old. In some embodiments, the companion animal is at least 4 years old. In some embodiments, the companion animal is at least 5 years old. In some embodiments, the companion animal is at least 6 years old. In some embodiments, the companion animal is at least 7 years old. In some embodiments, the companion animal is at least 8 years old. In some embodiments, the companion animal is at least 9 years old. In some embodiments, the companion animal is at least 10 years old. In some embodiments, the companion animal is at least 10 years old. In some embodiments, the companion animal is at least 11 years old. In some embodiments, the companion animal is at least 12 years old. In some embodiments, the companion animal is at least 13 years old. In some embodiments, the companion animal is at least 14 years old. In some embodiments, the companion animal is at least 15 years old.

The companion animal can have any suitable weight for the methods described herein. In some embodiments, the companion animal has a weight of at least 5 pounds. In some embodiments, the companion animal has a weight of at least 10 pounds. In some embodiments, the companion animal has a weight of at least 11 pounds. In some embodiments, the companion animal has a weight of at least 12 pounds. In some embodiments, the companion animal has a weight of at least 13 pounds. In some embodiments, the companion animal has a weight of at least 14 pounds. In some embodiments, the companion animal has a weight of at least 15 pounds. In some embodiments, the companion animal has a weight of at least 16 pounds. In some embodiments, the companion animal has a weight of at least 17 pounds. In some embodiments, the companion animal has a weight of at least 18 pounds. In some embodiments, the companion animal has a weight of at least 19 pounds. In some embodiments, the companion animal has a weight of at least 20 pounds. In some embodiments, the companion animal has a weight of at least 25 pounds. In some embodiments, the companion animal has a weight of at least 30 pounds In some embodiments, the companion animal is overweight. In some embodiments, the companion animal is obese.

In some embodiments is a method for increasing lifespan, promoting longevity, and/or preventing, reducing the severity of, or delaying the onset of various aging-associated conditions in a mammal in need thereof, comprising administering to the mammal a therapeutically effective amount of a formulation comprising a PPARγ agonist, or a pharmaceutically acceptable salt or prodrug thereof. In some embodiments, the PPARγ agonist, or a pharmaceutically acceptable salt or prodrug thereof is administered to the mammal before the onset of age-related metabolic dysfunction.

In some embodiments is a method for increasing lifespan, promoting longevity, and/or preventing, reducing the severity of or delaying the onset of various aging-associated conditions in a mammal in need thereof, comprising administering to the mammal a therapeutically effective amount of a formulation comprising a PPARγ agonist described herein.

In some embodiments is a method for treating the age-related decline in quality of life, comprising administering to the mammal a therapeutically effective amount of a formulation comprising a PPARγ agonist, or a pharmaceutically acceptable salt or prodrug thereof.

In some embodiments is a method for treating the age-related increase in frailty, comprising administering to the mammal a therapeutically effective amount of a formulation comprising a PPARγ agonist, or a pharmaceutically acceptable salt or prodrug thereof.

In some embodiments is a method for increasing lifespan in a mammal in need thereof, comprising administering to the mammal a therapeutically effective amount of a formulation described herein, wherein increasing lifespan comprises an at least 5% increase in lifespan relative to the expected or median lifespan of a mammal of similar species, strain, or breed.

In some embodiments is a method for increasing lifespan in a mammal in need thereof, comprising administering to the mammal a therapeutically effective amount of a formulation described herein, wherein increasing lifespan comprises an at least 10% increase in lifespan relative to the expected or median lifespan of a mammal of similar species, strain, or breed.

In some embodiments is a method for increasing lifespan in a mammal in need thereof, comprising administering to the mammal a therapeutically effective amount of a formulation described herein, wherein increasing lifespan comprises an at least 15% increase in lifespan relative to the expected or median lifespan of a mammal of similar species, strain, or breed.

In some embodiments is a method for increasing lifespan in a mammal in need thereof, comprising administering to the mammal a therapeutically effective amount of a formulation described herein, wherein increasing lifespan comprises an at least 20% increase in lifespan relative to the expected or median lifespan of a mammal of similar species, strain, or breed.

In some embodiments is a method for increasing lifespan in a mammal in need thereof, comprising administering to the mammal a therapeutically effective amount of a formulation described herein, wherein increasing lifespan comprises an at least 25% increase in lifespan relative to the expected or median lifespan of a mammal of similar species, strain, or breed.

In some embodiments the method comprises mitigating or reversing insulin resistance in the mammal. In some embodiments, the insulin resistance occurs from an aging process. In some embodiments, the method comprises mitigating or reversing an elevation of free fatty acids (FFAs). In some embodiments, the elevation of free fatty acids is associated with an age-related disease state. Age-related disease states include, but are not limited to obesity, type II diabetes, cardiovascular disease, sarcopenia, atherosclerosis, arthritis, and hypertension. In some embodiments, the age-related disease state is obesity, type II diabetes, cardiovascular disease, or sarcopenia. In some embodiments, the mammal (e.g., a companion animal) disclosed herein has diabetes. In some embodiments, the mammal (e.g., a companion animal) disclosed herein does not have diabetes. In some embodiments, the mammal does not have alloxan-induced diabetes. In some embodiments, the mammal has not been diagnosed as having diabetes.

In some embodiments is a method for promoting longevity in a mammal in need thereof, comprising administering to the mammal a therapeutically effective amount of a formulation described herein.

In some embodiments, the mammal has reached maturity as defined for their species. In some embodiments, the mammal has reached old age as defined for their species.

In some embodiments, the mammal is a dog, cat, horse, cow, pig, rabbit, rodent, sheep, non-human primate, or human. In some embodiments, the mammal is a dog. In some embodiments, the mammal is a cat. In some embodiments, the mammal is a rodent. In some embodiments, the rodent is a mouse or a rat. In some embodiments, the mammal is a human.

In some embodiments, the method described herein further comprises administering a second therapeutic agent in combination with the PPARγ agonist or a salt thereof. In some embodiments, the method described herein further comprises administering a second therapeutic agent in combination with pioglitazone or a salt thereof. In some embodiments, the second therapeutic agent is an agent selected from Table 12. In some embodiments, the second therapeutic agent is selected from Selegiline, Levothyroxine, NSAIDs, Steroids, chemotherapeutic agents, Sedatives and Anesthetics, Opioids (excluding tramadol), Tramadol, Anti-parasiticides (including HW px, ectoparasiticides, dewormers), Supplements, prescription diets, nutraceuticals (including CBD, glucosamine, fish oil), Vaccinations, Antibiotics (e.g., excluding macrolides and fluoroquinolones and macrocyclics), Fluoroquinolone antibiotics (ciprofloxacin, enrofloxacin, difloxacin, orbifloxacin, marbofloxacin), Ketoconazole, Non-ketoconazole antifungals (miconazole, fluconazole, etc.), and Heart medications which are not ACE inhibitors nor ACE receptor blockers.

Pharmaceutical Formulations

In some embodiments of the pharmaceutical formulations described herein, the PPARγ agonist is in the free base form. In some embodiments of the pharmaceutical formulations described herein, the PPARγ agonist is a salt. In some embodiments of the pharmaceutical formulations described herein, the PPARγ agonist is a hydrochloride salt. In some embodiments of the pharmaceutical formulations described herein, the PPARγ agonist is a maleate salt.

In some embodiments, one or more excipients described herein are in a salt form. In some embodiments, one or more excipients described herein are in a free base form.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C (R3), (November 2005). Hydrates are formed when the solvent is water, or alcoholates are formed when the solvent is alcohol. In some embodiments, solvates of the PPARγ agonist, or pharmaceutically acceptable salts thereof, are conveniently prepared or formed during the processes described herein. In some embodiments, solvates of the PPARγ agonist are anhydrous. In some embodiments, the PPARγ agonist, or pharmaceutically acceptable salts thereof, exist in unsolvated form. In some embodiments, the PPARγ agonist, or pharmaceutically acceptable salts thereof, exist in unsolvated form and are anhydrous. In some embodiments, one or more excipients described herein are solvated. In some embodiments, one or more excipients described herein are unsolvated.

In yet other embodiments, the PPARγ agonist, or a pharmaceutically acceptable salt or prodrug thereof, is prepared in various forms, including but not limited to, amorphous phase, crystalline forms, milled forms and nano-particulate forms. In some embodiments, the PPARγ agonist, or a pharmaceutically acceptable salt or prodrug thereof, is amorphous. In some embodiments, the PPARγ agonist or a pharmaceutically acceptable salt or prodrug thereof, is amorphous and anhydrous. In some embodiments, the PPARγ agonist, or a pharmaceutically acceptable salt or prodrug thereof, is crystalline. In some embodiments, the PPARγ agonist, or a pharmaceutically acceptable salt or prodrug thereof, is crystalline and anhydrous.

While not intending to be bound by any particular theory, certain solid forms are characterized by physical properties (e.g., stability, solubility and dissolution rate) appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The pharmaceutical formulations described herein comprise a PPARγ agonist, or a pharmaceutically acceptable salt or prodrug thereof, and at least one pharmaceutically acceptable excipient, in a solid dosage form. In some embodiments, the pharmaceutical formulations described herein comprise pioglitazone, and at least one pharmaceutically acceptable excipient, in a solid dosage form, wherein the solid dosage form is selected from a powder, a tablet, a bite-disintegration tablet, a chewable tablet, a caplet, a capsule, a gelcap, an effervescent powder, a rapid-disintegration tablet, an abuse-deterrent tablet, a modified release tablet, a modified release caplet, a modified release capsule, and an aqueous suspension produced from a powder. In some embodiments, the pharmaceutical formulation is a liquid formulation such as solution or suspension. In some embodiments, the pharmaceutical formulation is a parenteral formulation such as an injection formulation. In some embodiments, the pharmaceutical formulation is a solid form formulation. In some embodiments, the pharmaceutical formulation is a powder formulation that is added to food.

In some embodiments, the pharmaceutical formulations described herein comprise PPARγ agonist, or a pharmaceutically acceptable salt or prodrug thereof, and at least one pharmaceutically acceptable excipient, in a solid dosage form. In some embodiments, the solid dosage form is a tablet. In some embodiments, the solid dosage form is a capsule. In some embodiments, the pharmaceutical formulations described herein comprise pioglitazone, and at least one pharmaceutically acceptable excipient, in a solid dosage form, wherein the solid dosage form is a tablet.

In some embodiments, the pharmaceutical formulation comprises about 1% to about 35% of a PPARγ agonist, or a pharmaceutically acceptable salt or prodrug thereof. In some embodiments, the pharmaceutical formulation comprises about 0.5% to about 10% of a PPARγ agonist, or a pharmaceutically acceptable salt or prodrug thereof. In some embodiments, the pharmaceutical formulation comprises about 1% to about 35% of a PPARγ agonist, or a pharmaceutically acceptable salt or prodrug thereof. In some embodiments, the pharmaceutical formulation comprises about 2% to about 35% of a PPARγ agonist, or a pharmaceutically acceptable salt or prodrug thereof. In some embodiments, the pharmaceutical formulation comprises about 3% to about 35% of a PPARγ agonist, or a pharmaceutically acceptable salt or prodrug thereof. In some embodiments, the pharmaceutical formulation comprises about 5% to about 35% of a PPARγ agonist, or a pharmaceutically acceptable salt or prodrug thereof. In some embodiments, the pharmaceutical formulation comprises about 5% to about 35% of a PPARγ agonist, or a pharmaceutically acceptable salt or prodrug thereof. In some embodiments, the pharmaceutical formulation comprises about 10% to about 35% of a PPARγ agonist, or a pharmaceutically acceptable salt or prodrug thereof. In some embodiments, the pharmaceutical formulation comprises about 15% to about 35% of a PPARγ agonist, or a pharmaceutically acceptable salt or prodrug thereof. In some embodiments, the pharmaceutical formulation comprises about 10% to about 30% of a PPARγ agonist, or a pharmaceutically acceptable salt or prodrug thereof. In some embodiments, the pharmaceutical formulation comprises about 15% to about 30% of a PPARγ agonist, or a pharmaceutically acceptable salt or prodrug thereof. In some embodiments, the pharmaceutical formulation comprises about 20% to about 30% of a PPARγ agonist, or a pharmaceutically acceptable salt or prodrug thereof. In some embodiments, the pharmaceutical formulation comprises about 15% to about 25% of a PPARγ agonist, or a pharmaceutically acceptable salt or prodrug thereof. In some embodiments, the pharmaceutical formulation comprises about 20% to about 25% of a PPARγ agonist, or a pharmaceutically acceptable salt or prodrug thereof. In some embodiments, the pharmaceutical formulation comprises about 10% of a PPARγ agonist, or a pharmaceutically acceptable salt or prodrug thereof. In some embodiments, the pharmaceutical formulation comprises about 11% of a PPARγ agonist, or a pharmaceutically acceptable salt or prodrug thereof. In some embodiments, the pharmaceutical formulation comprises about 12% of a PPARγ agonist, or a pharmaceutically acceptable salt or prodrug thereof. In some embodiments, the pharmaceutical formulation comprises about 13% of a PPARγ agonist, or a pharmaceutically acceptable salt or prodrug thereof. In some embodiments, the pharmaceutical formulation comprises about 14% of a PPARγ agonist, or a pharmaceutically acceptable salt or prodrug thereof. In some embodiments, the pharmaceutical formulation comprises about 15% of a PPARγ agonist, or a pharmaceutically acceptable salt or prodrug thereof. In some embodiments, the pharmaceutical formulation comprises about 16% of a PPARγ agonist, or a pharmaceutically acceptable salt or prodrug thereof. In some embodiments, the pharmaceutical formulation comprises about 17% of a PPARγ agonist, or a pharmaceutically acceptable salt or prodrug thereof. In some embodiments, the pharmaceutical formulation comprises about 18% of a PPARγ agonist, or a pharmaceutically acceptable salt or prodrug thereof. In some embodiments, the pharmaceutical formulation comprises about 19% of a PPARγ agonist, or a pharmaceutically acceptable salt or prodrug thereof. In some embodiments, the pharmaceutical formulation comprises about 20% of a PPARγ agonist, or a pharmaceutically acceptable salt or prodrug thereof. In some embodiments, the pharmaceutical formulation comprises about 21% of a PPARγ agonist, or a pharmaceutically acceptable salt or prodrug thereof. In some embodiments, the pharmaceutical formulation comprises about 22% of a PPARγ agonist, or a pharmaceutically acceptable salt or prodrug thereof. In some embodiments, the pharmaceutical formulation comprises about 23% of a PPARγ agonist, or a pharmaceutically acceptable salt or prodrug thereof. In some embodiments, the pharmaceutical formulation comprises about 24% of a PPARγ agonist, or a pharmaceutically acceptable salt or prodrug thereof. In some embodiments, the pharmaceutical formulation comprises about 25% of a PPARγ agonist, or a pharmaceutically acceptable salt or prodrug thereof. In some embodiments, the pharmaceutical formulation comprises about 26% of a PPARγ agonist, or a pharmaceutically acceptable salt or prodrug thereof. In some embodiments, the pharmaceutical formulation comprises about 27% of a PPARγ agonist, or a pharmaceutically acceptable salt or prodrug thereof. In some embodiments, the pharmaceutical formulation comprises about 28% of a PPARγ agonist, or a pharmaceutically acceptable salt or prodrug thereof. In some embodiments, the pharmaceutical formulation comprises about 29% of a PPARγ agonist, or a pharmaceutically acceptable salt or prodrug thereof. In some embodiments, the pharmaceutical formulation comprises about 30% of a PPARγ agonist, or a pharmaceutically acceptable salt or prodrug thereof. In some embodiments, the pharmaceutical formulation comprises about 310% of a PPARγ agonist, or a pharmaceutically acceptable salt or prodrug thereof. In some embodiments, the pharmaceutical formulation comprises about 32% of a PPARγ agonist, or a pharmaceutically acceptable salt or prodrug thereof. In some embodiments, the pharmaceutical formulation comprises about 33% of a PPARγ agonist, or a pharmaceutically acceptable salt or prodrug thereof. In some embodiments, the pharmaceutical formulation comprises about 34% of a PPARγ agonist, or a pharmaceutically acceptable salt or prodrug thereof. In some embodiments, the pharmaceutical formulation comprises about 35% of a PPARγ agonist, or a pharmaceutically acceptable salt or prodrug thereof.

In some embodiments, the PPARγ agonist is selected from pioglitazone and rosiglitazone. In some embodiments, the pharmaceutical formulation comprises about 3% to about 35% of pioglitazone. In some embodiments, the pharmaceutical formulation comprises about 5% to about 35% of pioglitazone. In some embodiments, the pharmaceutical formulation comprises about 10% to about 35% of pioglitazone. In some embodiments, the pharmaceutical formulation comprises about 15% to about 35% of pioglitazone. In some embodiments, the pharmaceutical formulation comprises about 10% to about 30% of pioglitazone. In some embodiments, the pharmaceutical formulation comprises about 15% to about 30% of pioglitazone. In some embodiments, the pharmaceutical formulation comprises about 20% to about 30% of pioglitazone. In some embodiments, the pharmaceutical formulation comprises about 15% to about 25% of pioglitazone. In some embodiments, the pharmaceutical formulation comprises about 20% to about 25% of pioglitazone. In some embodiments, the pharmaceutical formulation comprises about 10% of pioglitazone. In some embodiments, the pharmaceutical formulation comprises about 11% of pioglitazone. In some embodiments, the pharmaceutical formulation comprises about 12% of pioglitazone. In some embodiments, the pharmaceutical formulation comprises about 13% of pioglitazone. In some embodiments, the pharmaceutical formulation comprises about 14% of pioglitazone. In some embodiments, the pharmaceutical formulation comprises about 15% of pioglitazone. In some embodiments, the pharmaceutical formulation comprises about 16% of pioglitazone. In some embodiments, the pharmaceutical formulation comprises about 17% of pioglitazone. In some embodiments, the pharmaceutical formulation comprises about 18% of pioglitazone. In some embodiments, the pharmaceutical formulation comprises about 19% of pioglitazone. In some embodiments, the pharmaceutical formulation comprises about 20% of pioglitazone. In some embodiments, the pharmaceutical formulation comprises about 21% of pioglitazone. In some embodiments, the pharmaceutical formulation comprises about 22% of pioglitazone. In some embodiments, the pharmaceutical formulation comprises about 23% of pioglitazone. In some embodiments, the pharmaceutical formulation comprises about 24% of pioglitazone. In some embodiments, the pharmaceutical formulation comprises about 25% of pioglitazone. In some embodiments, the pharmaceutical formulation comprises about 26% of pioglitazone. In some embodiments, the pharmaceutical formulation comprises about 27% of pioglitazone. In some embodiments, the pharmaceutical formulation comprises about 28% of pioglitazone. In some embodiments, the pharmaceutical formulation comprises about 29% of pioglitazone. In some embodiments, the pharmaceutical formulation comprises about 30% of pioglitazone. In some embodiments, the pharmaceutical formulation comprises about 31% of pioglitazone. In some embodiments, the pharmaceutical formulation comprises about 32% of pioglitazone. In some embodiments, the pharmaceutical formulation comprises about 33% of pioglitazone. In some embodiments, the pharmaceutical formulation comprises about 34% of pioglitazone. In some embodiments, the pharmaceutical formulation comprises about 35% of pioglitazone.

In some embodiments, the pharmaceutical formulation comprises about 5% to about 35% of rosiglitazone. In some embodiments, the pharmaceutical formulation comprises about 10% to about 35% of rosiglitazone. In some embodiments, the pharmaceutical formulation comprises about 15% to about 35% of rosiglitazone. In some embodiments, the pharmaceutical formulation comprises about 10% to about 30% of rosiglitazone. In some embodiments, the pharmaceutical formulation comprises about 15% to about 30% of rosiglitazone. In some embodiments, the pharmaceutical formulation comprises about 20% to about 30% of rosiglitazone. In some embodiments, the pharmaceutical formulation comprises about 15% to about 25% of rosiglitazone. In some embodiments, the pharmaceutical formulation comprises about 20% to about 25% of rosiglitazone. In some embodiments, the pharmaceutical formulation comprises about 10% of rosiglitazone. In some embodiments, the pharmaceutical formulation comprises about 11% of rosiglitazone. In some embodiments, the pharmaceutical formulation comprises about 12% of rosiglitazone. In some embodiments, the pharmaceutical formulation comprises about 13% of rosiglitazone. In some embodiments, the pharmaceutical formulation comprises about 14% of rosiglitazone. In some embodiments, the pharmaceutical formulation comprises about 15% of rosiglitazone. In some embodiments, the pharmaceutical formulation comprises about 16% of rosiglitazone. In some embodiments, the pharmaceutical formulation comprises about 17% of rosiglitazone. In some embodiments, the pharmaceutical formulation comprises about 18% of rosiglitazone. In some embodiments, the pharmaceutical formulation comprises about 19% of rosiglitazone. In some embodiments, the pharmaceutical formulation comprises about 20% of rosiglitazone. In some embodiments, the pharmaceutical formulation comprises about 21% of rosiglitazone. In some embodiments, the pharmaceutical formulation comprises about 22% of rosiglitazone. In some embodiments, the pharmaceutical formulation comprises about 23% of rosiglitazone. In some embodiments, the pharmaceutical formulation comprises about 24% of rosiglitazone. In some embodiments, the pharmaceutical formulation comprises about 25% of rosiglitazone. In some embodiments, the pharmaceutical formulation comprises about 26% of rosiglitazone. In some embodiments, the pharmaceutical formulation comprises about 27% of rosiglitazone. In some embodiments, the pharmaceutical formulation comprises about 28% of rosiglitazone. In some embodiments, the pharmaceutical formulation comprises about 29% of rosiglitazone. In some embodiments, the pharmaceutical formulation comprises about 30% of rosiglitazone. In some embodiments, the pharmaceutical formulation comprises about 31% of rosiglitazone. In some embodiments, the pharmaceutical formulation comprises about 32% of rosiglitazone. In some embodiments, the pharmaceutical formulation comprises about 33% of rosiglitazone. In some embodiments, the pharmaceutical formulation comprises about 34% of rosiglitazone. In some embodiments, the pharmaceutical formulation comprises about 35% of rosiglitazone. In some embodiments, the pharmaceutical formulation comprises about 1 mg to about 120 mg of a PPARγ agonist, or a pharmaceutically acceptable salt or prodrug thereof n some embodiments, the pharmaceutical formulation comprises about 1 mg to about 100 mg of a PPARγ agonist, or a pharmaceutically acceptable salt or prodrug thereof. In some embodiments, the pharmaceutical formulation comprises about 2 mg to about 120 mg of a PPARγ agonist, or a pharmaceutically acceptable salt or prodrug thereof. In some embodiments, the pharmaceutical formulation comprises about 3 mg to about 120 mg of a PPARγ agonist, or a pharmaceutically acceptable salt or prodrug thereof. In some embodiments, the pharmaceutical formulation comprises about 4 mg to about 120 mg of a PPARγ agonist, or a pharmaceutically acceptable salt or prodrug thereof. In some embodiments, the pharmaceutical formulation comprises about 4 mg to about 85 mg of the PPAR γ agonist, or a pharmaceutically acceptable salt or prodrug thereof. In some embodiments, the pharmaceutical formulation comprises about 5 mg to about 120 mg of a PPARγ agonist, or a pharmaceutically acceptable salt or prodrug thereof. In some embodiments, the pharmaceutical formulation comprises about 10 mg to about 120 mg of a PPARγ agonist, or a pharmaceutically acceptable salt or prodrug thereof. In some embodiments, the pharmaceutical formulation comprises about 10 mg to about 110 mg of a PPARγ agonist, or a pharmaceutically acceptable salt or prodrug thereof. In some embodiments, the pharmaceutical formulation comprises about 10 mg to about 100 mg of a PPARγ agonist, or a pharmaceutically acceptable salt or prodrug thereof. In some embodiments, the pharmaceutical formulation comprises about 20 mg to about 100 mg of a PPARγ agonist, or a pharmaceutically acceptable salt or prodrug thereof. In some embodiments, the pharmaceutical formulation comprises about 25 mg to about 100 mg of a PPARγ agonist, or a pharmaceutically acceptable salt or prodrug thereof. In some embodiments, the pharmaceutical formulation comprises about 30 mg to about 100 mg of a PPARγ agonist, or a pharmaceutically acceptable salt or prodrug thereof. In some embodiments, the pharmaceutical formulation comprises about 30 mg to about 90 mg of a PPARγ agonist, or a pharmaceutically acceptable salt or prodrug thereof. In some embodiments, the pharmaceutical formulation comprises about 40 mg to about 90 mg of a PPARγ agonist, or a pharmaceutically acceptable salt or prodrug thereof. In some embodiments, the pharmaceutical formulation comprises about 40 mg to about 80 mg of a PPARγ agonist, or a pharmaceutically acceptable salt or prodrug thereof. In some embodiments, the pharmaceutical formulation comprises about 45 mg to about 80 mg of a PPARγ agonist, or a pharmaceutically acceptable salt or prodrug thereof. In some embodiments, the pharmaceutical formulation comprises about 45 mg to about 75 mg of a PPARγ agonist, or a pharmaceutically acceptable salt or prodrug thereof. In some embodiments, the pharmaceutical formulation comprises about 50 mg to about 70 mg of a PPARγ agonist, or a pharmaceutically acceptable salt or prodrug thereof. In some embodiments, the pharmaceutical formulation comprises about 100 mg of a PPARγ agonist, or a pharmaceutically acceptable salt or prodrug thereof. In some embodiments, the pharmaceutical formulation comprises about 90 mg of a PPARγ agonist, or a pharmaceutically acceptable salt or prodrug thereof. In some embodiments, the pharmaceutical formulation comprises about 80 mg of a PPARγ agonist, or a pharmaceutically acceptable salt or prodrug thereof. In some embodiments, the pharmaceutical formulation comprises about 75 mg of a PPARγ agonist, or a pharmaceutically acceptable salt or prodrug thereof. In some embodiments, the pharmaceutical formulation comprises about 70 mg of a PPARγ agonist, or a pharmaceutically acceptable salt or prodrug thereof. In some embodiments, the pharmaceutical formulation comprises about 65 mg of a PPARγ agonist, or a pharmaceutically acceptable salt or prodrug thereof. In some embodiments, the pharmaceutical formulation comprises about 60 mg of a PPARγ agonist, or a pharmaceutically acceptable salt or prodrug thereof. In some embodiments, the pharmaceutical formulation comprises about 55 mg of a PPARγ agonist, or a pharmaceutically acceptable salt or prodrug thereof. In some embodiments, the pharmaceutical formulation comprises about 50 mg of a PPARγ agonist, or a pharmaceutically acceptable salt or prodrug thereof. In some embodiments, the pharmaceutical formulation comprises about 45 mg of a PPARγ agonist, or a pharmaceutically acceptable salt or prodrug thereof. In some embodiments, the pharmaceutical formulation comprises about 40 mg of a PPARγ agonist, or a pharmaceutically acceptable salt or prodrug thereof. In some embodiments, the pharmaceutical formulation comprises about 30 mg of a PPARγ agonist, or a pharmaceutically acceptable salt or prodrug thereof. In some embodiments, the pharmaceutical formulation comprises about 20 mg of a PPARγ agonist, or a pharmaceutically acceptable salt or prodrug thereof. In some embodiments, the pharmaceutical formulation comprises about 10 mg of a PPARγ agonist, or a pharmaceutically acceptable salt or prodrug thereof.

In some embodiments, the pharmaceutical formulation comprises about 1 mg to about 120 mg of a pioglitazone or a salt thereof n some embodiments, the pharmaceutical formulation comprises about 1 mg to about 100 mg of pioglitazone or a salt thereof. In some embodiments, the pharmaceutical formulation comprises about 2 mg to about 120 mg of pioglitazone or a salt thereof. In some embodiments, the pharmaceutical formulation comprises about 3 mg to about 120 mg of pioglitazone or a salt thereof. In some embodiments, the pharmaceutical formulation comprises about 4 mg to about 120 mg of pioglitazone or a salt thereof. In some embodiments, the pharmaceutical formulation comprises about 4 mg to about 85 mg of pioglitazone or a salt thereof. In some embodiments, the pharmaceutical formulation comprises about 5 mg to about 120 mg of pioglitazone or a salt thereof. In some embodiments, the pharmaceutical formulation comprises about 10 mg to about 120 mg of pioglitazone or a salt thereof. In some embodiments, the pharmaceutical formulation comprises about 10 mg to about 110 mg of pioglitazone or a salt thereof. In some embodiments, the pharmaceutical formulation comprises about 10 mg to about 100 mg of pioglitazone or a salt thereof. In some embodiments, the pharmaceutical formulation comprises about 20 mg to about 100 mg of pioglitazone or a salt thereof. In some embodiments, the pharmaceutical formulation comprises about 25 mg to about 100 mg of pioglitazone or a salt thereof. In some embodiments, the pharmaceutical formulation comprises about 30 mg to about 100 mg of pioglitazone or a salt thereof. In some embodiments, the pharmaceutical formulation comprises about 30 mg to about 90 mg of pioglitazone or a salt thereof. In some embodiments, the pharmaceutical formulation comprises about 40 mg to about 90 mg of pioglitazone or a salt thereof. In some embodiments, the pharmaceutical formulation comprises about 40 mg to about 80 mg of pioglitazone or a salt thereof. In some embodiments, the pharmaceutical formulation comprises about 45 mg to about 80 mg of pioglitazone or a salt thereof. In some embodiments, the pharmaceutical formulation comprises about 45 mg to about 75 mg of pioglitazone or a salt thereof. In some embodiments, the pharmaceutical formulation comprises about 50 mg to about 70 mg of pioglitazone or a salt thereof. In some embodiments, the pharmaceutical formulation comprises about 100 mg of pioglitazone or a salt thereof or a salt thereof. In some embodiments, the pharmaceutical formulation comprises about 90 mg of pioglitazone or a salt thereof. In some embodiments, the pharmaceutical formulation comprises about 80 mg of pioglitazone or a salt thereof. In some embodiments, the pharmaceutical formulation comprises about 75 mg of pioglitazone or a salt thereof. In some embodiments, the pharmaceutical formulation comprises about 70 mg of pioglitazone or a salt thereof. In some embodiments, the pharmaceutical formulation comprises about 65 mg of pioglitazone or a salt thereof. In some embodiments, the pharmaceutical formulation comprises about 60 mg of pioglitazone or a salt thereof. In some embodiments, the pharmaceutical formulation comprises about 55 mg of pioglitazone or a salt thereof. In some embodiments, the pharmaceutical formulation comprises about 50 mg of pioglitazone or a salt thereof. In some embodiments, the pharmaceutical formulation comprises about 45 mg of pioglitazone or a salt thereof. In some embodiments, the pharmaceutical formulation comprises about 40 mg of pioglitazone or a salt thereof. In some embodiments, the pharmaceutical formulation comprises about 30 mg of pioglitazone or a salt thereof. In some embodiments, the pharmaceutical formulation comprises about 20 mg of pioglitazone or a salt thereof. In some embodiments, the pharmaceutical formulation comprises about 10 mg pioglitazone or a salt thereof. In some embodiments, a pharmaceutical formulation described herein comprises about 18 mg of pioglitazone or a salt thereof. In some embodiments, a pharmaceutical formulation described herein comprises about 16 mg to about 20 mg of pioglitazone or a salt thereof. In some embodiments, a pharmaceutical formulation described herein comprises about 54 mg of pioglitazone or a salt thereof. In some embodiments, the pharmaceutical formulation comprises about 52 mg to about 56 of pioglitazone or a salt thereof. In some embodiments, the pharmaceutical formulation comprises about 81 mg of pioglitazone or a salt thereof. In some embodiments, the pharmaceutical formulation comprises about 79 mg to about 83 mg of pioglitazone or a salt thereof.

In some embodiments, the pharmaceutical formulation comprises about 10 mg to about 120 mg of rosiglitazone or a salt thereof. In some embodiments, the pharmaceutical formulation comprises about 10 mg to about 110 mg of rosiglitazone or a salt thereof. In some embodiments, the pharmaceutical formulation comprises about 10 mg to about 100 mg of rosiglitazone or a salt thereof. In some embodiments, the pharmaceutical formulation comprises about 20 mg to about 100 mg of rosiglitazone or a salt thereof. In some embodiments, the pharmaceutical formulation comprises about 25 mg to about 100 mg of rosiglitazone or a salt thereof. In some embodiments, the pharmaceutical formulation comprises about 30 mg to about 100 mg of rosiglitazone or a salt thereof. In some embodiments, the pharmaceutical formulation comprises about 30 mg to about 90 mg of rosiglitazone or a salt thereof. In some embodiments, the pharmaceutical formulation comprises about 40 mg to about 90 mg of rosiglitazone or a salt thereof. In some embodiments, the pharmaceutical formulation comprises about 40 mg to about 80 mg of rosiglitazone or a salt thereof or a salt thereof. In some embodiments, the pharmaceutical formulation comprises about 45 mg to about 80 mg of rosiglitazone. In some embodiments, the pharmaceutical formulation comprises about 45 mg to about 75 mg of rosiglitazone or a salt thereof. In some embodiments, the pharmaceutical formulation comprises about 50 mg to about 70 mg of rosiglitazone or a salt thereof. In some embodiments, the pharmaceutical formulation comprises about 100 mg of rosiglitazone or a salt thereof. In some embodiments, the pharmaceutical formulation comprises about 90 mg of rosiglitazone or a salt thereof. In some embodiments, the pharmaceutical formulation comprises about 80 mg of rosiglitazone or a salt thereof. In some embodiments, the pharmaceutical formulation comprises about 75 mg of rosiglitazone or a salt thereof. In some embodiments, the pharmaceutical formulation comprises about 70 mg of rosiglitazone or a salt thereof. In some embodiments, the pharmaceutical formulation comprises about 65 mg of rosiglitazone or a salt thereof. In some embodiments, the pharmaceutical formulation comprises about 60 mg of rosiglitazone or a salt thereof. In some embodiments, the pharmaceutical formulation comprises about 55 mg of rosiglitazone or a salt thereof. In some embodiments, the pharmaceutical formulation comprises about 50 mg of rosiglitazone or a salt thereof. In some embodiments, the pharmaceutical formulation comprises about 45 mg of rosiglitazone or a salt thereof. In some embodiments, the pharmaceutical formulation comprises about 40 mg of rosiglitazone or a salt thereof. In some embodiments, the pharmaceutical formulation comprises about 30 mg of rosiglitazone or a salt thereof. In some embodiments, the pharmaceutical formulation comprises about 20 mg of rosiglitazone or a salt thereof. In some embodiments, the pharmaceutical formulation comprises about 10 mg of rosiglitazone or a salt thereof.

In some embodiments, the PPARγ agonist (such as pioglitazone or rosiglitazone, or a salt thereof) is administered in an amount of 0.01 mg/kg to 100 mg/kg. In some embodiments, the PPARγ agonist is administered in an amount of 1 mg/kg to 20 mg/kg. In some embodiments, the PPARγ agonist is administered in an amount of 1 mg/kg to 10 mg/kg. In some embodiments, the PPARγ agonist is administered in an amount of 1 mg/kg to 5 mg/kg. In some embodiments, the PPARγ agonist is administered in an amount of 1 mg/kg. In some embodiments, the PPARγ agonist is administered in an amount of 2 mg/kg.

In one aspect, described herein is a pharmaceutical formulation in a solid dosage form comprising a PPARγ agonist, or a pharmaceutically acceptable salt thereof; and a filler. In one aspect, described herein is a pharmaceutical formulation in a solid dosage form comprising about 5 wt % to about 20 wt % of a PPARγ agonist, or a pharmaceutically acceptable salt thereof; and about 80 wt % to about 95 wt % of a filler. In some embodiments, the pharmaceutical formulation further comprises a disintegrant, a binder, a lubricant, a flavoring agent, or a combination thereof. In some embodiments, the disintegrant is present in the formulation in an amount of about 1% to about 10% by weight. In some embodiments, the binder is present in the formulation in an amount of about 1% to about 10% by weight. In some embodiments, the lubricant is present in the formulation in an amount of about 0.3% to about 3% by weight. In some embodiments, the flavoring agent is present in the formulation in an amount of about 0.03% to about 30% by weight. In some embodiments, the flavoring agent is meat flavoring. In some embodiments, the PPARγ agonist, or a pharmaceutically acceptable salt thereof is present in the formulation in an amount of about 1% to about 99% by weight. In some embodiments, the PPARγ agonist, or a pharmaceutically acceptable salt thereof is present in the formulation in an amount of about 7% to about 15% by weight. In some embodiments, the PPARγ agonist, or a pharmaceutically acceptable salt thereof is present in the formulation in an amount of about 10% to about 12% by weight. In some embodiments, the PPARγ agonist, or a pharmaceutically acceptable salt thereof is present in the formulation in an amount of about 11% by weight. In some embodiments, the PPARγ agonist, or a pharmaceutically acceptable salt thereof is present in the formulation in an amount of about 2%, about 3%, about 4%, about 5%, about 6%, about 7%, about 8%, about 9%, about 10%, about 11%, about 12%, about 13%, about 14%, or about 15% by weight.

In some embodiments, a formulation described herein comprises one or more fillers. In some embodiments, the filler(s) is present in the formulation in an amount of about 10% to about 80% by weight. In some embodiments, the filler(s) is present in the formulation in an amount of about 40% to about 80% by weight. In some embodiments, the filler(s) is present in the formulation in an amount of about 55% to about 70% by weight. In some embodiments, the filler(s) is present in the formulation in an amount of about 20% to about 60% by weight. In some embodiments, the filler(s) is present in the formulation in an amount of about 25% to about 50% by weight. In some embodiments, the filler(s) is present in the formulation in an amount of about 30% to about 45% by weight. In some embodiments, the filler(s) is present in the formulation in an amount of about 45% to about 50% by weight. In some embodiments, the one or more fillers comprises lactose monohydrate, hydroxypropyl cellulose, carboxymethyl cellulose sodium, or a combination thereof.

Fillers or diluents increase bulk in the pharmaceutical formulation. Such compounds include e.g., lactose; starch; mannitol; sorbitol; dextrose; microcrystalline cellulose such as Avicel®; dibasic calcium phosphate; dicalcium phosphate dihydrate; tricalcium phosphate; calcium phosphate; anhydrous lactose; spray-dried lactose; pregelatinzed starch; compressible sugar, such as Di-Pac® (Amstar); hydroxypropylmethylcellulose; sucrose-based diluents; confectioner's sugar; monobasic calcium sulfate monohydrate; calcium sulfate dihydrate; calcium lactate trihydrate; dextrates; hydrolyzed cereal solids; amylose; powdered cellulose; calcium carbonate; glycine; kaolin; sodium chloride; inositol; bentonite; and the like. In some embodiments, the filler comprises lactose, mannitol, dicalcium phosphate, cellulose, starch (e.g., pregelatinized starch), or a combination thereof. In some embodiments, the filler comprises lactose, mannitol, microcrystalline cellulose, or a combination thereof. In some embodiments, the filler comprises lactose. In some embodiments, the filler comprises lactose monohydrate. In some embodiments, the filler comprises hydroxypropyl cellulose. In some embodiments, the filler comprises carboxymethyl cellulose sodium. In some embodiments, the filler comprises carboxymethylcellulose, methylcellulose, hydroxypropylmethylcellulose, hydroxypropylmethylcellulose acetate stearate, hydroxyethylcellulose, hydroxypropylcellulose ethylcellulose, microcrystalline cellulose, or a combination thereof.

In some embodiments, the filler comprises lactose monohydrate, carboxymethyl cellulose sodium, and hydroxypropyl cellulose.

Disintegrants facilitate breakup or disintegration of the pharmaceutical formulation after administration. Examples of disintegrants include a starch, e.g., a natural starch such as corn starch or potato starch, a pregelatinized starch such as National 1551 or Amijel®, or sodium starch glycolate such as Promogel® or Explotab®; a cellulose such as a wood product, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinyl pyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a resin such as a cation-exchange resin; citrus pulp; sodium lauryl sulfate; sodium lauryl sulfate in combination starch; and the like. In some embodiments, the pharmaceutical formulation comprises a disintegrant. In some embodiments, the disintegrant is selected from corn starch, potato starch, microcrystalline cellulose, methylcellulose, croscarmellose sodium, sodium starch glycolate, povidone, crospovidone, hypromellose, hydroxypropyl cellulose, polyvinyl alcohol, alginic acid, sodium alginate, agar, guar, locust bean, Karaya, pectin, tragacanth, bentonite, citrus pulp, and sodium lauryl sulfate. In some embodiments, the disintegrant is selected from povidone, crospovidone, hypromellose, croscarmellose sodium, hydroxypropyl cellulose, and polyvinyl alcohol. In some embodiments, the disintegrant is polyvinyl alcohol. In some embodiments, the disintegrant is povidone. In some embodiments, the disintegrant is crospovidone. In some embodiments, the disintegrant is croscarmellose sodium.

In some embodiments, the pharmaceutical formulation comprises about 1% to about 10% of a disintegrant. In some embodiments, the pharmaceutical formulation comprises about 1% to about 9% of a disintegrant. In some embodiments, the pharmaceutical formulation comprises about 2% to about 10% of a disintegrant. In some embodiments, the pharmaceutical formulation comprises about 2% to about 9% of a disintegrant. In some embodiments, the pharmaceutical formulation comprises about 2% to about 8% of a disintegrant. In some embodiments, the pharmaceutical formulation comprises about 3% to about 8% of a disintegrant. In some embodiments, the pharmaceutical formulation comprises about 3% to about 7% of a disintegrant. In some embodiments, the pharmaceutical formulation comprises about 3% to about 6% of a disintegrant. In some embodiments, the pharmaceutical formulation comprises about 4% to about 7% of a disintegrant.

Lubricants are compounds which prevent, reduce, or inhibit adhesion or friction of materials. Exemplary lubricants include, e.g., stearic acid; calcium hydroxide, talc; a hydrocarbon such as mineral oil, or hydrogenated vegetable oil such as hydrogenated soybean oil (Sterotex®), Lubritab®, Cutina®; higher fatty acids and their alkali-metal and alkaline earth metal salts, such as aluminum, calcium, magnesium, zinc, stearic acid, sodium stearates, magnesium stearate, glycerol, talc, waxes, Stearowet®, boric acid, sodium acetate, leucine, a polyethylene glycol or a methoxypolyethylene glycol such as Carbowax™, sodium oleate, glyceryl behenate (Compitrol 888®), glyceryl palmitostearate (Precirol®), colloidal silica such as Syloid™, Carb-O-Sil®, a starch such as corn starch, silicone oil, a surfactant, and the like. Hydrophilic lubricants include, e.g., sodium stearyl fumarate (currently marketed under the trade name PRUV®), polyethylene glycol (PEG), magnesium lauryl sulfate, sodium lauryl sulfate (SLS), sodium benzoate, sodium chloride, and the like. In some embodiments, the pharmaceutical formulation comprises a lubricant. In some embodiments, the lubricant is selected from magnesium stearate, stearic acid, and sodium stearyl fumarate. In some embodiments, the lubricant is magnesium stearate. In some embodiments, the lubricant is stearic acid. In some embodiments, the lubricant is sodium stearyl fumarate.

In some embodiments, the pharmaceutical formulation comprises about 0.1% to about 10% of a lubricant. In some embodiments, the pharmaceutical formulation comprises about 0.3% to about 3% of a lubricant. In some embodiments, the pharmaceutical formulation comprises about 0.3% to about 2.5% of a lubricant. In some embodiments, the pharmaceutical formulation comprises about 0.3% to about 2% of a lubricant. In some embodiments, the pharmaceutical formulation comprises about 0.5% to about 2% of a lubricant. In some embodiments, the pharmaceutical formulation comprises about 0.5% to about 1.5% of a lubricant.

In some embodiments, the pharmaceutical formulation described herein comprises a flavoring agent. In some embodiments, the pharmaceutical formulation described herein comprises a flavoring agent. In some embodiments, the flavoring is natural. In some embodiments, the flavoring agent is artificial. In some embodiments, the pharmaceutical formulation comprises a meat flavoring. In some embodiments, the meat flavoring is natural.

In some embodiments, the meat flavoring is artificial. In some embodiments, the meat flavoring is selected from chicken, pork, and beef. In some embodiments, the flavoring agent is FlavorPal such as FlavorPal X1212.

In some embodiments, the pharmaceutical formulation comprises about 10% to about 30% of a meat flavoring. In some embodiments, the pharmaceutical formulation comprises about 15% to about 30% of a meat flavoring. In some embodiments, the pharmaceutical formulation comprises about 10% to about 25% of a meat flavoring. In some embodiments, the pharmaceutical formulation comprises about 15% to about 25% of a meat flavoring. In some embodiments, the pharmaceutical formulation comprises about 10% to about 30% of chicken flavoring. In some embodiments, the pharmaceutical formulation comprises about 15% to about 30% of chicken flavoring. In some embodiments, the pharmaceutical formulation comprises about 10% to about 25% of chicken flavoring. In some embodiments, the pharmaceutical formulation comprises about 10% to about 30% of a flavoring agent. In some embodiments, the pharmaceutical formulation comprises about 15% to about 30% of a flavoring agent. In some embodiments, the pharmaceutical formulation comprises about 10% to about 25% of a flavoring agent. In some embodiments, the pharmaceutical formulation comprises about 15% to about 25% of a flavoring agent. In some embodiments, the pharmaceutical formulation comprises about 10% to about 30% of flavoring agent. In some embodiments, the pharmaceutical formulation comprises about 15% to about 30% of flavoring agent. In some embodiments, the pharmaceutical formulation comprises about 10% to about 25% of flavoring agent.

Glidants improve the flow characteristics of a powder mixtures. Such compounds include, e.g., colloidal silicon dioxide such as Cab-o-Sil®; tribasic calcium phosphate, talc, corn starch, DL-leucine, sodium lauryl sulfate, magnesium stearate, calcium stearate, sodium stearate, kaolin, and micronized amorphous silicon dioxide (Syloid®) and the like. In some embodiments of the pharmaceutical formulations described herein, the glidant is colloidal silicon dioxide or talc. In some embodiments, the glidant is talc. In some embodiments, the glidant is colloidal silicon dioxide.

Polymeric carriers include compounds such as polyvinyl pyrrolidone, e.g., polyvinylpolyvinyl pyrrolidone K12, polyvinyl pyrrolidone K17, polyvinyl pyrrolidone K25, or polyvinyl pyrrolidone K30, polyvinyl pyrrolidone vinyl acetate (PVPVA 64), hydroxypropylmethylcellulose (HPMC), hydroxypropylmethylcellulose acetylsuccinate (HPMC AS), and methylmethacrylate polymers (Eudragit polymers) and the like.

In some embodiments, the pharmaceutical formulations described herein include one or more pH-adjusting agents or buffering agents. In some embodiments, the pharmaceutical formulation comprises a buffer selected from acetates, carbonates, phosphates, citrates, and glutamates. In some embodiments, the buffer is selected from potassium dihydrogen phosphate, sodium bicarbonate, magnesium carbonate, sodium citrate, sodium dihydrogen phosphate, dipotassium monohydrogen phosphate, and disodium monohydrogen phosphate.

In some embodiments, buffers are included in an amount required to maintain pH of the pharmaceutical formulation in an acceptable range.

In some embodiments, in order to mask the taste of the formulation, a polymer coating is provided around the pharmaceutical composition to provide a physical barrier against the taste buds. In some embodiments, the coating material is selected from hydrophobic or hydrophilic polymers, lipids, and sweeteners. In some embodiments, the coating material is selected from carbohydrates (cellulose), proteins, gelatins, and prolamins. In some embodiments, the coating material is selected from Eudragit E-100, ethylcellulose, hydroxypropyl methylcellulose (HPMC), hydroxypropyl cellulose (HPC), polyvinyl alcohol, and polyvinyl acetate.

Stabilizers include compounds such as any anti-oxidation agents, e.g., butylated hydroxytoluene (BHT), sodium ascorbate, and tocopherol; buffers, acids, and the like. In some embodiments, the pharmaceutical formulation comprises a stabilizer.

Surfactants include compounds such as sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), d-α-tocopheryl polyethylene glycol succinate (Vitamin E TPGS); and the like. In some embodiments, the pharmaceutical formulation comprises a surfactant.

In some embodiments, described herein is a pharmaceutical formulation in a solid dosage form that comprises an intra-granulation.

In some embodiments, described herein is a pharmaceutical formulation in a solid dosage form comprising, (a) pioglitazone or a salt thereof, (b) one or more fillers (e.g., lactose monohydrate, hydroxypropyl cellulose, carboxymethyl cellulose sodium, or a combination thereof), (c) a lubricant (e.g., magnesium stearate), and (d) a flavoring agent. In some embodiments, described herein is a pharmaceutical formulation in a solid dosage form comprising, by weight:
  (a) about 5% to about 20% of pioglitazone or a salt thereof;
  (b) about 25% to about 50% of lactose (e.g., lactose monohydrate);
  (c) about 0.1% to about 10% of hydroxypropyl cellulose;
  (d) about 1% to about 10% of carboxymethyl cellulose sodium; and
  (e) optionally a flavoring agent.

In some embodiments, described herein is a pharmaceutical formulation in a solid dosage form comprising, by weight:
  (a) about 5% to about 30% of pioglitazone or a salt thereof;
  (b) about 25% to about 80% of lactose (e.g., lactose monohydrate);
  (c) about 0.1% to about 10% of hydroxypropyl cellulose;
  (d) about 1% to about 25% of carboxymethyl cellulose sodium; and
  (e) optionally a flavoring agent.

In some embodiments, described herein is a pharmaceutical formulation in a solid dosage form comprising:
  (a) about 10 mg to about 100 mg of pioglitazone or a salt thereof;
  (b) about 50 mg to about 400 mg of lactose (e.g., lactose monohydrate);
  (c) about 0.5 mg to about 15 mg of hydroxypropyl cellulose;
  (d) about 1 mg to about 50 mg of carboxymethyl cellulose sodium; and
  (e) optionally a flavoring agent.

In some embodiments, described herein is a pharmaceutical formulation in a solid dosage form comprising:
  (a) about 5% to about 20% of pioglitazone or a salt thereof;
  (b) about 25% to about 50% of filler (lactose, cellulose, etc);
  (c) about 0.10% to about 10% of binder;
  (d) optionally about 1% to about 10% disintegrant; and
  (e) optionally a flavoring agent.

In some embodiments, the PPARγ agonist (such as pioglitazone or rosiglitazone) is administered daily, every other day, once a week, or once every two weeks. In some embodiments, the PPARγ agonist is administered for at least about 2 weeks. In some embodiments, the PPARγ agonist is administered for at least about 4 weeks. In some embodiments, the PPARγ agonist is administered for at least about 8 weeks. In some embodiments, the PPARγ agonist is administered for at least about 4 months. In some embodiments, the PPARγ agonist is administered for at least about 6 months. In some embodiments, the PPARγ agonist is administered for at least about 8 months. In some embodiments, the PPARγ agonist is administered for at least about 10 months. In some embodiments, the PPARγ agonist is administered for at least about 1 year. In some embodiments, the PPARγ agonist is administered for at least about 2 year. In some embodiments, the PPARγ agonist is administered throughout the life of the mammal.

In some embodiments, the PPARγ agonist is administered daily. In some embodiments, PPARγ agonist is administered weekly. In some embodiments, the PPARγ agonist is administered once a week. In some embodiments, the PPARγ agonist is administered 2 or more times a week. In some embodiments, In some embodiments, PPARγ agonist is administered monthly.

In some embodiments, the PPARγ agonist is administered at 1 mg/kg/day to 20 mg/kg/day. In some embodiments, the PPARγ agonist is administered at 1 mg/kg/day to 10 mg/kg/day. In some embodiments, the PPARγ agonist is administered at 1 mg/kg/day to 5 mg/kg/day. In some embodiments, the PPARγ agonist is administered at 2 mg/kg/day to 3 mg/kg/day. In some embodiments, the PPARγ agonist is administered at 1 mg/kg/day. In some embodiments, the PPARγ agonist is administered at 2 mg/kg/day. In some embodiments, the PPARγ agonist is administered at 3 mg/kg/day. In some embodiments, the PPARγ agonist is administered at 4 mg/kg/day. In some embodiments, the PPARγ agonist is administered at 5 mg/kg/day. In some embodiments, the PPARγ agonist is administered at 6 mg/kg/day. In some embodiments, the PPARγ agonist is administered at 7 mg/kg/day. In some embodiments, the PPARγ agonist is administered at 8 mg/kg/day. In some embodiments, the PPARγ agonist is administered at 9 mg/kg/day. In some embodiments, the PPARγ agonist is administered at 10 mg/kg/day. In some embodiments, the PPARγ agonist is a salt of pioglitazone. In some embodiments, the PPARγ agonist is a HCl salt of pioglitazone. In some embodiments, the PPARγ agonist is pioglitazone. In some embodiments, the pioglitazone or a salt thereof is administered at 1 mg/kg/day to 20 mg/kg/day. In some embodiments, the pioglitazone or a salt thereof is administered at 1 mg/kg/day to 10 mg/kg/day. In some embodiments, the pioglitazone or a salt thereof is administered at 1 mg/kg/day to 5 mg/kg/day. In some embodiments, the pioglitazone or a salt thereof is administered at 2 mg/kg/day to 3 mg/kg/day. In some embodiments, the pioglitazone or a salt thereof is administered at 1 mg/kg/day. In some embodiments, the pioglitazone or a salt thereof is administered at 2 mg/kg/day. In some embodiments, the pioglitazone or a salt thereof is administered at 3 mg/kg/day. In some embodiments, the pioglitazone or a salt thereof is administered at 4 mg/kg/day. In some embodiments, the pioglitazone or a salt thereof is administered at 5 mg/kg/day. In some embodiments, the pioglitazone or a salt thereof is administered at 6 mg/kg/day. In some embodiments, the pioglitazone or a salt thereof is administered at 7 mg/kg/day. In some embodiments, the pioglitazone or a salt thereof is administered at 8 mg/kg/day. In some embodiments, the pioglitazone or a salt thereof is administered at 9 mg/kg/day. In some embodiments, the pioglitazone or a salt thereof is administered at 10 mg/kg/day.

In some embodiments, the PPARγ agonist (such as pioglitazone or rosiglitazone, or salt thereof) is administered over a period of 1 day to 20 years. In some embodiments, the PPARγ agonist is administered over a period of 1 day to 15 years. In some embodiments, the PPARγ agonist is administered over a period of 1 day to 10 years. In some embodiments, the PPARγ agonist is administered over a period of 1 week to 1 year. In some embodiments, the PPARγ agonist is administered over a period of at least 1 day, 1 week, 1 month, 3 months, or 6 months. In some embodiments, the PPARγ agonist is administered over a period of at most 1 month, 3 months, 6 months, 9 months, 1 year, or 2 years. In some embodiments, the PPARγ agonist is administered chronically. In some embodiments, the PPARγ agonist is administered throughout the remaining life of the mammal (such as a companion animal).

The formulation and the PPARγ agonist can be in a suitable oral formulation for administration to the companion animal to take by mouth. In some embodiments, the formulation is in a solid dosage form. In some embodiments, the formulation is in the form of a tablet. In some embodiments, the PPARγ agonist is in the form of a tablet. In some embodiments, the PPARγ agonist is in the form of a capsule. In some embodiments, In some embodiments, the tablet is a flavored tablet. In some embodiments, the tablet or capsule comprises chicken, pork, beef, lamb, or fish flavor. In some embodiments, the tablet or capsule comprises chicken, pork, beef, or lamb flavor. In some embodiments, the tablet or capsule comprises hydrolyzed chicken product or chicken flavor.

In some embodiments, the tablet comprises about 18 mg, 54 mg, or 81 mg of the PPARγ agonist. In some embodiments, the tablet comprises about 18 mg of the PPARγ agonist. In some embodiments, the tablet comprises about 54 mg of the PPARγ agonist. In some embodiments, the tablet comprises about 81 mg of the PPARγ agonist. In some embodiments, the capsule comprises about 18 mg, 54 mg, or 81 mg of the PPARγ agonist. In some embodiments, the capsule comprises about 18 mg of the PPARγ agonist. In some embodiments, the capsule comprises about 54 mg of the PPARγ agonist. In some embodiments, the capsule comprises about 81 mg of the PPARγ agonist. In some embodiments, the PPARγ agonist is pioglitazone hydrochloride.

In some embodiments, the solid dosage form (e.g., tablet or capsule) further comprises at least one filler. In some embodiments, the solid dosage form comprises at least two fillers. In some embodiments, the solid dosage form comprises at least three fillers. In some embodiments, the filler is lactose monohydrate. In some embodiments, the lactose monohydrate is in an amount of 10% to 40% w/w. In some embodiments, the lactose monohydrate is in an amount of 10% to 30% w/w. In some embodiments, the lactose monohydrate is in an amount of about 15% to 25% w/w. In some embodiments, the lactose monohydrate is in an amount of 30% to 40% w/w. In some embodiments, the lactose monohydrate is in an amount of 32% to 40% w/w. In some embodiments, the lactose monohydrate is in an amount of 35% to 40% w/w. In some embodiments, the lactose monohydrate is in an amount of about 36% to about 38% w/w. In some embodiments, the lactose monohydrate is in the amount of about 37% w/w. In some embodiments, the lactose monohydrate is in an amount of about 22% w/w.

In some embodiments, the solid dosage form further comprises carboxymethyl cellulose Na. In some embodiments, the carboxymethyl cellulose is in an amount of about 1% to about 10% w/w. In some embodiments, the carboxymethyl cellulose is in an amount of about 2% to about 10% w/w. In some embodiments, the carboxymethyl cellulose is in an amount of about 2% to about 8% w/w. In some embodiments, the carboxymethyl cellulose is in an amount of about 2% to about 6% w/w. In some embodiments, the carboxymethyl cellulose is in an amount of about 3% to about 5% w/w. In some embodiments, the carboxymethyl cellulose is in an amount of about 4% w/w.

In some embodiments, the solid dosage form (e.g., a tablet or capsule) further comprises hydroxypropyl cellulose. In some embodiments, the hydroxypropyl cellulose is in an amount of about 0.1% to about 5% w/w. In some embodiments, the hydroxypropyl cellulose is in an amount of about 0.25% to about 3% w/w. In some embodiments the hydroxypropyl cellulose is in an amount of about 0.5% to about 2% w/w. In some embodiments, the hydroxypropyl cellulose is in an amount of about 1% w/w.

The hydroxypropyl cellulose grades useful for the present invention includes different viscosity grades that have an average molecular weight ranging from 20 to 1500 kDa. The hydroxypropyl cellulose grade useful for the present invention can include, but is not limited to the EXF grade. The EXF grade can have a viscosity of about 300 to 600 mPa·s. In some embodiments, the solid dosage form (e.g., a tablet or capsule) further comprises a flavoring agent such as FlavorPALX1212. In some embodiments, the flavoring agent is in an amount of about 10 to 40% w/w. In some embodiments, the flavoring agent is in an amount of about 10 to 30% w/w. In some embodiments, the flavoring agent is in an amount of about 15% to 25% w/w. In some embodiments, the flavoring agent is in an amount of about 20% w/w. In some embodiments, the flavoring agent has a meat flavor.

In some embodiments, the solid dosage form (e.g., a tablet or capsule) further comprises magnesium stearate. In some embodiments, the magnesium stearate is in an amount of about 0.25% to 5% w/w. In some embodiments, the magnesium stearate is in an amount of about 0.25% to 3% w/w. In some embodiments, the magnesium stearate is in an amount of about 0.25% to 2% w/w. In some embodiments, the magnesium stearate is in an amount of about 0.5% to 1.5% w/w. In some embodiments, the magnesium stearate is in an amount of about 1% w/w.

In some embodiments, a mammal described herein is a companion animal. In some embodiments, the companion animal is a dog or cat. In some embodiments, the companion animal is a dog. In some embodiments, the companion animal is a cat. In some embodiments, a mammal described herein is a dog, cat, horse, cow, pig, rabbit, rodent, sheep, non-human primate, or human. In some embodiments, the mammal is a dog. In some embodiments, the rodent is a mouse or a rat. In some embodiments, the mammal is a human.

In some embodiments, the mammal is a dog of any age. In some embodiments, the mammal is a dog over the age of 7. In some embodiments, the mammal is a dog of 1-8 years old. In some embodiments, the mammal is a dog of 1-3 years old. In some embodiments, the mammal is a dog of 4-8 years old. In some embodiments, the mammal is a dog of at least 7 years old. In some embodiments, the mammal is a dog of at least 9 years old. In some embodiments, the mammal is a dog of at least 10 years old. In some embodiments, the mammal is a dog of at least 11 years old. In some embodiments, the mammal is a dog of at least 12 years old. In some embodiments, the mammal is a dog of at least 13 years old. In some embodiments, the mammal is a dog of at least 14 years old. In some embodiments, the mammal is a dog of at least 15 years old. In some embodiments, the mammal is a dog with signs of aging. In some embodiments, the mammal is a dog that can benefit from a stable glucose level. In some embodiments, the mammal is a dog that is susceptible to a change of glucose level. In some embodiments, the mammal is a dog that is susceptible to glucose elevation. In some embodiments, the mammal is a dog with signs of aging. In some embodiments, the mammal is a dog that can benefit from a lower saturated fatty acid level in the body. In some embodiments, the mammal is a dog that has high saturated fatty acid level in the body. In some embodiments, the mammal is a dog that has high palmitic acid level in the body.

Further Embodiments

In some embodiments, provided herein is a formulation comprising pioglitazone or a pharmaceutically acceptable salt thereof, for use in reducing or delaying mortality due to age-associated diseases in a companion animal, wherein the formulation is administered for at least 2 weeks. In some embodiments, the pioglitazone or a pharmaceutically acceptable salt thereof is pioglitazone hydrochloride. In some embodiments, the pioglitazone or the pharmaceutically acceptable salt thereof is administered at about 2 to 3 mg/kg/day. In some embodiments, the pioglitazone or the pharmaceutically acceptable salt thereof is administered at about 1 to 5 mg/kg/day. In some embodiments, the pioglitazone or the pharmaceutically acceptable salt thereof is administered at an amount of up to 10 mg/kg/day. In some embodiments, the formulation is administered once daily. In some embodiments, the formulation is administered for at least about 4 weeks. In some embodiments, the formulation is administered for at least about 12 weeks. In some embodiments, the formulation is administered for at least about 1 year. In some embodiments, the method comprises decreasing an insulin level in the companion animal. In some embodiments, the insulin level is decreased by at least 5%. In some embodiments, the formulation improves insulin sensitivity. In some embodiments, the insulin sensitivity is measured by an oral glucose tolerance testing assay or by a hyperinsulinemic euglycemic clamp testing assay. In some embodiments, the insulin sensitivity is measured by a shortened or modified oral glucose tolerance testing assay. In some embodiments, the insulin sensitivity is measured by using fasting insulin blood levels. In some embodiments, the formulation decreases a triglyceride level in the companion animal. In some embodiments, the formulation decreases a cholesterol level in the companion animal. In some embodiments, the use further comprises mitigating an age-induced elevation of fatty acid, wherein the fatty acid is aggregated free fatty acids, saturated fatty acids, palmitic acid, linoleic acid, or oleic acid, or any combination thereof. In some embodiments, the companion animal is a dog. In some embodiments, the companion animal is at least 7 years old. In some embodiments, the companion animal is at least 10 years old. In some embodiments, the companion animal is at least 14 pounds. In some embodiments, the formulation comprises about 5% to about 15% of the pioglitazone or the pharmaceutically acceptable salt thereof. In some embodiments, the formulation comprises about 4 mg to about 85 mg of the pioglitazone or the pharmaceutically acceptable salt thereof. In some embodiments, the formulation is in a form of a tablet. In some embodiments, the tablet comprises 18 mg, 54 mg, or 81 mg of the pioglitazone or the pharmaceutically acceptable salt thereof.

In some embodiments, provided herein is a method for reducing or delaying mortality due to age-associated diseases in a companion animal in need thereof, comprising orally administering to the companion animal a therapeutically effective amount of a formulation comprising pioglitazone or a pharmaceutically acceptable salt thereof, wherein the formulation is administered for at least 2 weeks. In some embodiments, the pioglitazone or a pharmaceutically acceptable salt thereof is pioglitazone hydrochloride. In some embodiments, the pioglitazone or the pharmaceutically acceptable salt thereof is administered at about 2 to 3 mg/kg/day. In some embodiments, the pioglitazone or the pharmaceutically acceptable salt thereof is administered at about 1 to 5 mg/kg/day. In some embodiments, the pioglitazone or the pharmaceutically acceptable salt thereof is administered at an amount of up to 10 mg/kg/day. In some embodiments, the formulation is administered once daily. In some embodiments, the formulation is administered for at least about 4 weeks. In some embodiments, the formulation is administered for at least about 12 weeks. In some embodiments, the formulation is administered for at least about 1 year. In some embodiments, the method comprises decreasing an insulin level in the companion animal. In some embodiments, the insulin level is decreased by at least 5%. In some embodiments, the method improves insulin sensitivity. In some embodiments, the insulin sensitivity is measured by an oral glucose tolerance testing assay or by a hyperinsulinemic euglycemic clamp testing assay. In some embodiments, the insulin sensitivity is measured by a shortened or modified oral glucose tolerance testing assay. In some embodiments, the insulin sensitivity is measured by using fasting insulin blood levels. In some embodiments, the method decreases a triglyceride level in the companion animal. In some embodiments, the method decreases a cholesterol level in the companion animal. In some embodiments, the use further comprises mitigating an age-induced elevation of fatty acid, wherein the fatty acid is aggregated free fatty acids, saturated fatty acids, palmitic acid, linoleic acid, or oleic acid, or any combination thereof. In some embodiments, the companion animal is a dog. In some embodiments, the companion animal is at least 7 years old. In some embodiments, the companion animal is at least 10 years old. In some embodiments, the companion animal is at least 14 pounds. In some embodiments, the formulation comprises about 5% to about 15% of the pioglitazone or the pharmaceutically acceptable salt thereof. In some embodiments, the formulation comprises about 4 mg to about 85 mg of the pioglitazone or the pharmaceutically acceptable salt thereof. In some embodiments, the formulation is in a form of a tablet. In some embodiments, the tablet comprises 18 mg, 54 mg, or 81 mg of the pioglitazone or the pharmaceutically acceptable salt thereof.

EXAMPLES

The following illustrative examples are representative of embodiments of the stimulation, systems, and methods described herein and are not meant to be limiting in any way.

Example 1. Metabolic Aging Biomarkers in the HRQL Study

An observational Healthspan study was performed which involved a health related quality of life assessment (HRQL). The study endpoints included owner assessment of Health Related Quality of Life (HRQL), and veterinarian assessment of Physical Examination, Body Condition Score (BCS), Muscle Condition Score, Complete Blood Count, biochemical profile, serum T4 measurement, urinalysis, insulin-like growth factor-1 measurement, and Canine Frailty Index score (CFI). Blood samples were collected to assess serum for fasted insulin and adiponectin levels. DNA samples were also collected. Target demographics were collected within 451 eligible adult dogs, 43.6% of which were mixed breed and 56.4% of which were pure breed. Target age and size of dogs on which enrollment was based is shown below in Table 1. Approximately 451 dogs were evaluated, and about 450 dogs were assessed using the HRQL. Approximately 409 dogs were assessed for fasted insulin levels, and approximately 352 dogs were assessed for adiponectin levels. Bivariate relationships found between insulin and age, insulin and weight, insulin and BCS, insulin and HRQL, and insulin and CFI are shown below in Table 2.

TABLE 1

Demographics of dogs enrolled in HRQL study

| Group | Number of dogs | Demographics |
| --- | --- | --- |
| A: "young, small" | 55 | ≥2 and <6 years of age/<25 lbs. |
| B: "old, small" | 117 | ≥7 years of age/<25 lbs. |
| C: "young, large" | 127 | ≥2 and <6 years of age/>50 lbs. |
| D: "old, large" | 152 | ≥7 years of age/>50 lbs. |
| Total | 451 | — |

TABLE 2

Correlation coefficients evaluating bivariate relationships between factors of interest in HRQL study

| | Variable | rho | p-value |
| --- | --- | --- | --- |
| Demographics | Age (yrs) | 0.18 | <0.001 |
| | Weight (lbs) | 0.07 | 0.156 |
| | Body Condition Score | 0.27 | <0.001 |
| Health Outcomes | HRQL | −0.25 | <0.001 |
| | CFI | 0.10 | 0.034 |

The data from the HRQL study was analyzed using a quantile regression model to estimate joint effects of the variables in Table 2. Multiple median regression was performed using a full main effects model, an interaction model with age multiplied by weight, and an interaction model with age and BCS, shown below in Table 3. A graphical representation of the association between age and standardized log(insulin) for dogs in different weight groups is shown in FIG. 1.

TABLE 3

Multiple median regression results for variables in the HRQL study

| Model | Variables | Effect on standardized log(Insulin) Coefficient (95% CI) | p-value | $R^1$ |
| --- | --- | --- | --- | --- |
| Full main effects model | (Intercept) | −2.22 (−2.94, −1.50) | <0.001 | 0.07 |
| | Age (yrs) | 0.07 (0.04, 0.10) | <0.001 | |
| | Weight (lbs) | 0.00 (0.00, 0.00) | 0.573 | |
| | BCS | 0.30 (0.17, 0.42) | <0.001 | |
| Age × weight | (Intercept) | −2.17 (−3.04, −1.30) | <0.001 | 0.07 |
| | Age (yrs) | 0.06 (0.00, 0.12) | 0.047 | |
| | Weight (lbs) | 0.00 (−0.01, 0.01) | 0.986 | |
| | BCS | 0.30 (0.17, 0.43) | <0.001 | |
| | Age × weight | 0.00 (0.00, 0.00) | 0.775 | |

TABLE 3-continued

Multiple median regression results for variables in the HRQL study

| Model | Variables | Effect on standardized log(Insulin) | | |
|---|---|---|---|---|
| | | Coefficient (95% CI) | p-value | $R^1$ |
| Age × BCS | (Intercept) | −2.88 (−4.41, −1.35) | <0.001 | 0.07 |
| | Age (yrs) | 0.15 (−0.02, 0.32) | 0.086 | |
| | Weight (lbs) | 0.41 (0.14, 0.69) | 0.004 | |
| | BCS | 0.00 (0.00, 0.01) | 0.359 | |
| | Age × BCS | −0.02 (−0.05, 0.02) | 0.345 | |

Fasted insulin levels were examined to determine their relationship with HRQL scores in the Healthspan Study. To determine HRQL, a survey was administered to owners of participants to measure owner perceptions of their dog's quality of life. The questionnaire included about 22 questions concerning the impacts of aging, disease, and clinical management of disease. These questions encompassed inquiries about the dog's behavior for areas including Energetic/Enthusiastic (E/E), Happy/Content (H/C), Active/Comfortable (A/C), and Calm/Relaxed (C/R). The answers to these questions were composited or combined into a single score known as total HRQL. The Davies transformation (Davies 2019) was applied to normalize the scores. Multiple median regression models were used to discern the relationship between insulin and HRQL. Standardized log (insulin) was the primary variable, with age, weight, and BCS as covariates, results of which are shown below in Table 4A and FIG. 2A. Multiple ordinary least squares regression models were used to discern the relationship between insulin and CFI, and its acceleration with age. Standardized log(insulin) and its interaction with age was the primary with, weight and BCS as covariates, results of which are shown in Table 4B and FIG. 2B.

TABLE 4A

Multiple median regression of insulin blood levels with HRQL adjusting for age, weight, and BCS

| Outcome | Variables | Coefficient (95% CI) | p-value | $R^1$ |
|---|---|---|---|---|
| HRQL Total | (Intercept) | 56.66 (51.72, 61.59) | <0.001 | 0.11 |
| | Standardized log(Insulin) | −1.42 (−2.19, −0.64) | <0.001 | |

TABLE 4A-continued

Multiple median regression of insulin blood levels with HRQL adjusting for age, weight, and BCS

| Outcome | Variables | Coefficient (95% CI) | p-value | $R^1$ |
|---|---|---|---|---|
| | Age (yrs) | −0.76 (−0.96, −0.56) | <0.001 | |
| | Weight (lbs) | −0.02 (−0.04, 0.00) | 0.114 | |
| | BCS | −0.05 (−0.91, 0.81) | 0.905 | |

TABLE 4B

Multiple linear regression of interaction effect between age and standardized insulin on standardized CFI.

| Variable | Coefficient (95% CI)[†] | p-value[†] |
|---|---|---|
| Intercept | −0.72 (−1.16, −0.28) | 0.001** |
| Age (yrs) | 0.18 (0.16, 0.20) | <0.001*** |
| Standardized(Insulin) | −0.10 (−0.23, 0.04) | 0.161 |
| Weight (kg) | 0.00 (0.00, 0.01) | 0.222 |
| BCS | −0.14 (−0.22, −0.06) | <0.001*** |
| Age (yrs) × Standardized(Insulin) | 0.02 (0.00, 0.04) | 0.028* |

CFI and insulin are standardized (mean centered and scaled by standard deviation) to facilitation coefficient interpretation.
[†]Standard errors and p-values estimated using Huber-White robust standard errors.

HRQL total was then compared with fasted insulin levels by categorizing the insulin levels into three groups of equal size, or tertiles. The tertiles reflected insulin levels of the lowest third, middle third, and highest third of the sample. Quantile median regression was used to estimate HRQL total based on each insulin tertile, adjusted for covariates including age, weight, and BCS. The 407 insulin measures taken along with HRQL total scores were divided into insulin tertiles, defined as: lowest insulin levels (n=137, range=[2.53 mU/L, 12 mU/L]), highest insulin (n=136, range=[20.9 mU/L, 107 mU/L]), and medium insulin levels (n=136, range=[12 mU/L, 20.9 mU/L]). The tertiles were within normal laboratory reference ranges. Multiple quantile median regression was performed for each insulin tertile group, shown in Table 5 below. The HRQL scores for each insulin tertile group, adjusting for covariates, is shown in FIG. 3A. The HRQL kernel density estimate was analyzed, shown in FIG. 3B. The HRQL total score on the Davies scale as a function of age was analyzed, shown in FIG. 3C.

TABLE 5

Multiple quantile median regression model showing the effects of insulin tertile groups adjusting for age, weight, and BCS as covariates (n = 407).

| Outcome | Variables | Coefficient (95% CI) | p-value | $LRT^1$ p-value |
|---|---|---|---|---|
| HRQL Total | (Intercept) | 57.55 (52.87, 62.23) | <0.001 | |
| | Age (yrs) | −0.76 (−0.97, −0.55) | <0.001 | |
| | Weight (lbs) | −0.01 (−0.04, 0.01) | 0.315 | |
| | BCS | 0.07 (−0.76, 0.90) | 0.873 | |
| | Insulin tertile | | | 0.005 |
| | Low: [2.53 mU/L, 12 mU/L]) | referent | | |
| | Middle: (12 mU/L, 20.9 mU/L] | −2.36 (−4.07, −0.66) | 0.007 | |
| | High: (20.9 mU/L, 107 mU/L] | −3.04 (−5.10, −0.99) | 0.004 | |

The Canine Frailty Index (CFI) scores were based on the medical history and physical examination of the dog participants, performed by a veterinarian. CFI was calculated by summing the response scores and dividing by the total number of questions. A frailty index of 0 denotes a dog that is not at all frail. Lower frailty scores indicated fewer health deficits and lower frailty, while higher frailty scores indicated more health deficits or higher frailty. The CFI score in relation to age was analyzed, shown in FIG. 4A. The CFI score in relation to total HRQL score was analyzed, as shown in FIG. 4B.

Longitudinal data can be collected to further the Healthspan study, including HRQL and mortality data for dog participants. Lipid levels can also be analyzed against HRQL score, CFI score, or both.

Fatty acid quantification was performed using banked serum samples from the study. There were only 61 dogs with sufficient volume to allow for testing to be performed. Levels of free fatty acids (FFA), saturated fatty acids (SFA), palmitic acid (PA, a 16:0 saturated fatty acid), oleic acid (OA, a 18:1n9 monounsaturated fatty acid) and linoleic acid (LA, a 18:2n6 polyunsaturated fatty acid) were measured using gas chromatography-mass spectrometry (GC-MS; Metabolon, Inc). One dog of the 61 had missing insulin concentration values and is not included in any analyses or models involving insulin.

Age was significantly positively associated with all fatty acid species and aggregates measured (p<0.05, Table 6). Each fatty acid species and aggregate in relation to age are presented in FIG. 4C.

P-values estimated using Huber-White robust variance estimator.

Multiple linear regression was used to estimate age-related changes in adiponectin after adjusting for covariates (weight, and BCS). Adiponectin was natural-log transformed to address issues of non-normality. Adiponectin significantly decreases with age (slope and 95% CI=−0.09 (−0.11, −0.07), p-value<0.001), adjusting for effects of body size, weight, and BCS. These results indicate that every year increase in age is associated with a −0.09 increase in ln(adiponectin). Log transformed outcomes can be interpreted in terms of percent change, and therefore every year increase in age is associated with a 100*−0.09=9% reduction in adiponectin. FIG. 4D shows observed and predicted adiponectin values change across age. To estimate the covariate-adjusted association between fatty acids and adiponectin, a multiple regression model was used to estimate the relationship between fatty acids and adiponectin accounting for effects of age, weight and BCS. To find the most parsimonious model, covariates which had a p<0.10 across all models were retained. Huber-White robust standard errors were used to address issues of heteroscedasticity. As scales differ across fatty acids, other covariates, and adiponectin, fatty acids and adiponectin were standardized (mean=0, SD=1). All fatty acid species and concentrations were significantly negatively associated with adiponectin (Table 7, all p<0.05). Coefficient estimates can be interpreted as: for every standard deviation increase in fatty acid concentration, there is a −0.25 to −0.44 standard deviation decrease in adiponectin. FIG. 4E shows observed and covariate-adjusted predicted relationships on their natural scales.

TABLE 6

Multiple regression estimating main effects of age and BCS in association with FFA, SFA, PA, OA and LA.

| Standardized Outcome | Predictor | Coefficient (95% CI) | p-value | Overall p-value | $R^2$ |
|---|---|---|---|---|---|
| FFA | Intercept | −2.32 (−3.41, −1.23) | <0.001*** | 0.007** | 0.157 |
| | Age (yrs) | 0.10 (0.04, 0.17) | 0.002** | | |
| | BCS | 0.26 (0.07, 0.45) | 0.008** | | |
| SFA | Intercept | −2.72 (−3.93, −1.51) | <0.001*** | 0.003** | 0.183 |
| | Age (yrs) | 0.10 (0.04, 0.17) | 0.002** | | |
| | BCS | 0.33 (0.13, 0.54) | 0.002** | | |
| Palmitic acid (16:0) | Intercept | −1.84 (−3.04, −0.64) | 0.003** | 0.011* | 0.145 |
| | Age (yrs) | 0.11 (0.04, 0.18) | 0.003** | | |
| | BCS | 0.17 (−0.03, 0.37) | 0.088 | | |
| Oleic acid (18:1n9) | Intercept | −1.44 (−2.90, 0.01) | 0.052 | 0.044* | 0.102 |
| | Age (yrs) | 0.09 (0.01, 0.17) | 0.021* | | |
| | BCS | 0.13 (−0.12, 0.37) | 0.305 | | |
| Linoleic acid (18:2n6) | Intercept | −2.13 (−3.39, −0.86) | 0.001** | 0.018* | 0.129 |
| | Age (yrs) | 0.09 (0.03, 0.16) | 0.006** | | |
| | BCS | 0.24 (0.04, 0.45) | 0.021* | | |

Fatty acid concentrations standardized (mean centered and scaled by standard deviation).

TABLE 7

Multiple regression testing the covariate-adjusted relationships between FFA, SFA, PA, OA and LA and adiponectin.

| Model | Variable | Coefficient (95% CI) | p-value | Overall p-value | $R^2$ |
|---|---|---|---|---|---|
| Model 1 | Intercept | 1.13 (−0.37, 2.62) | 0.137 | <0.001*** | 0.324 |
| | FFA | −0.41 (−0.59, −0.23) | <0.001*** | | |
| | Age (yrs) | −0.06 (−0.12, 0.01) | 0.071 | | |
| | Weight (kgs) | 0.02 (0.00, 0.04) | 0.099 | | |
| | BCS | −0.20 (−0.47, 0.07) | 0.146 | | |
| Model 2 | Intercept | 0.86 (−0.60, 2.31) | 0.243 | <0.001*** | 0.344 |
| | SFA | −0.44 (−0.64, −0.24) | <0.001*** | | |
| | Age (yrs) | −0.05 (−0.12, 0.01) | 0.092 | | |
| | Weight (kgs) | 0.02 (0.00, 0.04) | 0.091 | | |
| | BCS | −0.16 (−0.42, 0.10) | 0.224 | | |
| Model 3 | Intercept | 1.40 (−0.16, 2.96) | 0.078 | 0.001** | 0.286 |
| | Palmitic acid (16:0) | −0.34 (−0.54, −0.14) | 0.002** | | |
| | Age (yrs) | −0.06 (−0.13, 0.00) | 0.050* | | |
| | Weight (kgs) | 0.02 (−0.01, 0.04) | 0.157 | | |
| | BCS | −0.23 (−0.51, 0.05) | 0.111 | | |
| Model 4 | Intercept | 1.68 (−0.10, 3.47) | 0.064 | 0.005** | 0.243 |
| | Oleic acid (18:1n9) | −0.25 (−0.48, −0.03) | 0.029* | | |
| | Age (yrs) | −0.08 (−0.14, −0.01) | 0.023* | | |
| | Weight (kgs) | 0.02 (−0.01, 0.04) | 0.183 | | |
| | BCS | −0.26 (−0.59, 0.07) | 0.115 | | |
| Model 5 | Intercept | 1.27 (−0.11, 2.65) | 0.071 | <0.001*** | 0.312 |
| | Linoleic acid (18:2n6) | −0.39 (−0.63, −0.15) | 0.002** | | |
| | Age (yrs) | −0.06 (−0.13, 0.00) | 0.045* | | |
| | Weight (kgs) | 0.02 (0.00, 0.04) | 0.086 | | |
| | BCS | −0.22 (−0.47, 0.03) | 0.086 | | |

Adiponectin and each fatty acid concentration are standardized (mean = 0, SD = 1).
*p < 0.05,
**p < 0.01,
***p < 0.001
P-values estimated using Huber-White robust variance estimator.

Multiple linear regression was used to estimate relationship between fatty acid species and aggregates with CFI. Both main effects of fatty acids as well as their interaction with age were tested.

Fatty acid measures were not significantly associated with CFI in main effects models adjusting for age. However, we detected significant interaction effects between all fatty acids (free fatty acids, saturated fatty acids, palmitic acid, oleic acid and linoleic acid) and age (p<0.05, Table 8, FIG. 4F). All coefficients for the interactions between age and fatty acid measures were >0, suggesting that the effects appear to be stronger in older dogs.

TABLE 8

Multiple regression testing the interactions between FFA, SFA, PA, OA and LA age on CFI scores.

| Fatty acid tested | Variable | Coefficient (95% CI) | p-value | Overall p-value | $R^2$ |
|---|---|---|---|---|---|
| FFA | Intercept | −0.08 (−0.13, −0.03) | 0.002** | <0.001*** | 0.537 |
| | FFA | −0.07 (−0.12, −0.02) | 0.008** | | |
| | Age (yrs) | 0.02 (0.01, 0.03) | <0.001*** | | |
| | FFA × Age (yrs) | 0.01 (0.00, 0.01) | 0.007** | | |
| SFA | Intercept | −0.08 (−0.13, −0.03) | 0.003** | <0.001*** | 0.524 |
| | SFA | −0.06 (−0.11, −0.01) | 0.028* | | |
| | Age (yrs) | 0.02 (0.01, 0.03) | <0.001*** | | |
| | SFA × Age (yrs) | 0.01 (0.00, 0.01) | 0.037* | | |
| Palmitic acid (16:0) | Intercept | −0.08 (−0.13, −0.02) | 0.005** | <0.001*** | 0.513 |
| | Palmitic acid (16:0) | −0.06 (−0.12, 0.00) | 0.045* | | |
| | Age (yrs) | 0.02 (0.01, 0.03) | <0.001*** | | |
| | Palmitic acid (16:0) × Age (yrs) | 0.01 (0.00, 0.01) | 0.040* | | |
| Oleic acid (18:1n9) | Intercept | −0.07 (−0.12, −0.02) | 0.007** | <0.001*** | 0.527 |
| | Oleic acid (18:1n9) | −0.05 (−0.10, −0.01) | 0.017* | | |
| | Age (yrs) | 0.02 (0.01, 0.02) | <0.001*** | | |
| | Oleic acid (18:1n9) × Age (yrs) | 0.01 (0.00, 0.01) | 0.002** | | |

TABLE 8-continued

Multiple regression testing the interactions between
FFA, SFA, PA, OA and LA age on CFI scores.

| Fatty acid tested | Variable | Coefficient (95% CI) | p-value | Overall p-value | $R^2$ |
|---|---|---|---|---|---|
| Linoleic acid (18:2n6) | Intercept | −0.09 (−0.14, −0.04) | 0.001** | | |
| | Linoleic acid (18:2n6) | −0.08 (−0.14, −0.03) | 0.003** | | |
| | Age (yrs) | 0.02 (0.01, 0.03) | <0.001*** | | |
| | Linoleic acid (18:2n6) × Age (yrs) | 0.01 (0.00, 0.01) | 0.008** | | |

Each fatty acid concentrated is standardized (mean = 0, SD = 1).
P-values estimated using Huber-White robust variance estimator Multiple regression was used to estimate covariate adjusted relationships between adiponectin and CFI, testing for main effects of adiponectin as well as interactions with age. CFI was treated as the outcome and adiponectin was treated as the primary predictor of interest. Adiponectin was natural-log transformed to account for non-linearity. Covariates included age, weight and BCS. Covariate-adjusted relationships (i.e., slope) between adiponectin and CFI were estimated using marginal linear trends.

As adiponectin and CFI scales differ dramatically, standardized regression coefficients are reported in Table 9. After adjusting for age, weight and BCS, the main effect of adiponectin on CFI was not statistically significant (Coefficient (95% CI)=0.01 (−0.10, 0.13), p=0.797, Table 9). However, this is likely due to the presence of a significant interaction effect between adiponectin and age (Coefficient for interaction term (95% CI)=−0.03 (−0.06, 0.00), p=0.026, Table 9), suggesting reductions in CFI associated with higher adiponectin become stronger with age. Estimated linear trends from the interaction model testing alongside observed data are presented in FIG. 4G. FIG. 4G, panel A shows all observed and predicted values together, while panel B shows these same data stratified into age groups. These analyses show that the relationship between adiponectin and CFI is relatively flat until dogs reach around 10 years of age, where we start to see reductions in CFI associated with increases in adiponectin (FIG. 4G, panel B). Results of these analyses provide evidence that CFI declines with increased adiponectin, particularly in older dogs.

Example 2. Treatment with Pioglitazone, Effect on Glucose and Insulin

This study determines if Pioglitazone can reverse the development of High Fat Diet (HFD)-induced insulin resistance and decline of metabolic health in dogs by improving insulin sensitivity as demonstrated through Oral Glucose Tolerance Testing (OGTT) results and circulating analytes after 5 weeks of HFD and again after 7 weeks of pioglitazone (1 mg/kg/day or 2 mg/kg/day) treatment.

Pioglitazone activates peroxisome proliferator-activated receptor gamma (PPARγ) and stimulates the release of adiponectin from the adipose tissue. It is hypothesized that this drug would mitigate or reverse impairments in hyperinsulinemia and insulin sensitivity induced by chronic HFD feeding. Interventions that improve glucose tolerance and reduce insulin resistance (i.e., caloric restriction, metformin) increase the health-span (the years of life spent disease-free) and lifespan of several model organisms, including rodents, dogs and monkeys.

This study aims to provide evidence that pioglitazone was metabolically protective (i.e., mitigated and or/reversed the development of clinical manifestation of insulin resistance) when used as an intervention after HFD-induced metabolic dysfunction had already occurred.

This 17-week HFD design, metabolic reversal study was conducted on 4 groups of 12 Beagle dogs each. All dogs included in the study were males, aged 3-7 years, weighing 12.05-22.95 kg. After 63 days (9 weeks) of normal diet or

TABLE 9

Multiple regression testing the covariate-adjusted main effect relationship
between adiponectin and CFI and interactions with age.

| Model | Variable | Coefficient (95% CI) | p-value | Overall p-value | $R^2$ |
|---|---|---|---|---|---|
| Main effect | Intercept | −0.76 (−1.33, −0.20) | 0.008** | <0.001*** | 0.528 |
| | ln(Adiponectin (ng/mL)) | 0.01 (−0.10, 0.13) | 0.797 | | |
| | Age (yrs) | 0.19 (0.16, 0.22) | <0.001*** | | |
| | BCS | −0.14 (−0.24, −0.05) | 0.004** | | |
| | Weight (kgs) | 0.00 (0.00, 0.01) | 0.246 | | |
| Interaction with age | Intercept | −0.90 (−1.43, −0.38) | <0.001*** | <0.001*** | 0.542 |
| | ln(Adiponectin (ng/mL)) | 0.28 (0.09, 0.46) | 0.003** | | |
| | Age (yrs) | 0.19 (0.16, 0.22) | <0.001*** | | |
| | BCS | −0.13 (−0.21, −0.04) | 0.005** | | |
| | Weight (kgs) | 0.00 (0.00, 0.01) | 0.234 | | |
| | ln(Adiponectin (ng/ml)) × Age (yrs) | −0.03 (−0.06, 0.00) | 0.026* | | |

P-values estimated using Huber-White robust variance estimator. CFI and adiponectin are standardized (mean centered and scaled by standard deviation) to facilitation coefficient interpretation.
*p < 0.05,
**p < 0.01,
***p < 0.001

HFD-feeding, Placebo was administered daily by mouth to Groups 1 and 2 while pioglitazone was administered daily by mouth to Groups 3 and 4. The dogs tolerated Placebo/pioglitazone administration well.

Clinical examinations and body weights were conducted throughout the study to monitor the health of the animals. Daily general health observations and faecal examinations were also performed for the duration of the study.

Animals were fed their daily food ration (g) as a split ration. Each feeding (AM or PM) consisted of approximately half the animal's daily food ration and was offered approximately 4 hours apart. Dogs were given approximately 2 hours to consume each ration and any remaining food was weighed back for each feeding.

All dogs were fed ad libitum "normal diet" (ND) consisting of 55% fat for all baseline measurements prior to study start. Prior to the study start, dogs were randomly assigned to either ND or HFD consisting of 74% fat, on which they remained for approximately 9 weeks. After 9 weeks, HFD-fed animals were further randomized to treatment groups prior to dosing based on fasting insulin levels as the primary factor and total body weight as the secondary factor. Dogs in the ND group were continued on ND through the conclusion of the study. Blood collections for Chemistry, Haematology, Triglycerides, Cholesterol, Metabolomics and Lipidomics, efficacy Biomarkers (Adiponectin, Fasting Insulin, and Leptin), pioglitazone pharmacokinetics, Cytokines (IL-6 and TNFa) and Non-esterified fatty acids (NEFA) were performed throughout the study to assess the diet and drug-related effects on markers of safety and metabolic function. Baseline (Day −56) and Pre-Treatment (Day 0) readings of each parameter were compared to Treatment (Day 57) readings.

OGTTs were performed during the Pre-Treatment (Day −14) and Treatment (Day 42) phases to assess glucose and insulin kinetics and insulin sensitivity. OGTTs were carried out as previously described by Coate et al., 2010. Briefly, dogs were fasting overnight prior to conducting the procedure. Blood was sampled and serum and plasma separated at −20 and 0 minutes pre-glucose bolus to establish fasting glucose and insulin values. At 0 minutes (t=0), a glucose bolus (0.9 g/kg, p.o.) was delivered. Blood was collected at 5, 10, 20, 30, 40, 50, 60, 70, 80, 90, 120, 180 and 240 minutes post-glucose bolus. Serum was then analyzed for glucose and plasma was analyzed for insulin levels at each time point.

Body composition and resting energy expenditure was measured at Pre-Treatment (Day −21), when the dogs had been on ND or HFD for 5 weeks, and Treatment (Day 49) timepoints using blood samples taken following systemic administration of $D_2O$ (deuterium oxide) and $^2H_2^{18}O$ (doubly labelled water). Dogs were fasted for a minimum of 12 hours prior to the first blood draw of each sampling day. $D_2O$ and $^2H_2^{18}O$ were prepared with autoclaved glassware and utensils, weighed out separately, and drawn into separate syringes. Body weights were taken the day of sampling and prepared $D_2O$ and $^2H_2^{18}O$ were drawn into separate syringes per animal and weighed to the third decimal place prior to administration. Two milliliters (mL) of blood was collected prior to administration of 50 mg/kg of 99% $D_2O$ and 150 mg/kg of 97% $^2H_2^{18}O$ via oral syringe. Blood samples were then collected at 2 h, 24 h, 72 h, 120 h and 168 h after initial $D_2O+^2H_2^{18}O$ administration. Following collection, blood was plasma separated in K2EDTA tubes and were stored at −80° C. until analysis.

Baseline or Pre-Treatment readings for all parameters (blood tests, body weight, food consumption, OGTT, body composition/energy expenditure) were established per animal and per group and these results were compared to Treatment results. Individual and summary statistics, arithmetic means, percentage change and within and between group comparisons were done.

The fasted glucose measurements and fasted insulin measurements for each group of subjects were analyzed, as shown in FIG. 5A (Fasted Glucose) and FIG. 5B (Fasted Insulin). After subjects were administered Pioglitazone, the AUC values of glucose and insulin in response to treatment were analyzed, as shown in FIG. 5C and FIG. 5D.

This study demonstrates that treatment with pioglitazone has no impact on fasting glucose measurements, as well as no impact on glucose excursion during glucose tolerance test (FIG. 5A and FIG. 5C). Additionally, the study demonstrates that pioglitazone influences fasting insulin and insulin response to glucose independent of any effect on glucose (FIG. 5B and FIG. 5C). This finding is a departure from the literature which suggests that PPARγ activators (i.e. pioglitazone) promote metabolic health by promoting glucose excursion and whole body insulin sensitivity, whereas these studies demonstrate the metabolic benefit is independent of glucose in dogs.

Example 3. Treatment with Pioglitazone, Effect on Deleterious Fatty Acids

This study demonstrates that pioglitazone dose dependently regulates the levels of metabolically deleterious fatty acids in dogs. These fatty acids include all aggregated saturated fatty acids (SFAs), palmitic acid, linoleic acid and oleic acid. Infusion of these lipids exogenously in dogs (Intralipid 20%, containing linoleic [44-62%], oleic [19-30%], palmitic [7-14%], linolenic [4-11%] and stearic acid [1.4-5.5%]) can recapitulate several aspects of human metabolic dysfunction and impair muscle and hepatic insulin sensitivity.

Subjects were administered Pioglitazone treatment, and fatty acids analysis was performed from blood samples of subjects. Fatty acids were detected and analyzed by species and quantified. The effects of Pioglitazone treatment on saturated fatty acids was analyzed, as shown in FIG. 6A. Additionally, the effects of Pioglitazone on each different species of fatty acids were analyzed, as shown in FIG. 6B (Palmitic Acid), FIG. 6C (Linoleic Acid), and FIG. 6D (Oleic Acid). Fatty acids were measured at baseline, pre-treatment with Pioglitazone, and post-treatment with Pioglitazone as shown in FIG. 6E.

SFAs are associated with metabolic dysfunction and insulin resistance. It is demonstrated that pioglitazone-treatment reversed HFD-induced elevation of SFA (FIG. 6A). Similarly, pioglitazone treatment results in decreases in palmitic acid, one of the largest individual lipid species that contributes to the SFA pool (FIG. 6B). Palmitic acid is known to directly impair insulin signaling in the liver and muscle, thus a specific reduction in palmitic acid induced by pioglitazone administration further supports that TI improves overall and species-specific lipid profiles following HFD-induced metabolic dysfunction. These data are the first to show improvement in fatty acid levels with pioglitazone treatment in dogs.

This study also demonstrates that measuring FFA's using a clinical diagnostic assay (NEFA) is: (1) not able to distinguish between fatty acid species and (2) not representative of fatty acid levels when measured by the more sensitive direct measured GC-MS based approach. Indirect measurement from the spectrophotometer-based clinical assay does not detect any significant changes, nor does it even mirror the trends observed with direct measurement. These data demonstrate that clinically used fatty acid quantification tools are not sensitive enough to detect changes that are physiologically relevant (FIG. 6E).

Example 4. Treatment with Pioglitazone, Effect on HFD Metabolic Dysfunction

The study generates the following conclusions. The dogs on the HFD showed increased food consumption and body weight (p<0.05; not shown), which resulted in increased fat mass (p<0.05; not shown) and significant alterations in their metabolic composition. The observed changes included significant increases in cholesterol, triglycerides, FFAs, SFAs, leptin and resting energy expenditure. In contrast, the HFD had no demonstrable effect on adiponectin, cytokines and NEFA levels.

Importantly, the HFD induced a state of hyperinsulinemia as denoted by a significant increase in fasted insulin and no change in fasted glucose. This HFD-induced hyperinsulinemic state was complemented by functional data from the OGTT assay demonstrating a significant increase in insulin AUC and Cmax levels. Taken together with the biochemical profile (e.g. significantly increased circulating triglycerides and cholesterol), these changes indicate that the HFD successfully induced a state of severe and clinically relevant metabolic dysfunction. In the HFD-fed pioglitazone treated dogs, we observe several lines of evidence showing that pioglitazone mitigates or reverses metabolic impairments associated with 17 weeks of HFD when administered as an intervention following 9 weeks of HFD-feeding. First, we note evidence that pioglitazone significantly upregulates adiponectin, the putative biomarker of target engagement and known insulin sensitizing protein. Second, pioglitazone treatment successfully mitigated further HFD-induced hyperinsulinemia, hyperlipidemia (e.g. significantly reduced circulating triglycerides and cholesterol) and normalized detrimental fatty acid profiles compared to the HFD-fed placebo group. Third, HFD-fed dogs treated with pioglitazone displayed markers of increased insulin sensitivity, as measured by reduced insulin secretion in response to glucose measured by assessing insulin AUC after dosing compared to the HFD-fed placebo group. Lastly, we note that treatment with the pioglitazone induced a change in body composition via increases in fat mass compared to the HFD-fed placebo group. Histological examination of the visceral and subcutaneous adipose tissue revealed that pioglitazone treatment decreased the size of adipocytes in the viscera, suggesting a relative increase in subcutaneous adipose. It is also important to note that pioglitazone exerted metabolically protective and body composition effects without any effects on food consumption, caloric intake or leptin levels, indicating that pioglitazone improved metabolic function through mechanisms independent of appetite or weight loss. Taken together, these data demonstrate that the HFD canine model induces a profound state of metabolic dysfunction which can be mitigated, and in some cases reversed, by interventional pioglitazone administration, strongly supporting the use of pioglitazone as a therapeutic strategy for improving/preserving metabolic function in dogs.

Example 5. Treatment with Pioglitazone to Prevent Metabolic Dysfunction Study Design The purpose of this study was to assess the impact of pioglitazone on HFD-induced insulin resistance, hyperinsulinemia and fatty acid regulation in beagle dogs. We hypothesized that administration of pioglitazone to HFD-fed, metabolically dysfunctional dogs would (1) upregulate adiponectin levels (2) protect whole body insulin sensitivity as measured by an oral glucose tolerance test (OGTT) and hyperinsulinemic euglycemic clamp (HIEG) and (3) prevent increased deleterious fatty acid levels in the face of a HFD.

Study Design: Twenty four animals (between 1 and 2 years old) were acclimated for at least 2 weeks and surgically implanted with a femoral artery catheter under anesthesia. 2 baseline tests were performed before any treatment: an OGTT and a HIEG clamp.

The dogs were then randomly assigned to one of 3 groups: a placebo group (n=8) that received an empty capsule daily, a group that received 1 mg/kg pioglitazone in the form of a 15 mg pill (Dose 1, n=8), a group that received 2 mg/kg pioglitazone in the form of 215 mg pills (Dose 2, n=8). Pioglitazone pills (Actos, Teva Pharmaceuticals, NJ) were given daily immediately before feeding and flushed with 5 mL of water.

Two weeks after the treatment started, all the animals were put on a HFD (Research Diet 5SQ1, Test Diet from Purina). On Day 46 and 56 after the start of the pioglitazone treatment, the animals were given an OGTT and a HIEG clamp respectively to compare to their baseline metabolic response. On day 46 and 56, placebo and pioglitazone were given one hour before the gavage and one hour before the start of the somatostatin infusion. The same amount of glucose as the initial OGTT study was given and the same rate of insulin and hormone was given during the clamp despite the gain weight of the animal, because we know that the animals mainly gain fat, a tissue that is unresponsive to the level of insulin.

Additionally, every 2 weeks, blood was harvested from each animal for multiple chemical measurements (Adiponectin, Superchem panel (performed by Antech Diagnostics)) before pioglitazone administration and feeding. Pioglitazone was also measured every 2 weeks in the serum, harvested 1 hour after pill administration and feeding.

This study generates the following conclusions: Consuming a HFD for 5-6 weeks caused metabolic dysfunction in beagle dogs. This was manifest in all 8 dogs as indicated by 1) a 25% increase in fasting insulin; 2) fasting FFAs (20%) were slightly elevated suggesting a mild adipose abnormality; 3) the insulin response during the OGTT was increased by 39% thus compensating for the defect caused by HFD feeding; 4) the hyperinsulinemic, euglycemic clamp data showed that there was a 25% decrease in the GIR and a 37% drop in Rd after 6 weeks of high fat feeding in the presence of identical insulin, glucose and glucagon levels; and 5) after 6 weeks of HFD feeding the fasting FFA levels were increased by 25% and the ability of insulin to inhibit lipolysis was significantly reduced.

In both pioglitazone treated groups, there was a significant increase of circulating adiponectin after the start of daily pioglitazone administration (by Day 14). The placebo group showed a significant although smaller and transient increase of adiponectin on Day 28. The rise in the pioglitazone groups was larger and more sustained than in the placebo group. 1) In both pioglitazone treated groups, the insulin response during the OGTT was reduced compared to the placebo group. Thus, pioglitazone was able to normalize glucose metabolism without increasing insulin secretion. 2) The glucose clamp data (excluding the 4 dogs in which the insulins were not comparable in the Day -1 and Day 56 clamps possibly due to enhanced insulin clearance rates) both doses of pioglitazone were able to overcome the defect in GIR and Rd caused by the HFD. 3) In the clamp experiments, pioglitazone reduced the fasting FFA levels and improved the inhibition of lipolysis.

Example 6. Treatment with Pioglitazone on Aging Biomarkers

The effects of Pioglitazone aging biomarkers in client-owned dogs can be determined. Approximately 60 dogs are enrolled and randomized into two groups at a 3:1 ratio of treatment to control. Dogs can be screened on visit 1, which is 7 days before the study, and complete screening on visit 2, Day 0 of the study. The treatment can be randomized with dosing beginning on Day 0. The study has participant dogs enrolled for approximately 3 months, with evaluation visits about every 30 days for biomarker measurements and safety evaluations. The HRQL, CFI, insulin, and FFA blood levels are measured.

Commercial Pioglitazone can also be used to measure the effect of Pioglitazone treatment on insulin levels and FFA data with dogs on a HFD.

Study Procedures and Assessments

To assess Owner-perceived quality of life, the VetMetrica HRQL instrument will be used, a web-based Owner-completed questionnaire that can be completed through the Prelude website or ePRO application. The HRQL is a validated tool that assesses four domains of a dog's quality of life: Energetic/Enthusiastic (E/E), Happy/Content (H/C), Active/Comfortable (A/C), and Calm/Relaxed (C/R). HRQL detects age-related differences and Owner-perceived sickness in dogs.

The first HRQL survey will be completed by the Owner at the screening visit/study visit 1 and before the Investigator performs the Physical Exam (PE). At study visits 4-6, the HRQL questionnaire must always be completed by the Owner up to seven (7) days before the scheduled visit date or at the visit before the PE is performed. The Investigator will verify that the HRQL survey was done before each PE on the Physical Exam eCRF. Owners will not be able to review or access previously completed HRQL surveys. Owner access to the visit-associated HRQL survey is removed after the visit-associated Physical Exam eCRF has been completed.

The Canine Frailty Index (CFI) is a veterinarian assessment with 33 questions focusing on the dog's health and clinical data. The responses will be recorded on the visit-associated CFI eCRF within the eDC. It will require initiation by the Investigator or examining veterinarian on the day of the PE and completion after receipt and review of the clinical pathology results from the dog.

The first CFI will be initiated at the screening visit/study visit 1 and completed on or before study visit 2. This assessment will then be started at study visits 4-6 and completed after a review of blood work results for the duration of the study.

A thorough medical history will be obtained on all dogs at the screening visit/study visit 1 and each study visit (except study visit 3) to document any changes or AEs. To distinguish pre-existing or ongoing medical conditions from potential Adverse Events (AEs) that occur during the study, it is required to perform a thorough review of the dog's health, along with any changes that have developed since the last visit and last PE. The reporting will include a brief description of each medical condition, date of diagnosis (if known), resolution date (if resolved), or ongoing status (if ongoing). All medical history, including medical conditions which are ongoing and not resolved, will be noted in the Medical History Log.

PEs will be performed at each study visit (except study visits 2-3) starting with the screening visit/study visit 1. PEs will be a subjective assessment of general appearance, attitude, otic, ocular, oral/mucous membrane color, respiratory, cardiovascular, gastrointestinal, neurologic, musculoskeletal, integumentary, and genitourinary systems. PE should include a record of temperature (° F.), heart rate (beats per minute), respiratory rate (breaths per minute), and mucous membrane (MM) color. Results of the PE will be documented on the visit-associated Physical Exam eCRF at the time of performance for each dog. All abnormalities will be documented in the Physical Exam eCRF, and any information about pre-existing, ongoing, and new conditions will be documented in the Medical History Log. Abnormalities discovered after initiation of dosing at study visit 2 will be recorded as AEs or SAEs (per Section 15) on the Adverse Event (AE) Log or Serious Adverse Event (SAE) Form as well as the Medical History Log.

As part of the PE, body weight will be measured to the nearest tenths on a calibrated scale and recorded in kilograms (kg) or pounds (lbs.). The dog's initial weight will be recorded on the visit 1 Physical Exam eCRF, which will auto-populate to the Study Drug: Subject Log to provide the proper dose of the Investigational Veterinary Product/Control Product (IVP/CP). The IVP/CP dose will stay the same throughout the study, even if the dog's weight changes. Body Condition Score (BCS) will be measured as a part of the PE. The Nestle PURINA Body Condition System will be utilized to assess BCS. The BCS uses visualization and palpation to assess the dog's general shape and the amount of fat coverage over the ribs, spine, and hips. This BCS is on a scale of 1-9; a score of 9 is a significantly overweight dog, and a score of 1 is an extremely underweight dog. The BCS will be recorded on the Physical Exam eCRF utilizing the supplementary BCS Guide, as needed.

Muscle Condition Score (MCS) will also be measured as a part of the PE. The World Small Animal Veterinary Association (WSAVA) instrument will be utilized to assess MCS. The MCS uses visualization and palpation of the spine, scapulae, skull, and wings of the ilia. Muscle condition is graded as normal, mild loss, moderate loss, or severe loss. The MCS will be recorded on the Physical Exam eCRF utilizing the supplementary MCS Guide, as needed. Dogs will have blood samples collected via venipuncture for hematology and biochemistry at every study visit (except study visits 2 and 3) starting at the screening visit/study visit 1. The maximum volume of blood collected will not exceed safe limits for the smallest dogs eligible to enroll in the study.

All samples collected and associated sample collection information will be recorded on the visit-associated Clinical Pathology eCRF and IDEXX Lab Forms. Care will be taken in venipuncture technique to limit hemolysis.

Urine for urinalysis will also be collected at every study visit (except study visits 2 and 3) starting at the screening visit/study visit 1. The method of urine collection can be free catch, cystocentesis, or urinary catheterization at the discretion of the examining veterinarian. The Owner may also collect the dog's urine sample and bring it to the study site if it is collected within 2 hours before the appointment time. The collection method will be recorded on the IDEXX Lab Form. Likewise, failure to collect a urine sample will be annotated and recorded as a protocol deviation in the Protocol Deviation: Subject Level Form.

The following blood and urine tests will be performed and analyzed at the Central Laboratory (IDEXX):

Hematology, Comprehensive Blood Count (CBC). Absolute Reticulocyte, Anisocytosis, Band (% and count), Basophil (% and count), Eosinophils (% and count), Hematocrit (HCT), Heinz bodies, Hemoglobin (HGB), Lymphocyte (% and count), Mean Cell Hemoglobin (MCH), Mean Cell Hemoglobin Concentration (MCHC), Mean Cell Volume (MCV), Metamyelocyte (% and count), Monocyte (% and count), Myelocyte (% and count), Neutrophil (% and count), Nucleated Red Blood Cells (RBC), Platelet count, Platelet estimate, Poikilocytosis, Polychromasia, Promyelocyte (% and count), Red Blood Cells (RBC), Reticulocyte, Unclassified, White Blood Cells (WBC).

Biochemistry, Comprehensive Chemistry. Albumin/Globulin (ALB/GLOB) ratio, Albumin, Alkaline Phosphatase (ALP), Alanine Transferase (ALT), Aspartate transaminase (AST), Bicarbonate, Bilirubin—Conjugated, Bilirubin—Unconjugated, Blood Urea Nitrogen (BUN), BUN/Creatinine Ratio, Calcium, Chloride, Cholesterol, Creatine kinase, Creatinine, Gamma glutamyl transferase (GGT), Globulin, Glucose, Hemolysis Index, Lactate Dehydrogenase (LDH), Lipemia Index, Na/K Ratio, Phosphorus, Potassium, Sodium, Total Bilirubin, Total Protein, Triglycerides, LDL, HDL.

Fasting insulin. Dogs should be fasted for 12 hours before blood draw for fasting insulin. If the dog is not fasted before the blood collection, the Protocol Deviation: Subject Level eCRF must be completed.

Total T4—Uranalysis Dipstick, Microscopic Sediment Evaluation. Bacteria, Bilirubin, Blood, Casts, Clarity, Color, Crystals, Epithelial cells, Glucose, Ketones, Mucus, pH, Protein, RBC, Specific Gravity, Urobilinogen, Volume, WBC Upon receipt of the clinical pathology results in the eDC system, the Investigator or examining veterinarian will review and evaluate the results in a timely manner. They will assess the clinical significance of abnormal or out-of-range values as clinically significant (CS) or not clinically significant (NCS). CS results will be recorded in the eDC, and any pre-existing or ongoing CS laboratory parameters or the corresponding disease/condition should be added to the Medical History Log and Adverse Event (AE) Log (if the CS parameter was found after initiation of IVP/CP dosing on day 0). Plasma collection for banking. A separate green top tube will be collected and submitted to IDEXX for banking at every study visit (except study visits 2 and 3), starting at the screening visit/study visit 1.

PAXgene mRNA Tube Collection. The PAXgene blood tubes will be included in the provided lab supplies. They will be collected at every study visit (except study visits 2 and 3), starting at the screening visit/study visit 1. This study will not use these blood samples to evaluate exploratory biomarkers. These samples will be labeled and sent with the other blood tubes to IDEXX.

At the screening visit/study visit, 1 only whole blood for DNA will be collected from the same EDTA lavender top tube used for the CBC sample. These blood samples will not be used in this study but will be banked for use on future DNA projects by the Sponsor. These samples will be labeled and sent with the other blood tubes to IDEXX.

DNA Collection—Saliva Swab/Cheek Swab. At the screening visit/study visit 1 only, saliva or cheek swabs for DNA sampling will be collected via PERFORMAgene PG-100 non-invasive swab kits following manufacturer instructions. The study subject must not have eaten at least 30 minutes before or have drunk at least 10 minutes before the saliva swab is taken. Care should be taken, so the collection sponge doesn't scrape the teeth or get bitten by the subject.

After collection, swabs will be stored at room temperature in a secure location without significant temperature fluctuations at the study site. The Sponsor-assigned study Clinical Research Associate (CRA) will then ship or assist with shipment to a storage repository. Saliva swabs will be used in future DNA projects by the Sponsor.

Unscheduled Visits. Throughout the course of the study, enrolled dogs may present to the Investigator or study site for new clinical signs that may arise. These appointments or visits occur between study visits and are not scheduled as part of the study. Any unscheduled visit during the study must be documented in the eDC system using the eCRFs under "unscheduled visit" (Unscheduled Visit: Physical Exam eCRF, Unscheduled Visit: Clinical Pathology eCRF, and IDEXX Lab Form). Each new diagnosis or clinical sign a dog exhibits will be recorded on the Medical History Log and as an AE in the Adverse Event (AE) Log, if applicable. All AEs will be handled as described in Section 15.

After completion of the PE and the Unscheduled Visit: Physical Exam eCRF, any diagnostics performed are at the discretion of the Investigator. Any diagnostics performed must be documented in the dog's medical record and on the Unscheduled Visit: Physical Exam eCRF. The Medical History Log and Concomitant Medications Log should also be updated with any changes or new prescriptions.

One Week Dosing Phone Calls. Dog Owners will not be required to complete a daily dosing log for this study. However, the first week of dosing is critical to achieving the desired effect of the IVP used in this study. To ensure no missed doses in the first week, a follow-up phone call from site personnel will be required 5-7 days after initiating dosing (study visit 3). The study site personnel will use the One Week Dosing Check-In eCRF to record the results of the contact with the Owner.

Owners who report missed doses in the first week must report how many doses were missed, and the site personnel will add this information, plus any other comments, to the One Week Dosing Check-In eCRF. Site personnel will also complete the Protocol Deviation: Subject Level Form.

Palatability Questionnaire. At study visits 3-6, the Owner will be asked by site personnel to answer three yes or no questions regarding the palatability of the study drug. The responses will be recorded on the Platability Questionnaire eCRF.

Study Design

The study will be a multi-site, field pilot study. The design is a randomized, masked, placebo-controlled study in client-owned dogs. The study will contain two treatment groups randomized at a 3:1 ratio in Table 10 below.

TABLE 10

Randomization of Treatment Groups

| Treatment Group | Number of Dogs | Treatment |
|---|---|---|
| 1 | 45 | IVP |
| 2 | 15 | CP |

Once the subject is deemed eligible for randomization, study site staff will use the integrated Prelude Just-in-Time (JIT) randomization module on the Randomization eCRF to allocate each subject to a randomly selected treatment group. The JIT randomization module will adaptively randomly assign subjects to a treatment group. In the event that a subject is given an incorrect treatment by mistake, the randomization module will be enabled to correct the treatment code assignment and update the treatment code to what was administered. The JIT randomization module will assign a 3:1 allocation ratio of IVP:CP. This will result in a treatment block of four. Blocks of four will be stratified by site so that each site will have its own blocks to draw from at randomization. Randomization will occur by order of presentation within each site at study visit 2. For example, the first dog randomized at site one (1) will be randomly allocated to a treatment group, and the unique bottle numbers available at the site will auto-populate (depending on their dose based on their screening visit weight). The second dog presenting at the same site will then be randomized based on the remaining treatment groups within that site's unique block of four, and so on.

Study Procedures

Table 11 below provides a description of the animals used in this study

TABLE 11

Animal Description

| | |
|---|---|
| Species: | Canine |
| Age: | 7-10 years of age |
| Sex: | Any sex - intact or neutered |
| Breed: | Any breed |
| Body weight: | ≥14 pounds or ≤179 pounds |
| Physiological status: | Must be non-pregnant, non-lactating, not intended for breeding |

The study will enroll an estimated 60 dogs across all study sites. Approximately 45 dogs will be treated with IVP, and approximately 15 dogs will be treated with CP. Additional dogs may be enrolled if initial attrition rates exceed the anticipated level. Likewise, fewer dogs may be enrolled if the study ends before full enrollment.

Inclusion/exclusion criteria. For dogs to be screened at study visit 1, complete study enrollment, and be randomized into treatment groups, they must meet all eligibility requirements. The screening visit/study visit 1 will confirm initial eligibility with the completion of PE, medical history, and concomitant medications. Age verification and the results obtained from clinical pathology collected at study visit 1 will complete final eligibility on or before study visit 2. The Investigator must review the CBC, biochemical profile, and T4 to verify eligibility and complete the Eligibility Form. Subjects not eligible for enrollment may be contacted and informed, so they need not come for study visit 2. Subjects who are eligible to enroll in the study will be randomized at study visit 2.

Inclusion Criteria. The following dogs may be included:

Multiple dogs from the same household

Dogs that meet the criteria in the animal description above

Dogs with a heart murmur and no other clinical signs associated with heart disease Dogs with stage B1 Myxomatous Mitral Valve Degeneration (MMVD)

Dogs with benign neoplastic disease

Dogs who have clinical pathology abnormalities indicating underlying disease processes which the Investigator deems either not clinically significant or not consistent with any of the exclusion criteria below Exclusion Criteria. The following dogs will be excluded form the study:

Dogs not expected to survive six (6) months

Dogs with an established diagnosis of hypoadrenocorticism or hyperadrenocorticism Dogs with established or suspected diagnosis of malignant neoplasia Dogs with an established diagnosis of diabetes mellitus Established diagnosis of liver disease (via function test such as bile acids)

Established diagnosis of dilated cardiomyopathy, Arrhythmogenic Right Ventricular Cardiomyopathy (ARVC/boxer cardiomyopathy), or Congestive Heart Failure (CHF)

Established diagnosis of autoimmune disease which requires immunosuppressive medications Dogs with anemia with hematocrit <30

Dogs that demonstrate a temperament not compatible with performing study procedures Dogs on a prohibited medication or conditionally allowed medication outside the conditions Age Verification. During the screening visit/study visit 1, or on or before study visit 2, the dog's age must be verified by confirming and uploading approved documentation listed below:

A breeding record or registration papers showing an exact date of birth

A record documenting examination or treatment of the dog by a veterinarian which occurred when the dog was estimated to be one (1) year of age or younger Shelter adoption records for dogs that were puppies (less than six (6) months) at the time of adoption Veterinary records from the shelter showing neutering performed when the dog was listed as one (1) year of age or younger at the time of the procedure The dog's date of birth (set to the first day of the month, if estimated) and validation source provided by the Owner will be documented in the Demographics eCRF. This source document will be copied, scanned, and uploaded to the Document Upload Form in the eDC. Owner Informed Consent. The Owner consent must be obtained from each Owner using the OIC Form before any study-related procedures are performed on a subject. This form will be completed at the screening visit/study visit 1.

Masking of Study. The Owner, Investigator, study site staff, and Sponsor will be masked to the treatment group. Study site personnel dispensing the IVP/CP should not speculate or discuss the treatment groups with the Owner.

Study Facilities. The study sites will be clinical veterinary facilities whose personnel, facilities, equipment, record keeping, and anticipated compliance with study procedures outlined in the protocol will foster unbiased research assessments. All study site qualifications will be validated as outlined. The site Investigator will be a licensed Doctor of Veterinary Medicine (DVM or VMD). Additional study site personnel must include at least one Licensed Veterinary Technician (LVT) or veterinary assistant. It is estimated that approximately three study sites will be recruited to execute this study. Recruitment of sites may continue until three or more study sites are attained.

Study Equipment. Scales used at the study site to obtain exam body weight must have been calibrated by a certified technician within one (1) year before first use in the study. A copy of the site's calibration record will be uploaded to the Clinical Trial Management System (CTMS) and retained in the electronic Trial Master File (eTMF). Calibrations expire after one (1) year, and study sites will require a certified technician to calibrate the scale annually, as needed.

All enrolled dogs will remain in their normal housing conditions with their Owners. There are no special dietary requirements for participation in this study; Owners should continue to feed their dogs their normal diet. Normal diets include prescription diets prescribed previously or during the study. The subject's diet and feeding schedule will be documented as part of the Physical Exam eCRF at each associated study visit. Prescription diets will be recorded on the Concomitant Medications Log.

Drug Administration. IVP/CP will be administered by the Owner to the subject once daily starting at study visit 2 and for the duration of the study. The administration route for IVP and CP is by mouth (PO).

Owners will not complete a dosing log. Missed doses will be confirmed when the Owner returns their study drug bottle(s), and the unadministered doses are counted each month when they pick up IVP/CP refills. Monthly returned bottles, missed doses, incorrectly administered doses, associated missed or incorrect dosage dates, and refills will be recorded on the Study Drug: Subject Log. If an Owner gives the incorrect dosage or misses on average more than 8 doses per month, it will be recorded as a protocol deviation on the Protocol Deviation: Subject Level Form, but the dog will not be removed from the study. Dispensing and accounting for tablets not administered will occur on drug dispensing.

The Owner must not miss any doses during the first week of the study as it may affect the drug reaching an initial level to affect the pharmacodynamics of biomarkers in the dog.

Missed doses in the first week will be recorded on the One Week Dosing Check-In eCRF and as a protocol deviation on the Protocol Deviation: Subject Level Form.

Removal Criteria. Study completion for each enrolled dog is the time when study assessments and treatments are discontinued. Study completion may be due to subject removal from the study if removal criteria are met, see Section 8.7. Upon study completion, the Investigator must complete the Study Exit Form to document the date and, if applicable, reasons why the dog is removed from the study.

Removing Dogs. The following dogs will be removed from the study, and the Study Exit Form must be completed:
  Anemia with HCT<30
  Dogs diagnosed with diabetes mellitus
  Dogs with suspected or confirmed bladder cancer
  Dogs with sudden or unexpected worsening edema/fluid retention or CHF
  Dogs diagnosed with hyperadrenocorticism or hypoadrenocorticism
  Dogs found to have been enrolled in error
  Dogs requiring a prohibited medication
  Dogs that experience an SAE requiring unmasking or removal from the treatment
  Dogs whose Owner is non-compliant with study procedures (including the dog missing a study visit over the allowable timeline or missing too many doses of the study)
  Dogs whose Owner elects to withdraw the dog from the study
  Dogs that become uncooperative with study procedures Removed Dogs. In some situations, it will be necessary to follow up on clinical pathology abnormalities, AEs, and SAEs. This follow-up is essential in determining if the abnormalities, AEs, or SAEs are of clinical significance and understanding the relationship to the IVP. Dogs that are found to have elevated liver enzymes should not necessarily be immediately removed from the study if the Investigator or study veterinarian feels it is acceptable to continue. Because elevated liver enzymes are non-specific and not always clinically significant, the Investigator will be permitted to exercise discretion in handling these cases. If the dog continues enrollment, they will have blood biochemistry profiles rechecked (which includes liver enzymes: AST, ALT, ALP, bilirubin) every 30 days, an appropriate recheck interval given half-lives of the liver enzymes. If the recheck liver values are equal to or elevated from the originally detected elevated liver enzymes and the veterinarian thinks it prudent, the dog can be removed from the study, and the Investigator will complete the Study Exit Form.

Concomitant Medications. Concomitant medications are defined as any medications or treatments the dog receives at the screening visit/study visit 1 and any time after that during the study. This includes, but is not limited to, flea and tick preventatives, supplements, prescription diets, and prescription medications. If the dog has received a medication noted in Table 4 under "conditionally allowed," the Investigator or examining veterinarian must ensure that the dog meets the criteria under the conditionally allowed column of Table 8 before completing further study procedures. At each visit, any new or ongoing concomitant medications and the relevant medical history must be recorded on the Medical History Log and Concomitant Medication Log.

Allowed medications are medications that dogs are not restricted from receiving for the duration of the study. There is no withdrawal or conditions for the use of these medications. For this study, it is essential that the dogs enrolled represent the normal population of dogs, so most medications and supplements are allowed. Conditionally allowed medications are permitted for use during the study with some qualifiers or observed time period. Prohibited medications are those which are not allowed at all for use in the study either because they duplicate the effects of the IVP or because their use may be complicated with the addition of the IVP.

Table 12 below details common concomitant medications and relevance to this study's subject inclusion/exclusion criteria.

TABLE 12

| | Concomitant Medications | | | |
|---|---|---|---|---|
| Medication | Allowed at enrollment | Allowed during study | Conditionally Allowed | Prohibited |
| Insulin | | | | ✓ |
| Metformin | | | | ✓ |
| Selegiline | | ✓ | | |
| Levothyroxine | ✓ | ✓ | | |
| NSAIDs | ✓ | ✓ | | |
| Steroids | ✓* | ✓ | ✓ | |

* Allowed on Day 0 if not immunosuppressive doses (primarily due to health status of dogs diagnosed with autoimmunity and side effects from immunosuppressive doses of steroids are many)

TABLE 12-continued

Concomitant Medications

| Medication | Allowed at enrollment | Allowed during study | Conditionally Allowed | Prohibited |
|---|---|---|---|---|
| Chemotherapeutic agents | | ✓ | | |
| Sedatives and Anesthetics | ✓* | ✓ | ✓<br>* Must have a two-week washout before Day 0 (primarily due to effects of procedures such as surgery on HRQL) | |
| Opioids (excluding tramadol) | ✓* | ✓ | ✓<br>* Must have a two-week washout before Day 0 (primarily due to effects of procedures such as surgery on HRQL) | |
| Tramadol | ✓ | ✓ | | |
| Anti-parasiticides (including HW px, ectoparasiticides, dewormers) | ✓ | ✓ | | |
| Supplements, prescription diets, nutraceuticals, including CBD, glucosamine, fish oil, etc. | ✓ | ✓ | | |
| Vaccinations | ✓ | ✓ | | |
| Antibiotics excluding macrolides and fluoroquinolones and macrocyclics | ✓ | ✓ | | |
| Fluoroquinolone antibiotics (ciprofloxacin, enrofloxacin, difloxacin, orbifloxacin, marbofloxacin) | | | ✓<br>*Dogs must come off study drug during the course of antibiotics then may resume | |
| Ketoconazole | | | ✓<br>*Dogs must come off study drug during the course of antibiotics then may resume | |
| Non-ketoconazole antifungals (miconazole, fluconazole, etc.) | ✓ | ✓ | | |
| Heart medications which are not ACE inhibitors nor ACE receptor blockers | ✓ | ✓ | | |
| ACE inhibitors and ACE receptor blockers (telmisartan, enalapril, benazepril, imidapril, ramipril) | | | | ✓ |
| Antihistamines | ✓ | ✓ | | |
| Serotonergic drugs (trazodone, fluoxetine, etc.) | ✓ | ✓ | | |
| Gabapentin | ✓ | ✓ | | |
| Apoquel, Cytopoint | ✓ | ✓ | | |

When recording concomitant medications during the screening visit/study visit 1, the discovery that a dog is receiving a prohibited medication is cause for exclusion of the dog from the study. The medication and reason for exclusion will be documented in the Concomitant Medication Log, Eligibility Form, and Study Exit Form.

Dog Disposition. Dogs will always be in the custody of their Owner. Dogs withdrawn or removed early from the study will remain in the custody of their Owner.

Results in Dogs Treated with Pioglitazone

This study generated the following conclusions: Dogs in the control group showed an average increase in insulin levels of 3.85 (uIU/mL 95% CI=1.37, 9.06) from baseline to day 90. This increase was not statistically significant (p=0.132). Dogs treated with pioglitazone showed an average reduction in insulin levels of 2.35 (uIU/mL 95% CI=10.07, 5.36) from baseline to day 90, however this reduction was not statistically significant (p=0.538). Average reductions in insulin levels in dogs treated with pioglitazone were trending lower than dogs in the control group (p=0.171). The study was underpowered and of short duration such that statistical differences in insulin between the groups demonstrating effectiveness were likely not detectable.

There was, however, a notable effect on insulin levels in three pioglitazone-treated dogs with elevated baseline insulin levels. This effect warrants a closer look at these three individual outlier dogs with elevated fasting insulin levels and their responses to treatment with pioglitazone. These case studies demonstrate not only the acute effect of treatment with pioglitazone, but important safety data in dogs who were not at peak metabolic health.

Subject 001-SAR-007 was a 9 year old, neutered male, Yorkshire terrier. On screening visit his insulin was 76.8 uIU/mL (reference range 5.2-41.5 uIU/mL). In addition, he had elevated ALP at 177 U/L (reference range 5-160 U/L), AST at 182 U/L (reference range 16-55 U/L), ALT at 469 U/L (reference range 18-121 U/L), and TBili at 0.5 mg/dL (reference range 0.00.3 mg/dL). Before randomization, the study veterinarian performed pre and post prandial bile acids which were within normal limits. Less than one month later, after starting pioglitazone, the dog's liver values were all returned to normal (ALP 88 U/L, AST 22 U/L, ALT 48 U/L, and TBili 0.2 mg/dL), as was his insulin (16.2 uIU/mL).

Subject 003-BAK-016 was a 7 year old, neutered male, Welsh terrier. On screening visit his insulin was 96.6 uIU/mL (reference range 5.2-41.5 uIU/mL) and ALP was 241 U/L (reference range 5-160 U/L). Though his ALP remained elevated, his insulin gradually reduced at subsequent visits to 62.2 uIU/mL, then down to 52.9 uIU/mL, and finally by visit 6, 90 days later, down to 42.3 uIU/mL.

Subject 003-BAK-018 was an 8 year old, spayed female, cocker spaniel. On the screening visit she had insulin of 66.3 uIU/mL (reference range 5.2-41.5 uIU/mL) and ALP of 1603 U/L (reference range 5-160 U/L). The study veterinarian was concerned about Cushing's disease and performed a low dose dexamethasone suppression test which was normal. By visit 4 (approximately day 30) after starting pioglitazone her insulin was returned to 15.3 uIU/mL and ALP was down to 774 U/L.

These 3 cases confirm the acute effect of improving metabolic function and reduction of fasting insulin. These dogs also experienced various additional improvements in their clinical pathology including reduction in liver enzymes (all 3 dogs), and reduction or normalization of triglycerides and eliminating gross lipemia in the blood samples submitted to IDEXX (001-SAR-007 and 003-BAK-018).

Example 7. Safety of Pioglitazone in Dogs

The safety of pioglitazone in dogs in dogs has been evaluated in a number of laboratory studies and a recent clinical study.

| Duration of Study | # of Dogs | Oral Doses (mg/kg/day) | Findings |
| --- | --- | --- | --- |
| 4 weeks | 24 | 0, 1, 3, 10 | No toxicity occurred in the dogs at doses up to 10 mg/kg/day. |
| 12 weeks (3 months) | 40 | 0, 1, 3, 10 | There was a statistically significant, though not clinically significant: Reduction in hematocrit in both sexes on days 72 and 90 in the 10 mg/kg group. Levels returned to normal during the recovery phase. Decrease in serum albumin and protein and increased alanine aminotransferase (ALT), lactate dehydrogenase, and chloride in dogs treated with 10 mg/kg/day Increase in heart weight in the 10 mg/kg group. |
| 12 weeks (3 months) | 44 | 0, 30, 60, 150 | The drug was not well tolerated, but all the dogs apart from two in the 150 mg/kg/day group survived to the end of the study. Clinical signs associated with drug treatment included vomiting, diarrhea and soft stool, anemia manifested as a pale oral mucosa and abdominal distension. The frequency appeared dose-dependent. This gives us confidence that if a dog accidentally e.g. ingests an entire bottle of pills, they should be OK. |
| 52 weeks (1 year) | 48 | 0, 1, 3, 10 | Following the 1-year dosing phase, 16 dogs were maintained without drug exposure for a 4-month reversibility phase where drug was withdrawn and values monitored. There was evidence of regenerative anemia that was not clinically significant* in females of the mid-dose group, and males and females of the 10 mg/kg group. There was a statistically significant, though not clinically significant* |

-continued

| Duration of Study | # of Dogs | Oral Doses (mg/kg/day) | Findings |
|---|---|---|---|
| 26 weeks (6 months) | 32 | 0, 1, 3, 10 | increase in ALT in males treated with 10 mg/kg, but this returned to normal in the reversibility phase where drug was withdrawn and values monitored. There was a statistically significant, though not clinically significant*, increase in platelet and leukocytes in 10 mg/kg treated females. Increased heart weight and hydropericardium in one male, and increased spleen weight in one female, were seen in the 10 mg/kg treated group. The nontoxic dose was determined to be 3 mg/kg/day. |

*not clinically significant indicates there were no clinical signs associated with the finding Example 8. Formulations of Pioglitazone Pioglitazone or a salt thereof can be formulated in any one of the tablet forms described below in Table 13.

TABLE 13

Formulations of Pioglitazone in 18 mg, 54 mg, and 81 mg tablets

| Phase | Ingredients | 18 mg mg/tab | 54 mg mg/tab | 81 mg mg/tab |
|---|---|---|---|---|
| Intra-granulation | Pioglitazone Hydrochloride API | 19.8 | 59.4 | 89.1 |
| | Lactose monohydrate (GranuLac 200) | 66.06 | 198.18 | 297.27 |
| | Carboxymethyl Cellulose Na | 7.92 | 23.76 | 8.1 |
| | Hydroxypropyl Cellulose EXF | 1.80 | 5.4 | 8.1 |
| | Purified Water | | | |
| | Subtotal | 95.58 | 286.74 | 430.11 |
| Tablet Blend | Pioglitazone intra-granulation | 95.58 | 286.74 | 430.11 |
| | Lactose monohydrate (FlowLac 100) | 39.60 | 118.80 | 178.20 |
| | Carboxymethyl Cellulose Na | 7.02 | 21.06 | 31.59 |
| | FlavorPAL X1212 | 36.00 | 108.00 | 162.00 |
| | Magnesium Stearate | 1.80 | 5.40 | 8.10 |
| | TOTAL | 180.00 | 540.00 | 810.00 |

Example 9. Formulations of Pioglitazone

Pioglitazone or a salt thereof can be formulated in any one of the tablet forms described below in Table 14.

TABLE 14

Formulations of Pioglitazone by % wt/wt

| Ingredients | Wt, % |
|---|---|
| Pioglitazone HCl | 16.50 |
| Lactose Monohydrate | 55.00 |
| Carboxymethyl Cellulose | 6.60 |
| Povidone K30 or Hydroxypropyl Cellulose | 1.50 |
| Purified Water[1] | — |
| Spray Dried Lactose | 4.00 |
| Flavor | 12.00 |
| Croscarmellose Sodium | 1.70 |

TABLE 14-continued

Formulations of Pioglitazone by % wt/wt

| Ingredients | Wt, % |
|---|---|
| Carboxymethyl Cellulose Calcium | 1.70 |
| Magnesium Stearate | 1.00 |
| Total | 100.00 |

Example 10. Formulations of Pioglitazone

Pioglitazone or a salt thereof can be formulated in any one of the tablet forms described below in Table 15.

TABLE 15

Formulations of Pioglitazone by % wt/wt

| Ingredients | Wt, % |
|---|---|
| Pioglitazone HCl | 11.00 |
| Lactose | 36.00 |
| Croscarmellose Sodium | 2.00 |
| hydroxypropyl cellulose | 1.00 |
| Purified Water | — |
| Spray Dried Lactose | 37.00 |
| Flavor | 10.00 |
| Carboxymethyl cellulose | 2.00 |
| Colloidal Silicon Dioxide | 1.00 |
| Total | 100.00 |

Example 11. Formulations of Pioglitazone

Pioglitazone or a salt thereof can be formulated in any one of the tablet forms described below in Table 16.

TABLE 16

Formulations of Pioglitazone by % wt/wt

| Ingredients | % wt/wt |
|---|---|
| Pioglitazone Hydrochloride API | 12.33 |
| Microcrystalline Cellulose | 21.46 |
| Hydroxypropyl Cellulose EXF | 2 |
| Spray Dried Lactose | 45 |
| Flavor | 15 |
| Polyplasdone XL | 2 |

TABLE 16-continued

Formulations of Pioglitazone by % wt/wt

| Ingredients | % wt/wt |
|---|---|
| Colloidal Silicon Dioxide | 1 |
| Magnesium Stearate | 1.2 |
| TOTAL | 100 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for reducing or delaying mortality due to age-associated diseases in a companion animal in need thereof, comprising orally administering to the companion animal a therapeutically effective amount of a formulation comprising pioglitazone or a pharmaceutically acceptable salt or prodrug thereof, wherein the formulation is administered for at least 2 weeks,
   wherein the companion animal is a dog, and wherein the pioglitazone or the pharmaceutically acceptable salt or prodrug thereof is administered as the sole therapeutic agent.

2. The method of claim 1, wherein the pioglitazone or a pharmaceutically acceptable salt or prodrug thereof is pioglitazone hydrochloride.

3. The method of claim 1, wherein the pioglitazone or the pharmaceutically acceptable salt or prodrug thereof is administered at about 2 to 3 mg/kg/day.

4. The method of claim 1, wherein the pioglitazone or the pharmaceutically acceptable salt or prodrug thereof is administered at about 1 to 5 mg/kg/day.

5. The method of claim 1, wherein the pioglitazone or the pharmaceutically acceptable salt or prodrug thereof is administered at an amount of up to 10 mg/kg/day.

6. The method of claim 1, wherein the formulation is administered once daily.

7. The method of claim 1, wherein the formulation is administered for at least about 4 weeks.

8. The method of claim 1, where the formulation is administered for at least about 12 weeks.

9. The method of claim 1, where the formulation is administered for at least about 1 year.

10. The method of claim 1, wherein the method comprises decreasing an insulin level in the companion animal.

11. The method of claim 10, wherein the insulin level is decreased by at least 5%.

12. The method of claim 1, wherein the method improves insulin sensitivity.

13. The method of claim 12, wherein the insulin sensitivity is measured by an oral glucose tolerance testing assay or by a hyperinsulinemic euglycemic clamp testing assay.

14. The formulation for use according to claim 12, wherein the insulin sensitivity is measured by a shortened or modified oral glucose tolerance testing assay.

15. The method of claim 12, wherein the insulin sensitivity is measured by using fasting insulin blood levels.

16. The method of claim 1, wherein the method decreases a triglyceride level in the companion animal.

17. The method of claim 1, wherein the method decreases a cholesterol level in the companion animal.

18. The method of claim 1, wherein the method further comprises mitigating an age-induced elevation of fatty acid, wherein the fatty acid is aggregated free fatty acids, saturated fatty acids, palmitic acid, linoleic acid, or oleic acid, or any combination thereof.

19. The method of claim 1, wherein the companion animal is at least 7 years old.

20. The method of claim 1, wherein the companion animal is at least 10 years old.

21. The method of claim 1, wherein the companion animal is at least 14 pounds.

22. The method of claim 1, wherein the formulation comprises about 5% to about 15% of the pioglitazone or the pharmaceutically acceptable salt or prodrug thereof.

23. The method of claim 1, wherein the formulation comprises about 4 mg to about 85 mg of the pioglitazone or the pharmaceutically acceptable salt or prodrug thereof.

24. The method of claim 1, wherein the formulation is in a form of a tablet.

25. The method of claim 24, wherein the tablet comprises 18 mg, 54 mg, or 81 mg of the pioglitazone or the pharmaceutically acceptable salt or prodrug thereof.

* * * * *